US012053518B2

(12) United States Patent
Batard et al.

(10) Patent No.: US 12,053,518 B2
(45) Date of Patent: Aug. 6, 2024

(54) METHOD FOR RESCUING AND PRODUCING A VIRUS IN AVIAN CELLS

(71) Applicant: Valneva SE, Saint-Herblain (FR)

(72) Inventors: Luc Batard, Saint-Herblain (FR); Caroline Freslon-Evain, Orvault (FR); Fabien Perugi, Nantes (FR); Klaus Schwamborn, Nantes (FR)

(73) Assignee: Valneva SE, Nantes (FR)

( * ) Notice: Subject to any disclaimer, the term of this patent is extended or adjusted under 35 U.S.C. 154(b) by 177 days.

(21) Appl. No.: 17/260,054

(22) PCT Filed: Jul. 15, 2019

(86) PCT No.: PCT/EP2019/069030
§ 371 (c)(1),
(2) Date: Jan. 13, 2021

(87) PCT Pub. No.: WO2020/012037
PCT Pub. Date: Jan. 16, 2020

(65) Prior Publication Data
US 2021/0275662 A1    Sep. 9, 2021

(30) Foreign Application Priority Data
Jul. 13, 2018  (EP) .................................... 18183324

(51) Int. Cl.
*A61K 39/17*  (2006.01)
*A61K 39/39*  (2006.01)
*C12N 7/00*   (2006.01)
*A61K 39/00*  (2006.01)

(52) U.S. Cl.
CPC .............. *A61K 39/17* (2013.01); *A61K 39/39* (2013.01); *C12N 7/00* (2013.01); *A61K 2039/5256* (2013.01); *A61K 2039/5258* (2013.01); *A61K 2039/55505* (2013.01); *A61K 2039/6043* (2013.01); *C12N 2760/18134* (2013.01); *C12N 2760/18334* (2013.01); *C12N 2760/18534* (2013.01)

(58) Field of Classification Search
CPC .............. A61K 2039/5256; A61K 3/12; A61K 2039/55577; A61K 2039/55555; A61K 2039/5252; A61K 2039/5258; A61K 2039/55572; A61K 9/1271; A61K 9/127; A61K 9/51; A61K 47/6929; A61K 31/19; A61K 2039/525; A61K 9/284; A61K 9/2013; A61K 39/17; C12N 2760/16122; C12N 7/00; C12N 2760/16134; C12N 2760/16123
See application file for complete search history.

(56) References Cited

U.S. PATENT DOCUMENTS

| | | | |
|---|---|---|---|
| 6,544,785 B1* | 4/2003 | Palese | C07K 14/005 435/456 |
| 7,951,383 B2* | 5/2011 | Murphy | C12N 7/00 424/211.1 |
| 2016/0060301 A1* | 3/2016 | Jewett | C12N 9/1247 435/252.33 |

FOREIGN PATENT DOCUMENTS

| | | |
|---|---|---|
| EP | 1939214 A1 | 7/2008 |
| WO | WO 1999/024068 A1 | 5/1999 |
| WO | WO 2003/076601 A1 | 9/2003 |
| WO | WO 2004/113517 A2 | 12/2004 |
| WO | WO 2005/042728 A2 | 5/2005 |
| WO | WO 2008/129058 A1 | 10/2008 |
| WO | WO 2016/156613 A1 | 10/2016 |

OTHER PUBLICATIONS

Bai et al. Molecular Biology, 2015, vol. 49, No. 2, pp. 171-178.*
Peeters et al. (B) (Vaccine vol. 19, Issue 13-14, pp. 1616-1627).*
[No Author Listed], Molecular Biology Reference. Addgene Online Plasmid Repository. Retrieved from addgene.org/mol-bio-reference/#elements. Accessed on Mar. 11, 2021. 9 pages.
[No Author Listed], Newcastle Disease Virus (PDQ®). Health Professional Version. Retrieved from ncbi.nlm.nih.gov/books/NBK65752/. Epub Aug. 22, 2018. 40 pages.
Alexander et al., Newcastle disease and other avian paramyxoviruses. Rev Sci Tech. Aug. 2000;19(2):443-62. doi: 10.20506/rst.19.2.1231.
Altschul et al., Basic local alignment search tool. J Mol Biol. Oct. 5, 1990;215(3):403-10. doi: 10.1016/S0022-2836(05)80360-2.
Altschul et al., Gapped BLAST and PSI-BLAST: a new generation of protein database search programs. Nucleic Acids Res. Sep. 1, 1997;25(17):3389-402. doi: 10.1093/nar/25.17.3389.
Ausubel et al., Current Protocols in Molecular Biology. 2003. John Wiley & Sons, Inc. 4648 pages.
Beaty et al., Efficient and Robust Paramyxoviridae Reverse Genetics Systems. mSphere. Mar. 29, 2017;2(2):e00376-16. doi: 10.1128/mSphere.00376-16.
Biacchesi et al., Modification of the trypsin-dependent cleavage activation site of the human metapneumovirus fusion protein to be trypsin independent does not increase replication or spread in rodents or nonhuman primates. J Virol. Jun. 2006;80(12):5798-806. doi: 10.1128/JVI.00294-06.

(Continued)

*Primary Examiner* — Bao Q Li
(74) *Attorney, Agent, or Firm* — Wolf, Greenfield & Sacks, P.C.

(57) ABSTRACT

The present invention relates to methods of rescue and/or propagation of paramyxovirus species, particularly wherein both rescue and propagation are carried out in the same cell type; i.e., without the use of helper cells for viral rescue. The paramyxoviruses produced by the disclosed methods may encompass wild-type viruses, chimeric viruses, recombinant viruses or engineered viral products such as virus like particles (VLP). Viruses and/or viral products produced in the method according to the current invention are suitable for medical or veterinary use in such applications as treating or preventing infectious diseases, particularly avian paramyxovirus and human respiratory virus infections, and cancer treatment.

15 Claims, 16 Drawing Sheets

Specification includes a Sequence Listing.

(56) References Cited

OTHER PUBLICATIONS

Brown et al., The Avian EB66® Cell Line, Application to Vaccines, and Therapeutic Protein Production. PDA J Pharm Sci Technol. Sep.-Oct. 2010;64(5):419-25.
Bukreyev et al., Recombinant Newcastle disease virus expressing a foreign viral antigen is attenuated and highly immunogenic in primates. J Virol. Nov. 2005;79(21):13275-84. doi: 10.1128/JVI.79.21.13275-13284.2005.
De Leeuw et al., Complete nucleotide sequence of Newcastle disease virus: evidence for the existence of a new genus within the subfamily Paramyxovirinae. J Gen Virol. Jan. 1999;80 ( Pt 1):131-136. doi: 10.1099/0022-1317-80-1-131.
De Leeuw et al., Effect of fusion protein cleavage site mutations on virulence of Newcastle disease virus: non-virulent cleavage site mutants revert to virulence after one passage in chicken brain. J Gen Virol. Feb. 2003;84(Pt 2):475-484. doi: 10.1099/vir.0.18714-0.
Dinapoli et al., Respiratory tract immunization of non-human primates with a Newcastle disease virus-vectored vaccine candidate against Ebola virus elicits a neutralizing antibody response. Vaccine. Dec. 10, 2010;29(1):17-25. doi: 10.1016/j.vaccine.2010.10.024. Epub Oct. 27, 2010.
Fiola et al., Tumor selective replication of Newcastle disease virus: association with defects of tumor cells in antiviral defence. Int J Cancer. Jul. 15, 2006;119(2):328-38. doi: 10.1002/ijc.21821.
Ge et al., Newcastle disease virus-based live attenuated vaccine completely protects chickens and mice from lethal challenge of homologous and heterologous H5N1 avian influenza viruses. J Virol. Jan. 2007;81(1):150-8. doi: 10.1128/JVI.01514-06. Epub Oct. 18, 2006.
Inoue et al., An improved method for recovering rabies virus from cloned cDNA. J Virol Methods. Feb. 2003;107(2):229-36. doi: 10.1016/s0166-0934(02)00249-5.
Jordan et al., An avian cell line designed for production of highly attenuated viruses. Vaccine. Jan. 29, 2009;27(5):748-56. doi: 10.1016/j.vaccine.2008.11.066. Epub Dec. 9, 2008.
Kalyanasundram et al., Newcastle disease virus strain AF2240 as an oncolytic virus: A review. Acta Trop. Jul. 2018;183:126-133. doi: 10.1016/j.actatropica.2018.04.007. Epub Apr. 4, 2018.
Katoh et al., Recent developments in the MAFFT multiple sequence alignment program. Brief Bioinform. Jul. 2008;9(4):286-98. doi: 10.1093/bib/bbn013. Epub Mar. 27, 2008.
Kim et al., Newcastle Disease Virus as a Vaccine Vector for Development of Human and Veterinary Vaccines. Viruses. Jul. 4, 2016;8(7):183. doi: 10.3390/v8070183.
Kim et al., Respiratory syncytial virus disease in infants despite prior administration of antigenic inactivated vaccine. Am J Epidemiol. Apr. 1969;89(4):422-34. doi: 10.1093/oxfordjournals.aje.a120955.
Krishnamurthy et al., Differentially regulated interferon response determines the outcome of Newcastle disease virus infection in normal and tumor cell lines. J Virol. Jun. 2006;80(11):5145-55. doi: 10.1128/JVI.02618-05.
Krishnamurthy et al., Nucleotide sequences of the trailer, nucleocapsid protein gene and intergenic regions of Newcastle disease virus strain Beaudette C and completion of the entire genome sequence. J Gen Virol. Oct. 1998;79 ( Pt 10):2419-24. doi: 10.1099/0022-1317-79-10-2419.
Kumar et al., Evaluation of the Newcastle Disease Virus F and HN Proteins in Protective Immunity by Using a Recombinant Avian Paramyxovirus Type 3 Vector in Chickens. J Virol. Feb. 28, 2020;94(6):e01867-19. doi: 10.1128/JVI.01867-19.
Larkin et al., Clustal W and Clustal X version 2.0. Bioinformatics. Nov. 1, 2007;23(21):2947-8. doi: 10.1093/bioinformatics/btm404. Epub Sep. 10, 2007.
Leemans et al., Antibody-Induced Internalization of the Human Respiratory Syncytial Virus Fusion Protein. J Virol. Jun. 26, 2017;91(14):e00184-17. doi: 10.1128/JVI.00184-17.
Manoharan et al., A Y527A mutation in the fusion protein of Newcastle disease virus strain LaSota leads to a hyperfusogenic virus with increased replication and immunogenicity. J Gen Virol. Feb. 2016;97(2):287-292. doi: 10.1099/jgv.0.000350. Epub Nov. 19, 2015.
Nakaya et al., Recombinant Newcastle disease virus as a vaccine vector. J Virol. Dec. 2001;75(23):11868-73. doi: 10.1128/JVI.75.23.11868-11873.2001.
Needleman et al., A general method applicable to the search for similarities in the amino acid sequence of two proteins. J Mol Biol. Mar. 1970;48(3):443-53. doi: 10.1016/0022-2836(70)90057-4.
Panda et al., Role of fusion protein cleavage site in the virulence of Newcastle disease virus. Microb Pathog. Jan. 2004;36(1):1-10. doi: 10.1016/j.micpath.2003.07.003.
Pearson et al., Improved tools for biological sequence comparison. Proc Natl Acad Sci U S A. Apr. 1988;85(8):2444-8. doi: 10.1073/pnas.85.8.2444.
Peeters et al., Genome replication of Newcastle disease virus: involvement of the rule-of-six. Arch Virol. 2000;145(9):1829-45. doi: 10.1007/s007050070059.
Peeters et al., Rescue of Newcastle disease virus from cloned cDNA: evidence that cleavability of the fusion protein is a major determinant for virulence. J Virol. Jun. 1999;73(6):5001-9. doi: 10.1128/JVI.73.6.5001-5009.1999.
Qian et al., Newcastle disease virus-like particles induce dendritic cell maturation and enhance viral-specific immune response. Virus Genes. Aug. 2017;53(4):555-564. doi: 10.1007/s11262-017-1451-1. Epub Apr. 1, 2017.
Rawling et al., Insertion of the two cleavage sites of the respiratory syncytial virus fusion protein in Sendai virus fusion protein leads to enhanced cell-cell fusion and a decreased dependency on the HN attachment protein for activity. J Virol. Jun. 2008;82(12):5986-98. doi: 10.1128/JVI.00078-08. Epub Apr. 2, 2008.
Reed et al., A simple method of estimating fifty per cent endpoints. Am J Hygiene. 1938;27(3): 493-497.
Ren et al., Recent vaccine development for human metapneumovirus. J Gen Virol. Jul. 2015;96(Pt 7): 1515-20. doi: 10.1099/vir.0.000083. Epub Feb. 9, 2015.
Santry et al., Production and Purification of High-Titer Newcastle Disease Virus for Use in Preclinical Mouse Models of Cancer. Mol Ther Methods Clin Dev. Oct. 16, 2017;9:181-191. doi: 10.1016/j.omtm.2017.10.004.
Schlegl et al., Influence of elemental impurities in aluminum hydroxide adjuvant on the stability of inactivated Japanese Encephalitis vaccine, IXIARO®. Vaccine. Nov. 4, 2015;33(44):5989-96. doi: 10.1016/j.vaccine.2015.05.103. Epub Jun. 19, 2015.
Schnell et al., Infectious rabies viruses from cloned cDNA. Embo J. Sep. 15, 1994;13(18):4195-203.
Smith et al., Comparison of Biosequences. Adv Appl Math. 1981;2:482-489.
Steward et al., RNA editing in Newcastle disease virus. J Gen Virol. Dec. 1993;74 ( Pt 12):2539-47. doi: 10.1099/0022-1317-74-12-2539.
Tsunekuni et al., Evaluation of avian paramyxovirus serotypes 2 to 10 as vaccine vectors in chickens previously immunized against Newcastle disease virus. Vet Immunol Immunopathol. Aug. 15, 2014;160(3-4):184-91. doi: 10.1016/j.vetimm.2014.05.001. Epub May 14, 2014.
Yim et al., Human metapneumovirus: enhanced pulmonary disease in cotton rats immunized with formalin-inactivated virus vaccine and challenged. Vaccine. Jun. 28, 2007;25(27):5034-40. doi: 10.1016/j.vaccine.2007.04.075. Epub May 15, 2007.
Zhao et al., P and M gene junction is the optimal insertion site in Newcastle disease virus vaccine vector for foreign gene expression. J Gen Virol. Jan. 2015;96(Pt 1):40-45. doi: 10.1099/vir.0.068437-0. Epub Oct. 1, 2014.
Zhao et al., Recombinant Newcastle disease virus as a viral vector: effect of genomic location of foreign gene on gene expression and virus replication. J Gen Virol. Apr. 2003;84(Pt 4):781-788. doi: 10.1099/vir.0.18884-0.

* cited by examiner pBR322Mod (pVVS01858)

A.

B.

C.

| Restriction Enzyme | Insertion site | Position (nucleotide) | Wild-type sequence | Mutated sequence |
|---|---|---|---|---|
| RE1 (Asc I) | NP/P | 1731 | cgcacgcc | ggcgcgcc |
| RE2 (Fse I) | P/M | 3213 | ggtcgcgt | ggccggcc |
| RE3 (Mlu I) | M/F | 4474 | acctgt | acgcgt |
| RE4 (Pac I) | F/HN | 6243 | taatttgt | ttaattaa |
| RE5 (Sfi I) | HN/L | 8230 | gccggcgcgtgct | ggccgcgcgggcc |
| Correction to published sequence (Accession No: AF077761) | | 12239 | - | g |
| | | 12327 | g | - |

| End of NDV Gene | TAAGAAAAAA | T | ACGGGTAGAA | Kozak GCCACC | ATG.....INSERT |

B.

pVVS01866 (NDV FL + F hMPV B2)

Plasmid map (21350 bp) with labeled features: Start NDV, Prot NP, bla, Rep Origin 1, rop, tet, End NDV, FGT5, ProtL, FGT4, Prot HN, FGT3, Prot F, FGT2, Prot M, Fsd(16264), Prot F hMPV B2, Fsd(17920), Prot P, NDV FGT1.

A.

B.

A.

B.

C.

A. Passage 0 (p0; post-rescue co-culture) hMPV F-protein expression (permeabilized cells)

B. Passage 1 (p1) hMPV F-protein expression

C. Passage 3 (p3) hMPV F-protein expression

| | Trypsin (LaSota) | Furin Site 2 | Furin Site 3 | Furin Site 5 (n=2) | Furin Site 6 | Y527A |
|---|---|---|---|---|---|---|
| d2 | | | | | | |
| d3 | | | | | | |
| d4 | | | | | | |
| d5 | STOP | STOP | | STOP | | STOP |
| Titer $TCD_{50}$/mL Direct light (Vis Figure 10 (continued)

B.

| | Day3 PI | | Day6 PI | |
|---|---|---|---|---|
| Cleavage site in NDV-GFP | $TCID_{50}$/mL white light | $TCID_{50}$/mL UV | $TCID_{50}$/mL white light | $TCID_{50}$/mL UV |
| Trypsin (wild-type) | 5.5 | 7.63 | 0 | 7.38 |
| Furin site 2 | 7.5 | 8.17 | 7.5 | 7.5 |
| Furin site 3 | 4.5 | 5.83 | 3.5 | 6.38 |
| Furin site 5 | 8.38 | 8.50 | 8.38 | 8.50 |
| Furin site 6 | 5,5 | 7,38 | 3,5 | 7,38 |
| Y527A | 3.5 | 7.17 | 3.5 | 7.5 |

| LaSota strain | Max titer in Crude (Log₁₀ TCID₅₀/mL) | Day of harvest (dpi) |
|---|---|---|
| rNDV-FL | 8.0 | 2 |
| rNDV-GFP | 7.5 | 2 |
| rNDV-FA1Native | 8.0 | 2 |
| rNDV-FA1Opt1 | 8.4 | 2 |
| rNDV-FA1Opt2 | 8.0 | 2 |
| rNDV-FA1Opt3 | 8.5 | 2 |
| rNDV-FA1Opt4 | 8.3 | 2 |
| rNDV-sFA1-M | 8.4 | 2 |

Infectious titer (after concentration/purification) $10^{9.5}$ to $10^{10.5}$ TCID₅₀/mL for all tested constructs

*Degradation product of the N protein

SEQUENCE LISTING

```
<160> NUMBER OF SEQ ID NOS: 142

<210> SEQ ID NO 1
<211> LENGTH: 6
<212> TYPE: PRT
<213> ORGANISM: Newcastle disease virus

<400> SEQUENCE: 1

Gly Arg Gln Gly Arg Leu
1               5

<210> SEQ ID NO 2
<211> LENGTH: 6
<212> TYPE: PRT
<213> ORGANISM: Newcastle disease virus
```

```
<400> SEQUENCE: 2

Arg Arg Gln Lys Arg Leu
1               5

<210> SEQ ID NO 3
<211> LENGTH: 6
<212> TYPE: PRT
<213> ORGANISM: Newcastle disease virus

<400> SEQUENCE: 3

Arg Arg Arg Arg Arg Leu
1               5

<210> SEQ ID NO 4
<211> LENGTH: 6
<212> TYPE: PRT
<213> ORGANISM: Newcastle disease virus

<400> SEQUENCE: 4

Arg Arg Gln Arg Arg Phe
1               5

<210> SEQ ID NO 5
<211> LENGTH: 6
<212> TYPE: PRT
<213> ORGANISM: Newcastle disease virus

<400> SEQUENCE: 5

Lys Lys Arg Lys Arg Leu
1               5

<210> SEQ ID NO 6
<211> LENGTH: 18
<212> TYPE: DNA
<213> ORGANISM: Bacteriophage T7

<400> SEQUENCE: 6
taatacgact actatagg                                               18

<210> SEQ ID NO 7
<211> LENGTH: 24
<212> TYPE: DNA
<213> ORGANISM: Bacteriophage T7

<400> SEQUENCE: 7
taaacgggtc ttgaggggtt tttt                                        24

<210> SEQ ID NO 8
<211> LENGTH: 106
<212> TYPE: DNA
<213> ORGANISM: Hepatitis D virus

<400> SEQUENCE: 8
cccagccgta ccgttctcca cctcctcgcg gtccgacctg ggcatccgaa ggaggacgca   60
cgtccactcg gatggctaag ggagtagcat aaccccttgg ggcctc                106

<210> SEQ ID NO 9
<211> LENGTH: 62
<212> TYPE: DNA
<213> ORGANISM: Artificial Sequence
<220> FEATURE:
<223> OTHER INFORMATION: Synthesized
```

```
<400> SEQUENCE: 9
aattcttttc gccggcgtgg ccggccttta attaatcctg caggtcttaa gtgcgatcgc    60
ta                                                                  62

<210> SEQ ID NO 10
<211> LENGTH: 62
<212> TYPE: DNA
<213> ORGANISM: Artificial Sequence
<220> FEATURE:
<223> OTHER INFORMATION: Synthesized

<400> SEQUENCE: 10
agcttagcga tcgcacttaa gacctgcagg attaattaaa ggccggccac gccggcgaaa    60
ag                                                                  62

<210> SEQ ID NO 11
<211> LENGTH: 3242
<212> TYPE: DNA
<213> ORGANISM: Artificial Sequence
<220> FEATURE:
<223> OTHER INFORMATION: Synthesized

<400> SEQUENCE: 11
cgccggcgta atacgactca ctatagggac caaacagaga atccgtgagt tacgataaaa    60
ggcgaaggag caattgaagt cgcacgggta gaaggtgtga atctcgagtg cgagcccgaa   120
gcacaaactc gagaaagcct tctgccaaca tgtcttccgt atttgatgag tacgaacagc   180
tcctcgcggc tcagactcgc cccaatggag ctcatggagg gggagaaaaa gggagtacct   240
taaaagtaga cgtcccggta ttcactctta acagtgatga cccagaagat agatggagct   300
ttgtggtatt ctgcctccgg attgctgtta gcgaagatgc caacaaacca ctcaggcaag   360
gtgctctcat atctctttta tgctcccact cacaggtaat gaggaaccat gttgccattg   420
cagggaaaca gaatgaagcc acattggccg tgcttgagat tgatggcttt gccaacggca   480
cgccccagtt caacaatagg agtggagtgt ctgaagagag agcacagaga tttgcgatga   540
tagcaggatc tctcccctcg gcatgcagca acggaacccc gttcgtcaca gccggggcag   600
aagatgatgc accagaagac atcaccgata ccctggagag gatcctctct atccaggctc   660
aagtatgggt cacagtagca aaagccatga ctgcgtatga gactgcagat gagtcggaaa   720
caaggcgaat caataagtat atgcagcaag gcagggtcca aaagaaatac atcctctacc   780
ccgtatgcag gagcacaatc caactcacga tcagacagtc tcttgcagtc cgcatctttt   840
tggttagcga gctcaagaga ggccgcaaca cggcaggtgg tacctctact tattataacc   900
tggtagggga cgtagactca tacatcagga ataccgggct tactgcattc ttcttgacac   960
tcaagtacgg aatcaacacc aagacatcag cccttgcact tagtagcctc tcaggcgaca  1020
tccagaagat gaagcagctc atgcgtttgt atcggatgaa aggagataat gcgccgtaca  1080
tgacattact tggtgatagt gaccagatga gctttgcgcc tgccgagtat gcacaacttt  1140
actcctttgc catgggtatg gcatcagtcc tagataaagg tactgggaaa taccaatttg  1200
ccagggactt tatgagcaca tcattctgga gacttggagt agagtacgct caggctcagg  1260
gaagtagcat taacgaggat atggctgccg agctaaagct aaccccagca gcaatgaagg  1320
gcctggcagc tgctgcccaa cgggtctccg acgataccag cagcatatac atgcctactc  1380
aacaagtcgg agtcctcact gggcttagcg agggggggtc ccaagctcta caaggcgat   1440 cgaatagatc gcaagggcaa ccagaagccg gggatgggga gacccaattc ctggatctga  1500
```

```
tgagagcggt agcaaatagc atgagggagg cgccaaactc tgcacagggc actccccaat    1560
cggggcctcc cccaactcct gggccatccc aagataacga caccgactgg gggtattgat    1620
ggacaaaacc cagcctgctt ccacaaaaac atcccaatgc cctcacccgt agtcgacccc    1680
tcgatttgcg gctctatatg accacaccct caaacaaaca tcccctctt tcctccctcc     1740 ccctgctgta caactcggcg cgccctagat accacaggca caatgcggct cactaacaat    1800
caaaacagag ccgagggaat tagaaaaaag tacgggtaga agagggatat tcagagatca    1860
gggcaagtct cccgagtctc tgctctctcc tctacctgat agaccaggac aaacatggcc    1920
acctttacag atgcagagat cgacgagcta tttgagacaa gtggaactgt cattgacaac    1980
ataattacag cccagggtaa accagcagag actgttggaa ggagtgcaat cccacaaggc    2040
aagaccaagg tgctgagcgc agcatgggag aagcatggga gcatccagcc accggccagt    2100
caagacaacc ccgatcgaca ggacagatct gacaaacaac catccacacc cgagcaaacg    2160
accccgcatg acagcccgcc ggccacatcc gccgaccagc cccccaccca ggccacagac    2220
gaagccgtcg acacacagtt caggaccgga gcaagcaact ctctgctgtt gatgcttgac    2280
aagctcagca taaatcgtc caatgctaaa aagggcccat ggtcgagccc caagaggggg     2340
aatcaccaac gtccgactca acagcagggg agtcaaccca gtcgcggaaa cagtcaggaa    2400
agaccgcaga accaagtcaa ggccgcccct ggaaaccagg gcacagacgt gaacacagca    2460
tatcatggac aatgggagga gtcacaacta tcagctggtg caacccctca tgctctccga    2520
tcaaggcaga gccaagacaa tacccttgta tctgcggatc atgtccagcc acctgtagac    2580
tttgtgcaag cgatgatgtc tatgatggag gcgatatcac agagagtaag taaggttgac    2640
tatcagctag atcttgtctt gaaacagaca tcctccatcc ctatgatgcg gtccgaaatc    2700
caacagctga aaacatctgt tgcagtcatg gaagccaact tgggaatgat gaagattctg    2760
gatcccggtt gtgccaacat ttcatctctg agtgatctac gggcagttgc ccgatctcac    2820
ccggttttag tttcaggccc tggagacccc tctccctatg tgacacaagg aggcgaaatg    2880
gcacttaata aactttcgca accagtgcca catccatctg aattgattaa acccgccact    2940
gcatgcgggc ctgatatagg agtggaaaag gacactgtcc gtgcattgat catgtcacgc    3000
ccaatgcacc cgagttcttc agccaagctc ctaagcaagt tagatgcagc cgggtcgatc    3060
gaggaaatca ggaaaatcaa gcgccttgct ctaaatggct aattactact gccacacgta    3120
gcgggtccct gtccactcgg catcacacgg aatctgcacc gagttccccc ccgcagaccc    3180
aaggtccaac tctccaagcg gcaatcctct ctcgcttcct cagccccact gaatggccgg    3240
cc                                                                   3242
```

<210> SEQ ID NO 12
<211> LENGTH: 2971
<212> TYPE: DNA
<213> ORGANISM: Artificial Sequence
<220> FEATURE:
<223> OTHER INFORMATION: Synthesized

<400> SEQUENCE: 12

```
ggccggccaa ccgtaattaa tctagctaca tttaagatta agaaaaaata cgggtagaat     60
tggagtgccc caattgtgcc aagatggact catctaggac aattgggctg tactttgatt   120
ctgcccattc ttctagcaac ctgttagcat ttccgatcgt cctacaaggc acaggagatg   180
ggaagaagca aatcgccccg caatatagga tccagcgcct tgacttgtgg actgatagta   240
```

-continued

```
aggaggactc agtattcatc accacctatg gattcatctt tcaagttggg aatgaagaag      300
ccactgtcgg catgatcgat gataaaccca agcgcgagtt actttccgct gcgatgctct      360
gcctaggaag cgtcccaaat accggagacc ttattgagct ggcaagggcc tgtctcacta      420
tgatagtcac atgcaagaag agtgcaacta atactgagag aatggttttc tcagtagtgc      480
aggcacccca agtgctgcaa agctgtaggg ttgtggcaaa caaatactca tcagtgaatg      540
cagtcaagca cgtgaaagcg ccagagaaga ttcccgggag tggaacccta gaatacaagg      600
tgaactttgt ctccttgact gtggtaccga agaaggatgt ctacaagatc ccagctgcag      660
tattgaaggt ttctggctcg agtctgtaca atcttgcgct caatgtcact attaatgtgg      720
aggtagaccc gaggagtcct ttggttaaat ctttgtctaa gtctgacagc ggatactatg      780
ctaacctctt cttgcatatt ggacttatga ccaccgtaga taggaagggg aagaaagtga      840
catttgacaa gctggaaaag aaaataagga gccttgatct atctgtcggg ctcagtgatg      900
tgctcgggcc ttccgtgttg gtaaaagcaa gaggtgcacg gactaagctt ttggcacctt      960
tcttctctag cagtgggaca gcctgctatc ccatagcaaa tgcttctcct caggtggcca     1020
agatactctg gagtcaaacc gcgtgcctgc ggagcgttaa aatcattatc caagcaggta     1080
cccaacgcgc tgtcgcagtg accgccgacc acgaggttac ctctactaag ctggagaagg     1140
ggcacaccct tgccaaatac aatccttttta agaaataagc tgcgtctctg agattgcgct     1200
ccgcccactc acccagatca tcatgacaca aaaaactaat ctgtcttgat tatttacagt     1260
tagtttacgc gtctatcaag ttagaaaaaa cacgggtaga agattctgga tcccggttgg     1320
cgccctccag gtgcaagatg ggctccagac cttctaccaa gaacccagca cctatgatgc     1380
tgactatccg ggttgcgctg gtactgagtt gcatctgtcc ggcaaactcc attgatggca     1440
ggcctcttgc agctgcagga attgtggtta caggagacaa agccgtcaac atatacacct     1500
catcccagac aggatcaatc atagttaagc tcctcccgaa tctgcccaag gataaggagg     1560
catgtgcgaa agccccttg gatgcataca acaggacatt gaccactttg ctcacccccc      1620
ttggtgactc tatccgtagg atacaagagt ctgtgactac atctggaggg gggagacagg     1680
ggcgccttat aggcgccatt attggcggtg tggctcttgg ggttgcaact gccgcacaaa     1740
taacagcggc cgcagctctg atacaagcca acaaaatgc tgccaacatc ctccgactta      1800
aagagagcat tgccgcaacc aatgaggctg tgcatgaggt cactgacgga ttatcgcaac     1860
tagcagtggc agttgggaag atgcagcagt tgttaatga ccaatttaat aaaacagctc      1920
aggaattaga ctgcatcaaa attgcacagc aagttggtgt agagctcaac ctgtacctaa     1980
ccgaattgac tacagtattc ggaccacaaa tcacttcacc tgctttaaac aagctgacta     2040
ttcaggcact ttacaatcta gctggtggaa atatggatta cttattgact aagttaggtg     2100
tagggaacaa tcaactcagc tcattaatcg gtagcggctt aatcaccggt aaccctattc     2160
tatacgactc acagactcaa ctcttgggta tacaggtaac tctaccttca gtcgggaacc     2220
taaataatat gcgtgccacc tacttggaaa ccttatccgt aagcacaacc agggatttg      2280 cctcggcact tgtccccaaa gtggtgacac aggtcggttc tgtgatagaa gaacttgaca     2340
cctcatactg tatagaaact gacttagatt tatattgtac aagaatagta acgttcccta     2400
tgtcccctgg tatttattcc tgcttgagcg gcaatacgtc ggcctgtatg tactcaaaga     2460
ccgaaggcgc acttactaca ccatacatga ctatcaaagg ttcagtcatc gccaactgca     2520
agatgacaac atgtagatgt gtaaaccccc cgggtatcat atcgcaaaac tatggagaag     2580
ccgtgtctct aatagataaa caatcatgca atgttttatc cttaggcggg ataactttaa     2640
```

| | |
|---|---|
| ggctcagtgg ggaattcgat gtaacttatc agaagaatat ctcaatacaa gattctcaag | 2700 |
| taataataac aggcaatctt gatatctcaa ctgagcttgg gaatgtcaac aactcgatca | 2760 |
| gtaatgcttt gaataagtta gaggaaagca acagaaaact agacaaagtc aatgtcaaac | 2820 |
| tgactagcac atctgctctc attacctata tcgttttgac tatcatatct cttgttttg | 2880 |
| gtatacttag cctgattcta gcatgctacc taatgtacaa gcaaaggcg caacaaaaga | 2940 |
| ccttattatg gcttgggaat aatactctag a | 2971 |

<210> SEQ ID NO 13
<211> LENGTH: 3092
<212> TYPE: DNA
<213> ORGANISM: Artificial Sequence
<220> FEATURE:
<223> OTHER INFORMATION: Synthesized

<400> SEQUENCE: 13

| | |
|---|---|
| ttaattaagt gaaagttctg gtagtctgtc agttcagaga gttaagaaaa aactaccggt | 60 |
| tgtagatgac caaaggacga tatacgggta gaacggtaag agaggccgcc cctcaattgc | 120 |
| gagccaggct tcacaacctc cgttctaccg cttcaccgac aacagtcctc aatcatggac | 180 |
| cgcgccgtta gccaagttgc gttagagaat gatgaaagag aggcaaaaaa tacatggcgc | 240 |
| ttgatattcc ggattgcaat cttattctta acagtagtga ccttggctat atctgtagcc | 300 |
| tccctttat atagcatggg ggctagcaca cctagcgatc ttgtaggcat accgactagg | 360 |
| atttccaggg cagaagaaaa gattacatct acacttggtt ccaatcaaga tgtagtagat | 420 |
| aggatatata agcaagtggc ccttgagtct ccgttggcat tgttaaatac tgagaccaca | 480 |
| attatgaacg caataacatc tctctcttat cagattaatg gagctgcaaa caacagtggg | 540 |
| tgggggcac ctatccatga cccagattat ataggggga taggcaaaga actcattgta | 600 |
| gatgatgcta gtgatgtcac atcattctat ccctctgcat ttcaagaaca tctgaatttt | 660 |
| atccccggcgc ctactacagg atcaggttgc actcgaatac cctcatttga catgagtgct | 720 |
| acccattact gctacaccca taatgtaata ttgtctggat gcagagatca ctcacattca | 780 |
| tatcagtatt tagcacttgg tgtgctccgg acatctgcaa cagggagggt attcttttct | 840 |
| actctgcgtt ccatcaacct ggacgacacc caaaatcgga agtcttgcag tgtgagtgca | 900 |
| actccctgg gttgtgatat gctgtgctcg aaagtcacgg agacagagga agaagattat | 960 |
| aactcagctg tccctacgcg gatggtacat gggaggttag ggttcgacgg ccagtaccac | 1020 |
| gaaaaggacc tagatgtcac aacattattc ggggactggg tggccaacta cccaggagta | 1080 |
| gggggtggat ctttttattga cagccgcgta tggttctcag tctacggagg gttaaaaccc | 1140 |
| aattcaccca gtgacactgt acaggaaggg aaatatgtga tatacaagcg atacaatgac | 1200 |
| acatgcccag atgagcaaga ctaccagatt cgaatggcca agtcttcgta taagcctgga | 1260 |
| cggtttggtg ggaaacgcat acagcaggct atcttatcta tcaaggtgtc aacatcctta | 1320 |
| ggcgaagacc cggtactgac tgtaccgccc aacacagtca cactcatggg ggccgaaggc | 1380 |
| agaattctca cagtagggac atctcatttc ttgtatcaac gagggtcatc atacttctct | 1440 |
| cccgcgttat tatatcctat gacagtcagc aacaaaacag ccactcttca tagtccttat | 1500 |
| acattcaatg ccttcactcg gccaggtagt atcccttgcc aggcttcagc aagatgcccc | 1560 |
| aactcgtgtg ttactggagt ctatacagat ccatatcccc taatcttcta tagaaaccac | 1620 |
| accttgcgag gggtattcgg gacaatgctt gatggtgtac aagcaagact taaccctgcg | 1680 |

```
tctgcagtat tcgatagcac atcccgcagt cgcattactc gagtgagttc aagcagtacc    1740
aaagcagcat acacaacatc aacttgtttt aaagtggtca agactaataa gacctattgt    1800
ctcagcattg ctgaaatatc taatactctc ttcggagaat tcagaatcgt cccgttacta    1860
gttgagatcc tcaaagatga cggggttaga gaagccaggt ctggctagtt gagtcaatta    1920
taaaggagtt ggaaagatgg cattgtatca cctatcttct gcgacatcaa gaatcaaacc    1980
gaatggccgc gcgggcccga attccatgtt gccagttgac cacaatcagc cagtgctcat    2040
gcgatcagat taagccttgt cattaatctc ttgattaaga aaaaatgtaa gtggcaatga    2100
gatacaaggc aaaacagctc atggtaaata atacgggtag acatggcga gctccggtcc    2160 tgaaagggca gagcatcaga ttatcctacc agagccacac ctgtcttcac cattggtcaa    2220
gcacaaacta ctctattact ggaaattaac tgggctaccg cttcctgatg aatgtgactt    2280
cgaccacctc attctcagcc gacaatggaa aaaaatactt gaatcggcct ctcctgatac    2340
tgagagaatg ataaaactcg gaagggcagt acaccaaact cttaaccaca attccagaat    2400
aaccggagtg ctccacccca ggtgtttaga caactggct aatattgagg tcccagattc    2460
aaccaacaaa tttcggaaga ttgagaagaa gatccaaatt cacaacacga gatatggaga    2520
actgttcaca aggctgtgta cgcatataga gaagaaactg ctggggtcat cttggtctaa    2580
caatgtcccc cggtcagagg agttcagcag cattcgtacg gatccggcat tctggtttca    2640
ctcaaaatgg tccacagcca gtttgcatg gctccatata aaacgatcc agaggcatct    2700 gatggtggca gctaagacaa ggtctgcggc aacaaattg gtgatgctaa cccataaggt    2760
aggccaagtc tttgtcactc ctgaacttgt cgttgtgacg catacgaatg agaacaagtt    2820
cacatgtctt acccaggaac ttgtattgat gtatgcagat atgatggagg cagagatat    2880 ggtcaacata atatcaacca cggcggtgca tctcagaagc ttatcagaga aaattgatga    2940
cattttgcgg ttaatagacg ctctggcaaa agacttgggt aatcaagtct acgatgttgt    3000
atcactaatg gagggatttg catacggagc tgtccagcta ctcgagccgt caggtacatt    3060
tgcaggagat tcttcgcat tcaacctgca gg                                   3092
```

<210> SEQ ID NO 14
<211> LENGTH: 2035
<212> TYPE: DNA
<213> ORGANISM: Artificial Sequence
<220> FEATURE:
<223> OTHER INFORMATION: Synthesized

<400> SEQUENCE: 14

```
cctgcaggag cttaaagaca ttctaattgg cctcctcccc aatgatatag cagaatccgt     60
gactcatgca atcgctactg tattctctgg tttagaacag aatcaagcag ctgagatgtt    120
gtgtctgttg cgtctgtggg gtcacccact gcttgagtcc cgtattgcag caaaggcagt    180
caggagccaa atgtgcgcac cgaaaatggt agactttgat atgatccttc aggtactgtc    240
tttcttcaag ggaacaatca tcaacgggta cagaaagaag aatgcaggtg tgtggccgcg    300
agtcaaagtg gatacaatat atgggaaggt cattgggcaa ctacatgcag attcagcaga    360
gatttcacac gatatcatgt tgagagagta taagagttta tctgcacttg aatttgagcc    420
atgtatagaa tatgacctcg tcaccaacct gagcatgttc taaaagaca aggcaatcgc    480 acaccccaac gataattggc ttgcctcgtt taggcggaac cttctctccg aagaccagaa    540
gaaacatgta aagaagcaa cttcgactaa tcgcctcttg atagagtttt tagagtcaaa    600
tgattttgat ccatataag agatggaata tctgacgacc cttgagtacc ttagagatga    660
```

```
caatgtggca gtatcatact cgctcaagga gaaggaagtg aaagttaatg gacggatctt      720
cgctaagctg acaaagaagt taaggaactg tcaggtgatg gcggaaggga tcctagccga      780
tcagattgca cctttctttc agggaaatgg agtcattcag gatagcatat ccttgaccaa      840
gagtatgcta gcgatgagtc aactgtcttt taacagcaat aagaaacgta tcactgactg      900
taaagaaaga gtatcttcaa accgcaatca tgatccgaaa agcaagaacc gtcggagagt      960
tgcaaccttc ataacaactg acctgcaaaa gtactgtctt aattggagat atcagacaat     1020
caaattgttc gctcatgcca tcaatcagtt gatgggccta cctcacttct cgaatggat      1080 tcacctaaga ctgatggaca ctacgatgtt cgtaggagac cctttcaatc ctccaagtga     1140
ccctactgac tgtgacctct caagagtccc taatgatgac atatatattg tcagtgccag     1200
agggggtatc gaaggattat gccagaagct atggacaatg atctcaattg ctgcaatcca     1260
acttgctgca gctagatcgc attgtcgtgt tgcctgtatg gtacagggtg ataatcaagt     1320
aatagcagta acgagagagg taagatcaga cgactctccg gagatggtgt tgacacagtt     1380
gcatcaagcc agtgataatt tcttcaagga attaattcat gtcaatcatt tgattggcca     1440
taatttgaag gatcgtgaaa ccatcaggtc agacacattc ttcatataca gcaaacgaat     1500
cttcaaagat ggagcaatcc tcagtcaagt cctcaaaaat tcatctaaat tagtgctagt     1560
gtcaggtgat ctcagtgaaa acaccgtaat gtcctgtgcc aacattgcct ctactgtagc     1620
acggctatgc gagaacgggc ttcccaaaga cttctgttac tatttaaact atataatgag     1680
ttgtgtgcag acatactttg actctgagtt ctccatcacc aacaattcgc accccgatct     1740
taatcagtcg tggattgagg catctctttt tgtgcactca tatgttctga ctcctgccca     1800
attaggggga ctgagtaacc ttcaatactc aaggctctac actagaaata tcggtgaccc     1860
ggggactact gcttttgcag agatcaagcg actagaagca gtgggattac tgagtcctaa     1920
cattatgact aatatcttaa ctaggccgcc tgggaatgga gattgggcca gtctgtgcaa     1980
cgacccatac tctttcaatt ttgagactgt tgcaagccca aatattgttc ttaag          2035
```

<210> SEQ ID NO 15
<211> LENGTH: 3975
<212> TYPE: DNA
<213> ORGANISM: Artificial Sequence
<220> FEATURE:
<223> OTHER INFORMATION: Synthesized

<400> SEQUENCE: 15

```
cttaagaaac atacgcaaag agtcctattt gaaacttgtt caaatccctt attgtctgga       60
gtgcacacag aggataatga ggcagaagag aaggcattgg ctgaattctt gcttaatcaa      120
gaggtgattc atccccgcgt tgcgcatgcc atcatggagg caagctctgt aggtaggaga      180
aagcaaattc aagggcttgt tgacacaaca acaccgtaa ttaagattgc gcttactagg       240
aggccattag gcatcaagag gctgatgcgg atagtcaatt attctagcat gcatgcaatg      300
ctgtttagag acgatgtttt ttcctccagt agatccaacc accccttagt ctcttctaat      360
atgtgttctc tgacactggc agactatgca cggaatagaa gctggtcacc tttgacggga      420
ggcaggaaaa tactgggtgt atctaatcct gatacgatag aactcgtaga gggtgagatt      480
cttagtgtaa gcggagggtg tacaagatgt gacagcggag atgaacaatt tacttggttc      540
catcttccaa gcaatataga attgaccgat gacaccagca agaatcctcc gatgagggta      600
ccatatctcg ggtcaaagac acaggagagg agagctgcct cacttgcaaa aatagctcat      660
```

```
atgtcgccac atgtaaaggc tgccctaagg gcatcatccg tgttgatctg ggcttatggg    720
gataatgaag taaattggac tgctgctctt acgattgcaa aatctcggtg taatgtaaac    780
ttagagtatc ttcggttact gtccccttta cccacggctg ggaatcttca acatagacta    840
gatgatggta taactcagat gacattcacc cctgcatctc tctacaggtg tcaccttaca    900
ttcacatatc caatgattct caaaggctgt tcactgaaga aggagtcaaa gaggggaatg    960
tggtttacca acagagtcat gctcttgggt ttatctctaa tcgaatcgat ctttccaatg   1020
acaacaacca ggacatatga tgagatcaca ctgcacctac atagtaaatt tagttgctgt   1080
atcagagaag cacctgttgc ggttcctttc gagctacttg gggtggtacc ggaactgagg   1140
acagtgacct caaataagtt tatgtatgat cctagccctg tatcggaggg agactttgcg   1200
agacttgact tagctatctt caagagttat gagcttaatc tggagtcata tcccacgata   1260
gagctaatga acattctttc aatatccagc gggaagttga ttggccagtc tgtggtttct   1320
tatgatgaag atacctccat aaagaatgac gccataatag tgtatgacaa tacccgaaat   1380
tggatcagtg aagctcagaa ttcagatgtg gtccgcctat ttgaatatgc agcacttgaa   1440
gtgctcctcg actgttctta ccaactctat tacctgagag taagaggcct agacaatatt   1500
gtcttatata tgggtgattt atacaagaat atgccaggaa ttctactttc caacattgca   1560
gctacaatat ctcatcccgt cattcattca aggttacatg cagtgggcct ggtcaaccat   1620
gacggatcac accaacttgc agatacggat tttatcgaaa tgtctgcaaa actattagta   1680
tcttgcaccc gacgtgtgat ctccggctta tattcaggaa ataagtatga tctgctgttc   1740
ccatctgtct tagatgataa cctgaatgag aagatgcttc agctgatatc ccggttatgc   1800
tgtctgtaca cggtactctt tgctacaaca agagaaatcc gaaaataag aggcttaact   1860 gcagaagaga aatgttcaat actcactgag tatttactgt cggatgctgt gaaaccatta   1920
cttagccccg atcaagtgag ctctatcatg tctcctaaca taattacatt cccagctaat   1980
ctgtactaca tgtctcggaa gagcctcaat ttgatcaggg aaagggagga cagggatact   2040
atcctggcgt tgttgttccc ccaagagcca ttattagagt tcccttctgt gcaagatatt   2100
ggtgctcgag tgaaagatcc attcacccga caacctgcgg catttttgca agagttagat   2160
ttgagtgctc cagcaaggta tgacgcattc acacttagtc agattcatcc tgaactcaca   2220
tctccaaatc cggaggaaga ctacttagta cgatacttgt tcagagggat agggactgca   2280
tcttcctctt ggtataaggc atctcatctc ctttctgtac ccgaggtaag atgtgcaaga   2340
cacgggaact ccttatactt agctgaaggg agcggagcca tcatgagtct tctcgaactg   2400
catgtaccac atgaaactat ctattacaat acgctctttt caaatgagat gaaccccccg   2460
caacgacatt tcgggccgac cccaactcag tttttgaatt cggttgttta taggaatcta   2520
caggcggagg taacatgcaa agatggattt gtccaagagt tccgtccatt atggagagaa   2580
aatacagagg aaagtgacct gacctcagat aaagcagtgg ggtatattac atctgcagtg   2640
ccctacagat ctgtatcatt gctgcattgt gacattgaaa ttcctccagg gtccaatcaa   2700
agcttactag atcaactagc tatcaattta tctctgattg ccatgcattc tgtaagggag   2760
ggcggggtag taatcatcaa agtgttgtat gcaatgggat actactttca tctactcatg   2820
aacttgtttg ctccgtgttc cacaaaagga tatattctct ctaatggtta tgcatgtcga   2880
ggagatatgg agtgttacct ggtatttgtc atgggttacc tggcggggcc tacatttgta   2940
catgaggtgg tgaggatggc aaaaactctg gtgcagcggc acggtacgct cttgtctaaa   3000
tcagatgaga tcacactgac caggttattc acctcacagc ggcagcgtgt gacagacatc   3060
```

```
ctatccagtc ctttaccaag attaataaag tacttgagga agaatattga cactgcgctg    3120
attgaagccg ggggacagcc cgtccgtcca ttctgtgcgg agagtctggt gagcacgcta    3180
gcgaacataa ctcagataac ccagattatc gctagtcaca ttgacacagt tatccggtct    3240
gtgatatata tggaagctga gggtgatctc gctgacacag tatttctatt tacccccttac   3300 aatctctcta ctgacgggaa aaagaggaca tcacttatac agtgcacgag acagatccta    3360
gaggttacaa tactaggtct tagagtcgaa aatctcaata aaataggcga tataatcagc    3420
ctagtgctta aaggcatgat ctccatggag gaccttatcc cactaaggac atacttgaag    3480
catagtacct gccctaaata tttgaaggct gtcctaggta ttaccaaact caagaaaatg    3540
tttacagaca cttctgtatt gtacttgact cgtgctcaac aaaaattcta catgaaaact    3600
ataggcaatg cagtcaaagg atattacagt aactgtgact cttaacgaaa atcacatatt    3660
aataggctcc ttttttggcc aattgtattc ttgttgattt aatcatatta tgttagaaaa    3720
aagttgaacc ctgactcctt aggactcgaa ttcgaactca aataaatgtc ttaaaaaaag    3780
gttgcgcaca attattcttg agtgtagtct cgtcattcac caaatctttg tttggtgggt    3840
cggcatggca tctccacctc ctcgcggtcc gacctgggca tccgaaggag gacgcacgtc    3900
cactcggatg gctaagggag tagcataacc ccttggggcc tctaaacggg tcttgagggg    3960 tttttttggcg atcgc                                                    3975

<210> SEQ ID NO 16
<211> LENGTH: 15186
<212> TYPE: DNA
<213> ORGANISM: Artificial Sequence
<220> FEATURE:
<223> OTHER INFORMATION: Synthesized

<400> SEQUENCE: 16
accaaacaga gaatccgtga gttacgataa aaggcgaagg agcaattgaa gtcgcacggg      60
tagaaggtgt gaatctcgag tgcgagcccg aagcacaaac tcgagaaagc cttctgccaa     120
catgtcttcc gtatttgatg agtacgaaca gctcctcgcg gctcagactc gccccaatgg     180
agctcatgga gggggagaaa aagggagtac cttaaaagta gacgtccgg tattcactct     240 taacagtgat gacccagaag atagatggag ctttgtggta ttctgcctcc ggattgctgt     300
tagcgaagat gccaacaaac cactcaggca aggtgctctc atatctcttt tatgctccca     360
ctcacaggta atgaggaacc atgttgccat tgcagggaaa cagaatgaag ccacattggc     420
cgtgcttgag attgatggct tgccaacgca cacgccccag ttcaacaata ggagtggagt     480
gtctgaagag agagcacaga gatttgcgat gatagcagga tctctccctc gggcatgcag     540
caacggaacc ccgttcgtca cagccggggc agaaagatgat gcaccagaag acatcaccga     600
taccctggag aggatcctct ctatccaggc tcaagtatgg gtcacagtag caaaagccat     660
gactgcgtat gagactgcag atgagtcgga acaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg acgtagact catacatcag    900 gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
```

```
gagctttgcg cctgccgagt atgcacaact ttactccttt gccatgggta tggcatcagt    1140
cctagataaa ggtactggga ataccaatt tgccagggac tttatgagca catcattctg     1200
gagacttgga gtagagtacg ctcaggctca gggaagtagc attaacgagg atatggctgc    1260
cgagctaaag ctaaccccag cagcaatgaa gggcctggca gctgctgccc aacgggtctc    1320
cgacgatacc agcagcatat acatgcctac tcaacaagtc ggagtcctca ctgggcttag    1380
cgagggggg tcccaagctc tacaaggcgg atcgaataga tcgcaagggc aaccagaagc     1440
cggggatggg gagacccaat tcctggatct gatgagagcg gtagcaaata gcatgaggga    1500
ggcgccaaac tctgcacagg gcactcccca atcggggcct ccccaactc ctgggccatc     1560
ccaagataac gacaccgact ggggtattg atggacaaaa cccagcctgc ttccacaaaa     1620
acatcccaat gccctcaccc gtagtcgacc cctcgatttg cggctctata tgaccacacc    1680
ctcaaacaaa catccccctc tttcctccct ccccctgctg tacaactcgg cgcgccctag    1740
ataccacagg cacaatgcgg ctcactaaca atcaaaacag agccgaggga attagaaaaa    1800
agtacgggta gaagagggat attcagagat cagggcaagt ctcccgagtc tctgctctct    1860
cctctacctg atagaccagg acaaacatgg ccacctttac agatgcagag atcgacgagc    1920
tatttgagac aagtggaact gtcattgaca acataattac agcccagggt aaaccagcag    1980
agactgttgg aaggagtgca atcccacaag gcaagaccaa ggtgctgagc gcagcatggg    2040
agaagcatgg gagcatccag ccaccggcca gtcaagacaa cccgatcga caggacagat     2100
ctgacaaaca accatccaca cccgagcaaa cgaccccgca tgacagcccg ccggccacat    2160
ccgccgacca gcccccacc caggccacag acgaagccgt cgacacacag ttcaggaccg     2220
gagcaagcaa ctctctgctg ttgatgcttg acaagctcag caataaatcg tccaatgcta    2280
aaaagggccc atggtcgagc ccccaagagg ggaatcacca acgtccgact caacagcagg    2340
ggagtcaacc cagtcgcgga aacagtcagg aaagaccgca gaaccaagtc aaggccgccc    2400
ctggaaacca gggcacagac gtgaacacag catatcatgg acaatgggag gagtcacaac    2460
tatcagctgg tgcaacccct catgctctcc gatcaaggca gagccaagac aatacccttg    2520
tatctgcgga tcatgtccag ccacctgtag actttgtgca agcgatgatg tctatgatgg    2580
aggcgatatc acagagagta agtaaggttg actatcagct agatcttgtc ttgaaacaga    2640
catcctccat ccctatgatg cggtccgaaa tccaacagct gaaaacatct gttgcagtca    2700
tggaagccaa cttgggaatg atgaagattc tggatcccgg ttgtgccaac atttcatctc    2760
tgagtgatct acgggcagtt gcccgatctc accggttttt agtttcaggc cctggagacc    2820
cctctcccta tgtgacacaa ggaggcgaaa tggcacttaa taaactttcg caaccagtgc    2880
cacatccatc tgaattgatt aaacccgcca ctgcatgcgg gcctgatata ggagtggaaa    2940
aggacactgt ccgtgcattg atcatgtcac gcccaatgca cccgagttct tcagccaagc    3000
tcctaagcaa gttagatgca gccgggtcga tcgaggaaat caggaaaatc aagcgccttg    3060
ctctaaatgg ctaattacta ctgccacacg tagcgggtcc ctgtccactc ggcatcacac    3120
ggaatctgca ccgagttccc ccccgcagac ccaaggtcca actctccaag cggcaatcct    3180
ctctcgcttc ctcagcccca ctgaatggcc ggccaaccgt aattaatcta gctacattta    3240
agattaagaa aaaatacggg tagaattgga gtgccccaat tgtgccaaga tggactcatc    3300
taggacaatt gggctgtact ttgattctgc ccattcttct agcaacctgt tagcatttcc    3360
gatcgtccta caaggcacag agatgggaa gaagcaaatc gccccgcaat ataggatcca    3420
gcgccttgac ttgtggactg atagtaagga ggactcagta ttcatcacca cctatggatt    3480
```

```
catctttcaa gttgggaatg aagaagccac tgtcggcatg atcgatgata aacccaagcg    3540
cgagttactt tccgctgcga tgctctgcct aggaagcgtc ccaaataccg agaccttat    3600 tgagctggca agggcctgtc tcactatgat agtcacatgc aagaagagtg caactaatac    3660
tgagagaatg gttttctcag tagtgcaggc accccaagtg ctgcaaagct gtagggttgt    3720
ggcaaacaaa tactcatcag tgaatgcagt caagcacgtg aaagcgccag agaagattcc    3780
cgggagtgga accctagaat acaaggtgaa ctttgtctcc ttgactgtgg taccgaagaa    3840
ggatgtctac aagatcccag ctgcagtatt gaaggtttct ggctcgagtc tgtacaatct    3900
tgcgctcaat gtcactatta atgtggaggt agacccgagg agtcctttgg ttaaatcttt    3960
gtctaagtct gacagcggat actatgctaa cctcttcttg catattggac ttatgaccac    4020
cgtagatagg aaggggaaga aagtgacatt tgacaagctg aaaagaaaaa taaggagcct    4080
tgatctatct gtcgggctca gtgatgtgct cgggccttcc gtgttggtaa aagcaagagg    4140
tgcacggact aagcttttgg cacctttctt ctctagcagt gggacagcct gctatcccat    4200
agcaaatgct tctcctcagg tggccaagat actctggagt caaaccgcgt gcctgcggag    4260
cgttaaaatc attatccaag caggtaccca acgcgctgtc gcagtgaccg ccgaccacga    4320
ggttacctct actaagctgg agaaggggca caccctttgcc aaatacaatc cttttaagaa    4380
ataagctgcg tctctgagat tgcgctccgc ccactcaccc agatcatcat gacacaaaaa    4440
actaatctgt cttgattatt tacagttagt ttacgcgtct atcaagttag aaaaaacacg    4500
ggtagaagat tctggatccc ggttggcgcc ctccaggtgc aagatgggct ccagaccttc    4560
taccaagaac ccagcaccta tgatgctgac tatccgggtt gcgctggtac tgagttgcat    4620
ctgtccggca aactccattg atggcaggcc tcttgcagct gcaggaattg tggttacagg    4680
agacaaagcc gtcaacatat acacctcatc ccagacagga tcaatcatag ttaagctcct    4740
cccgaatctg cccaaggata aggaggcatg tgcgaaagcc cccttggatg catacaacag    4800
gacattgacc actttgctca ccccccttgg tgactctatc cgtaggatac aagagtctgt    4860
gactacatct ggagggggga gacagggcg cctataggc gccattattg gcggtgtggc    4920 tcttgggggtt gcaactgccg cacaaataac agcggccgca gctctgatac aagccaaaca    4980
aaatgctgcc aacatcctcc gacttaaaga gagcattgcc gcaaccaatg aggctgtgca    5040
tgaggtcact gacggattat cgcaactagc agtggcagtt gggaagatgc agcagtttgt    5100
taatgaccaa tttaataaaa cagctcagga attagactgc atcaaaattg cacagcaagt    5160
tggtgtagag ctcaacctgt acctaaccga attgactaca gtattcggac acaaaatcac    5220
ttcacctgct ttaaacaagc tgactattca ggcactttac aatctagctg gtggaaatat    5280
ggattactta ttgactaagt taggtgtagg gaacaatcaa ctcagctcat taatcggtag    5340
cggcttaatc accggtaacc ctattctata cgactcacag actcaactct gggtataca    5400 ggtaactcta ccttcagtcg ggaacctaaa taatatgcgt gccacctact tggaaacctt    5460
atccgtaagc acaaccaggg gatttgcctc ggcacttgtc cccaaagtgg tgacacaggt    5520
cggttctgtg atagaagaac ttgacacctc atactgtata gaaactgact tagatttata    5580
ttgtacaaga atagtaacgt tccctatgtc ccctggtatt tattcctgct tgagcggcaa    5640
tacgtcggcc tgtatgtact caaagaccga aggcgcactt actacaccat acatgactat    5700
caaaggttca gtcatcgcca actgcaagat gacaacatgt agatgtgtaa acccccggg    5760 tatcatatcg caaaactatg gagaagccgt gtctctaata gataaacaat catgcaatgt    5820
```

```
tttatcctta ggcgggataa cttttaaggct cagtggggaa ttcgatgtaa cttatcagaa    5880
gaatatctca atacaagatt ctcaagtaat aataacaggc aatcttgata tctcaactga    5940
gcttgggaat gtcaacaact cgatcagtaa tgctttgaat aagttagagg aaagcaacag    6000
aaaactagac aaagtcaatg tcaaactgac tagcacatct gctctcatta cctatatcgt    6060
tttgactatc atatctcttg tttttggtat acttagcctg attctagcat gctacctaat    6120
gtacaagcaa aaggcgcaac aaaagacctt attatggctt gggaataata ctctagatca    6180
gatgagagcc actacaaaaa tgtgaacaca gatgaggaac gaaggtttcc ctaatagtta    6240
attaagtgaa agttctggta gtctgtcagt tcagagagtt aagaaaaaac taccggttgt    6300
agatgaccaa aggacgatat acgggtagaa cggtaagaga ggccgcccct caattgcgag    6360
ccaggcttca caacctccgt tctaccgctt caccgacaac agtcctcaat catgaccgc    6420 gccgttagcc aagttgcgtt agagaatgat gaaagagagg caaaaaatac atggcgcttg    6480
atattccgga ttgcaatctt attcttaaca gtagtgacct tggctatatc tgtagcctcc    6540
cttttatata gcatgggggc tagcacacct agcgatcttg taggcatacc gactaggatt    6600
tccagggcag aagaaaagat tacatctaca cttggttcca atcaagatgt agtagatagg    6660
atatataagc aagtggccct tgagtctccg ttggcattgt taaatactga ccacaatt    6720 atgaacgcaa taacatctct ctcttatcag attaatggag ctgcaaacaa cagtgggtgg    6780
ggggcaccta tccatgaccc agattatata ggggggatag gcaaagaact cattgtagat    6840
gatgctagtg atgtcacatc attctatccc tctgcatttc aagaacatct gaattttatc    6900
ccggcgccta ctacaggatc aggttgcact cgaatacct catttgacat gagtgctacc    6960
cattactgct acacccataa tgtaatattg tctggatgca gagatcactc acattcatat    7020
cagtatttag cacttggtgt gctccggaca tctgcaacag ggagggtatt cttttctact    7080
ctgcgttcca tcaacctgga cgacacccaa aatcggaagt cttgcagtgt gagtgcaact    7140
cccctgggtt gtgatatgct gtgctcgaaa gtcacggaga cagaggaaga agattataac    7200
tcagctgtcc ctacgcggat ggtacatggg aggttagggt tcgacggcca gtaccacgaa    7260
aaggacctag atgtcacaac attattcggg gactgggtgg ccaactaccc aggagtaggg    7320
ggtggatctt ttattgacag ccgcgtatgg ttctcagtct acggagggtt aaaacccaat    7380
tcacccagtg acactgtaca ggaagggaaa tatgtgatat acaagcgata caatgacaca    7440
tgcccagatg agcaagacta ccagattcga atggccaagt cttcgtataa gcctggacgg    7500
tttggtggga aacgcataca gcaggctatc ttatctatca aggtgtcaac atccttaggc    7560
gaagacccgg tactgactgt accgcccaac acagtcacac tcatgggggc cgaaggcaga    7620
attctcacag tagggacatc tcatttcttg tatcaacgag ggtcatcata cttctctccc    7680
gcgttattat atcctatgac agtcagcaac aaaacagcca ctcttcatag tccttataca    7740
ttcaatgcct tcactcggcc aggtagtatc ccttgccagg cttcagcaag atgcccaac    7800 tcgtgtgtta ctggagtcta tacagatcca tatcccctaa tcttctatag aaaccacacc    7860
ttgcgagggg tattcgggac aatgcttgat ggtgtacaag caagacttaa ccctgcgtct    7920
gcagtattcg atagcacatc ccgcagtcgc attactcgag tgagttcaag cagtaccaaa    7980
gcagcataca caacatcaac ttgttttaaa gtggtcaaga ctaataagac ctattgtctc    8040
agcattgctg aaatatctaa tactctcttc ggagaattca gaatcgtccc gttactagtt    8100
gagatcctca aagatgacgg ggttagagaa gccaggtctg gctagttgag tcaattataa    8160
aggagttgga aagatggcat tgtatcacct atcttctgcg acatcaagaa tcaaaccgaa    8220
```

```
tggccgcgcg ggcccgaatt ccatgttgcc agttgaccac aatcagccag tgctcatgcg    8280
atcagattaa gccttgtcat taatctcttg attaagaaaa aatgtaagtg gcaatgagat    8340
acaaggcaaa acagctcatg gtaaataata cgggtaggac atggcgagct ccggtcctga    8400
aagggcagag catcagatta tcctaccaga gccacacctg tcttcaccat tggtcaagca    8460
caaactactc tattactgga aattaactgg gctaccgctt cctgatgaat gtgacttcga    8520
ccacctcatt ctcagccgac aatggaaaaa aatacttgaa tcggcctctc ctgatactga    8580
gagaatgata aaactcggaa gggcagtaca ccaaactctt aaccacaatt ccagaataac    8640
cggagtgctc caccccaggt gtttagaaca actggctaat attgaggtcc cagattcaac    8700
caacaaattt cggaagattg agaagaagat ccaaattcac aacacgagat atggagaact    8760
gttcacaagg ctgtgtacgc atatagagaa gaaactgctg gggtcatctt ggtctaacaa    8820
tgtcccccgg tcagaggagt tcagcagcat tcgtacggat ccggcattct ggtttcactc    8880
aaaatggtcc acagccaagt ttgcatggct ccatataaaa cagatccaga ggcatctgat    8940
ggtggcagct aagacaaggt ctgcggccaa caaattggtg atgctaaccc ataaggtagg    9000
ccaagtcttt gtcactcctg aacttgtcgt tgtgacgcat acgaatgaga acaagttcac    9060
atgtcttacc caggaacttg tattgatgta tgcagatatg atggagggca gagatatggt    9120
caacataata tcaaccacgg cggtgcatct cagaagctta tcagagaaaa ttgatgacat    9180
tttgcggtta atagacgctc tggcaaaaga cttgggtaat caagtctacg atgttgtatc    9240
actaatggag ggatttgcat acggagctgt ccagctactc gagccgtcag gtacatttgc    9300
aggagatttc ttcgcattca acctgcagga gcttaaagac attctaattg gcctcctccc    9360
caatgatata gcagaatccg tgactcatgc aatcgctact gtattctctg gtttagaaca    9420
gaatcaagca gctgagatgt tgtgtctgtt gcgtctgtgg ggtcacccac tgcttgagtc    9480
ccgtattgca gcaaaggcag tcaggagcca aatgtgcgca ccgaaaatgg tagactttga    9540
tatgatcctt caggtactgt ctttcttcaa gggaacaatc atcaacgggt acagaaagaa    9600
gaatgcaggt gtgtggccgc gagtcaaagt ggatacaata tatgggaagg tcattgggca    9660
actacatgca gattcagcag agatttcaca cgatatcatg ttgagagagt ataagagttt    9720
atctgcactt gaatttgagc catgtataga atatgaccct gtcaccaacc tgagcatgtt    9780
cctaaaagac aaggcaatcg cacacccccaa cgataattgg cttgcctcgt ttaggcggaa    9840
ccttctctcc gaagaccaga agaaacatgt aaaagaagca acttcgacta atcgcctctt    9900
gatagagttt ttagagtcaa atgattttga tccatataaa gagatggaat atctgacgac    9960
ccttgagtac cttagagatg acaatgtggc agtatcatac tcgctcaagg agaaggaagt   10020
gaaagttaat ggacggatct tcgctaagct gacaaagaag ttaaggaact gtcaggtgat   10080
ggcggaaggg atcctagccg atcagattgc accttctttt cagggaaatg gagtcattca   10140
ggatagcata tccttgacca agagtatgct agcgatgagt caactgtctt ttaacagcaa   10200
taagaaacgt atcactgact gtaaagaaag agtatcttca aaccgcaatc atgatccgaa   10260
aagcaagaac cgtcggagag ttgcaaccct cataacaact gacctgcaaa agtactgtct   10320
taattggaga tatcagacaa tcaaattgtt cgctcatgcc atcaatcagt tgatgggcct   10380
acctcacttc ttcgaatgga ttcacctaag actgatggac actacgatgt tcgtaggaga   10440 cccttttcaat cctccaagtg accctactga ctgtgacctc tcaagagtcc ctaatgatga   10500
catatatatt gtcagtgcca gaggggggtat cgaaggatta tgccagaagc tatggacaat   10560
```

```
gatctcaatt gctgcaatcc aacttgctgc agctagatcg cattgtcgtg ttgcctgtat    10620
ggtacagggt gataatcaag taatagcagt aacgagagag gtaagatcag acgactctcc    10680
ggagatggtg ttgacacagt tgcatcaagc cagtgataat ttcttcaagg aattaattca    10740
tgtcaatcat ttgattggcc ataatttgaa ggatcgtgaa accatcaggt cagacacatt    10800
cttcatatac agcaaacgaa tcttcaaaga tggagcaatc ctcagtcaag tcctcaaaaa    10860
ttcatctaaa ttagtgctag tgtcaggtga tctcagtgaa acaccgtaa tgtcctgtgc     10920 caacattgcc tctactgtag cacggctatg cgagaacggg cttcccaaag acttctgtta    10980
ctatttaaac tatataatga gttgtgtgca gacatacttt gactctgagt tctccatcac    11040
caacaattcg caccccgatc ttaatcagtc gtggattgag gacatctctt ttgtgcactc    11100
atatgttctg actcctgccc aattagggg actgagtaac cttaatact caaggctcta     11160 cactagaaat atcggtgacc cggggactac tgcttttgca gagatcaagc gactagaagc    11220
agtgggatta ctgagtccta acattatgac taatatctta actaggccgc ctgggaatgg    11280
agattgggcc agtctgtgca acgacccata ctctttcaat tttgagactg ttgcaagccc    11340
aaatattgtt cttaagaaac atacgcaaag agtcctattt gaaacttgtt caaatccctt    11400
attgtctgga gtgcacacag aggataatga ggcagaagag aaggcattgg ctgaattctt    11460
gcttaatcaa gaggtgattc atccccgcgt tgcgcatgcc atcatggagg caagctctgt    11520
aggtaggaga aagcaaattc aagggcttgt tgacacaaca aacaccgtaa ttaagattgc    11580
gcttactagg aggccattag gcatcaagag gctgatgcgg atagtcaatt attctagcat    11640
gcatgcaatg ctgtttagag acgatgtttt ttcctccagt agatccaacc acccttagt     11700 ctcttctaat atgtgttctc tgacactggc agactatgca cggaatagaa gctggtcacc    11760
tttgacggga ggcaggaaaa tactgggtgt atctaatcct gatacgatag aactcgtaga    11820
gggtgagatt cttagtgtaa gcggagggtg tacaagatgt gacagcggag atgaacaatt    11880
tacttggttc catcttccaa gcaatataga attgaccgat gacaccagca agaatcctcc    11940
gatgagggta ccatatctcg ggtcaaagac acaggagagg agagctgcct cacttgcaaa    12000
aatagctcat atgtcgccac atgtaaaggc tgccctaagg gcatcatccg tgttgatctg    12060
ggcttatggg gataatgaag taaattggac tgctgctctt acgattgcaa aatctcggtg    12120
taatgtaaac ttagagtatc ttcggttact gtccccttta cccacggctg gaatcttca    12180 acatagacta gatgatggta taactcagat gacattcacc cctgcatctc tctacagggt    12240
gtcaccttac attcacatat ccaatgattc tcaaaggctg ttcactgaag aaggagtcaa    12300
agaggggaat gtggtttacc aacagatcat gctcttgggt ttatctctaa tcgaatcgat    12360
ctttccaatg acaacaacca ggacatatga tgagatcaca ctgcacctac atagtaaatt    12420
tagttgctgt atcagagaag cacctgttgc ggttcctttc gagctacttg gggtggtacc    12480
ggaactgagg acagtgacct caaataagtt tatgtatgat cctagccctg tatcggaggg    12540
agactttgcg agacttgact tagctatctt caagagttat gagcttaatc tggagtcata    12600
tcccacgata gagctaatga acattctttc aatatccagc gggaagttga ttggccagtc    12660
tgtggtttct tatgatgaag ataccctccat aaagaatgac gccataatag tgtatgcaa    12720 tacccgaaat tggatcagtg aagctcagaa ttcagatgtg gtccgcctat ttgaatatgc    12780
agcacttgaa gtgctcctcg actgttctta ccaactctat tacctgagag taagaggcct    12840
agacaatatt gtcttatata tgggtgattt atacaagaat atgccaggaa ttctactttc    12900
caacattgca gctacaatat ctcatcccgt cattcattca aggttacatg cagtgggcct    12960
```

```
ggtcaaccat gacggatcac accaacttgc agatacggat tttatcgaaa tgtctgcaaa  13020
actattagta tcttgcaccc gacgtgtgat ctccggctta tattcaggaa ataagtatga  13080
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
cccagctaat ctgtactaca tgtctcggaa gagcctcaat ttgatcaggg aaagggagga  13380 caggatact atcctggcgt tgttgttccc ccaagagcca ttattagagt tcccttctgt  13440
gcaagatatt ggtgctcgag tgaaagatcc attcacccga caacctgcgg cattttttgca  13500 agagttagat ttgagtgctc cagcaaggta tgacgcattc acacttagtc agattcatcc  13560
tgaactcaca tctccaaatc cggaggaaga ctacttagta cgatacttgt tcagagggat  13620
agggactgca tcttcctctt ggtataaggc atctcatctc ctttctgtac ccgaggtaag  13680
atgtgcaaga cacgggaact ccttatactt agctgaaggg agcggagcca tcatgagtct  13740
tctcgaactg catgtaccac atgaaactat ctattacaat acgctctttt caaatgagat  13800
gaaccccccg caacgacatt tcgggccgac cccaactcag tttttgaatt cggttgttta  13860
taggaatcta caggcggagg taacatgcaa agatggattt gtccaagagt tccgtccatt  13920
atggagagaa aatacagagg aaagtgacct gacctcagat aaagcagtgg ggtatattac  13980
atctgcagtg ccctacagat ctgtatcatt gctgcattgt gacattgaaa ttcctccagg  14040
gtccaatcaa agcttactag atcaactagc tatcaattta tctctgattg ccatgcattc  14100
tgtaagggag ggcggggtag taatcatcaa agtgttgtat gcaatgggat actactttca  14160
tctactcatg aacttgtttg ctccgtgttc cacaaaagga tatattctct ctaatggtta  14220
tgcatgtcga ggagatatgg agtgttacct ggtatttgtc atgggttacc tgggcgggcc  14280
tacatttgta catgaggtgg tgaggatggc aaaaactctg gtgcagcggc acggtacgct  14340
cttgtctaaa tcagatgaga tcacactgac caggttattc acctcacagc ggcagcgtgt  14400
gacagacatc ctatccagtc ctttaccaag attaataaag tacttgagga agaatattga  14460
cactgcgctg attgaagccg ggggacagcc cgtccgtcca ttctgtgcgg agagtctggt  14520
gagcacgcta gcgaacataa ctcagataac ccagattatc gctagtcaca ttgacacagt  14580
tatccggtct gtgatatata tggaagctga gggtgatctc gctgacacag tatttctatt  14640 tacccccttac aatctctcta ctgacgggaa aaagaggaca tcacttatac agtgcacgag  14700
acagatccta gaggttacaa tactaggtct tagagtcgaa aatctcaata aaataggcga  14760
tataatcagc ctagtgctta aaggcatgat ctccatggag gaccttatcc cactaaggac  14820
atacttgaag catagtacct gccctaaata tttgaaggct gtcctaggta ttaccaaact  14880
caaagaaatg tttacagaca cttctgtatt gtacttgact cgtgctcaac aaaaattcta  14940
catgaaaact ataggcaatg cagtcaaagg atattacagt aactgtgact cttaacgaaa  15000
atcacatatt aataggctcc tttttttggcc aattgtattc ttgttgattt aatcatatta  15060
tgttagaaaa aagttgaacc ctgactcctt aggactcgaa ttcgaactca ataaatgtc  15120 ttaaaaaaag gttgcgcaca attattcttg agtgtagtct cgtcattcac caaatctttg  15180
tttggt                                                              15186
```

<210> SEQ ID NO 17

<211> LENGTH: 539
<212> TYPE: PRT
<213> ORGANISM: Unknown
<220> FEATURE:
<223> OTHER INFORMATION: Human metapneumovirus

<400> SEQUENCE: 17

```
Met Ser Trp Lys Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380
```

```
Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
            405                 410                 415

Thr Val Thr Ile Asp Asn Thr Val Tyr Gln Leu Ser Lys Val Glu Gly
        420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535

<210> SEQ ID NO 18
<211> LENGTH: 539
<212> TYPE: PRT
<213> ORGANISM: Unknown
<220> FEATURE:
<223> OTHER INFORMATION: Human metapneumovirus

<400> SEQUENCE: 18

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Ala Ala Ala Ala Val Thr Ala Gly Val Ala Ile Ala Lys Thr Ile
        115                 120                 125

Arg Leu Glu Ser Glu Val Thr Ala Ile Asn Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205
```

```
Asp Asn Ala Gly Ile Thr Pro Ala Ile Ser Leu Asp Leu Met Thr Asp
    210                 215                 220
Ala Glu Leu Ala Arg Ala Val Pro Asn Met Pro Thr Ser Ala Gly Gln
225                 230                 235                 240
Ile Lys Leu Met Leu Glu Asn Arg Ala Met Val Arg Arg Lys Gly Phe
                245                 250                 255
Gly Ile Leu Ile Gly Val Tyr Gly Ser Ser Val Ile Tyr Met Val Gln
                260                 265                 270
Leu Pro Ile Phe Gly Val Ile Asp Thr Pro Cys Trp Ile Val Lys Ala
            275                 280                 285
Ala Pro Ser Cys Ser Glu Lys Lys Gly Asn Tyr Ala Cys Leu Leu Arg
290                 295                 300
Glu Asp Gln Gly Trp Tyr Cys Gln Asn Ala Gly Ser Thr Val Tyr Tyr
305                 310                 315                 320
Pro Asn Glu Lys Asp Cys Glu Thr Arg Gly Asp His Val Phe Cys Asp
                325                 330                 335
Thr Ala Ala Gly Ile Asn Val Ala Glu Gln Ser Lys Glu Cys Asn Ile
                340                 345                 350
Asn Ile Ser Thr Thr Asn Tyr Pro Cys Lys Val Ser Thr Gly Arg His
            355                 360                 365
Pro Ile Ser Met Val Ala Leu Ser Pro Leu Gly Ala Leu Val Ala Cys
370                 375                 380
Tyr Lys Gly Val Ser Cys Ser Ile Gly Ser Asn Arg Val Gly Ile Ile
385                 390                 395                 400
Lys Gln Leu Asn Lys Gly Cys Ser Tyr Ile Thr Asn Gln Asp Ala Asp
                405                 410                 415
Thr Val Thr Ile Asp Asn Thr Val Tyr Gln Leu Ser Lys Val Glu Gly
                420                 425                 430
Glu Gln His Val Ile Lys Gly Arg Pro Val Ser Ser Ser Phe Asp Pro
            435                 440                 445
Ile Lys Phe Pro Glu Asp Gln Phe Asn Val Ala Leu Asp Gln Val Phe
450                 455                 460
Glu Asn Ile Glu Asn Ser Gln Ala Leu Val Asp Gln Ser Asn Arg Ile
465                 470                 475                 480
Leu Ser Ser Ala Glu Lys Gly Asn Thr Gly Phe Ile Ile Val Ile Ile
                485                 490                 495
Leu Ile Ala Val Leu Gly Ser Ser Met Ile Leu Val Ser Ile Phe Ile
            500                 505                 510
Ile Ile Lys Lys Thr Lys Lys Pro Thr Gly Ala Pro Pro Glu Leu Ser
515                 520                 525
Gly Val Thr Asn Asn Gly Phe Ile Pro His Asn
530                 535

<210> SEQ ID NO 19
<211> LENGTH: 539
<212> TYPE: PRT
<213> ORGANISM: Unknown
<220> FEATURE:
<223> OTHER INFORMATION: Human metapneumovirus

<400> SEQUENCE: 19

Met Ser Trp Lys Val Met Ile Ile Ile Ser Leu Leu Ile Thr Pro Gln
1               5                   10                  15
His Gly Leu Lys Glu Ser Tyr Leu Glu Glu Ser Cys Ser Thr Ile Thr
            20                  25                  30
```

```
Glu Gly Tyr Leu Ser Val Leu Arg Thr Gly Trp Tyr Thr Asn Val Phe
         35                  40                  45

Thr Leu Glu Val Gly Asp Val Glu Asn Leu Thr Cys Thr Asp Gly Pro
 50                  55                  60

Ser Leu Ile Lys Thr Glu Leu Asp Leu Thr Lys Ser Ala Leu Arg Glu
 65                  70                  75                  80

Leu Lys Thr Val Ser Ala Asp Gln Leu Ala Arg Glu Glu Gln Ile Glu
                 85                  90                  95

Asn Pro Arg Gln Ser Arg Phe Val Leu Gly Ala Ile Ala Leu Gly Val
             100                 105                 110

Ala Thr Ala Ala Ala Val Thr Ala Gly Ile Ala Ile Ala Lys Thr Ile
             115                 120                 125

Arg Leu Glu Ser Glu Val Asn Ala Ile Lys Gly Ala Leu Lys Gln Thr
         130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                 165                 170                 175

Ile Asn Arg Asn Lys Cys Asp Ile Ala Asp Leu Lys Met Ala Val Ser
             180                 185                 190

Phe Ser Gln Phe Asn Arg Arg Phe Leu Asn Val Val Arg Gln Phe Ser
         195                 200                 205

Asp Asn Ala Gly Ile Thr Pro Ala Ile Ser Leu Asp Leu Met Thr Asp
210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                 245                 250                 255

Gly Ile Leu Ile Gly Val Tyr Gly Ser Ser Val Ile Tyr Met Val Gln
             260                 265                 270

Leu Pro Ile Phe Gly Val Ile Asp Thr Pro Cys Trp Ile Ile Lys Ala
         275                 280                 285

Ala Pro Ser Cys Ser Glu Lys Asn Gly Asn Tyr Ala Cys Leu Leu Arg
         290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                 325                 330                 335

Thr Ala Ala Gly Ile Asn Val Ala Glu Gln Ser Arg Glu Cys Asn Ile
             340                 345                 350

Asn Ile Ser Thr Thr Asn Tyr Pro Cys Lys Val Ser Thr Gly Arg His
         355                 360                 365

Pro Ile Ser Met Val Ala Leu Ser Pro Leu Gly Ala Leu Val Ala Cys
370                 375                 380

Tyr Lys Gly Val Ser Cys Ser Ile Gly Ser Asn Trp Val Gly Ile Ile
385                 390                 395                 400

Lys Gln Leu Pro Lys Gly Cys Ser Tyr Ile Thr Asn Gln Asp Ala Asp
                 405                 410                 415

Thr Val Thr Ile Asp Asn Thr Val Tyr Gln Leu Ser Lys Val Glu Gly
             420                 425                 430

Glu Gln His Val Ile Lys Gly Arg Pro Val Ser Ser Ser Phe Asp Pro
         435                 440                 445
```

```
Ile Lys Phe Pro Glu Asp Gln Phe Asn Val Ala Leu Asp Gln Val Phe
    450                 455                 460
Glu Ser Ile Glu Asn Ser Gln Ala Leu Val Asp Gln Ser Asn Lys Ile
465                 470                 475                 480
Leu Asn Ser Ala Glu Lys Gly Asn Thr Gly Phe Ile Ile Val Ile
                485                 490                 495
Leu Val Ala Val Leu Gly Leu Thr Met Ile Ser Val Ser Ile Ile Ile
                500                 505                 510
Ile Ile Lys Lys Thr Arg Lys Pro Thr Gly Ala Pro Pro Glu Leu Asn
            515                 520                 525
Gly Val Thr Asn Gly Gly Phe Ile Pro His Ser
530                 535
```

<210> SEQ ID NO 20
<211> LENGTH: 539
<212> TYPE: PRT
<213> ORGANISM: Unknown
<220> FEATURE:
<223> OTHER INFORMATION: Human metapneumovirus

<400> SEQUENCE: 20

```
Met Ser Trp Lys Val Met Ile Ile Ile Ser Leu Leu Ile Thr Pro Gln
1               5                   10                  15
His Gly Leu Lys Glu Ser Tyr Leu Glu Glu Ser Cys Ser Thr Ile Thr
            20                  25                  30
Glu Gly Tyr Leu Ser Val Leu Arg Thr Gly Trp Tyr Thr Asn Val Phe
        35                  40                  45
Thr Leu Glu Val Gly Asp Val Glu Asn Leu Thr Cys Thr Asp Gly Pro
    50                  55                  60
Ser Leu Ile Lys Thr Glu Leu Asp Leu Thr Lys Ser Ala Leu Arg Glu
65                  70                  75                  80
Leu Lys Thr Val Ser Ala Asp Gln Leu Ala Arg Glu Glu Gln Ile Glu
                85                  90                  95
Asn Pro Arg Gln Ser Arg Phe Val Leu Gly Ala Ile Ala Leu Gly Val
            100                 105                 110
Ala Thr Ala Ala Ala Val Thr Ala Gly Ile Ala Ile Ala Lys Thr Ile
        115                 120                 125
Arg Leu Glu Ser Glu Val Asn Ala Ile Lys Gly Ala Leu Lys Thr Thr
    130                 135                 140
Asn Glu Ala Val Ser Thr Leu Gly Asn Gly Val Arg Val Leu Ala Thr
145                 150                 155                 160
Ala Val Arg Glu Leu Lys Glu Phe Val Ser Lys Asn Leu Thr Ser Ala
                165                 170                 175
Ile Asn Lys Asn Lys Cys Asp Ile Ala Asp Leu Lys Met Ala Val Ser
            180                 185                 190
Phe Ser Gln Phe Asn Arg Arg Phe Leu Asn Val Val Arg Gln Phe Ser
        195                 200                 205
Asp Asn Ala Gly Ile Thr Pro Ala Ile Ser Leu Asp Leu Met Asn Asp
    210                 215                 220
Ala Glu Leu Ala Arg Ala Val Ser Tyr Met Pro Thr Ser Ala Gly Gln
225                 230                 235                 240
Ile Lys Leu Met Leu Glu Asn Arg Ala Met Val Arg Arg Lys Gly Phe
                245                 250                 255
Gly Ile Leu Ile Gly Val Tyr Gly Ser Ser Val Ile Tyr Met Val Gln
            260                 265                 270
```

```
Leu Pro Ile Phe Gly Val Ile Asn Thr Pro Cys Trp Ile Lys Ala
            275                 280                 285

Ala Pro Ser Cys Ser Glu Lys Asp Gly Asn Tyr Ala Cys Leu Leu Arg
290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
                340                 345                 350

Asn Ile Ser Thr Thr Asn Tyr Pro Cys Lys Val Ser Thr Gly Arg His
            355                 360                 365

Pro Ile Ser Met Val Ala Leu Ser Pro Leu Gly Ala Leu Val Ala Cys
            370                 375                 380

Tyr Lys Gly Val Ser Cys Ser Thr Gly Ser Asn Gln Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
                420                 425                 430

Glu Gln His Val Ile Lys Gly Arg Pro Val Ser Asn Ser Phe Asp Pro
            435                 440                 445

Ile Arg Phe Pro Glu Asp Gln Phe Asn Val Ala Leu Asp Gln Val Phe
            450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Ile Ile
                485                 490                 495

Leu Ile Ala Val Leu Gly Leu Thr Met Ile Ser Val Ser Ile Ile Ile
                500                 505                 510

Ile Ile Lys Lys Thr Arg Lys Pro Ala Gly Ala Pro Pro Glu Leu Asn
            515                 520                 525

Gly Val Thr Asn Gly Gly Phe Ile Pro His Ser
            530                 535
```

<210> SEQ ID NO 21
<211> LENGTH: 574
<212> TYPE: PRT
<213> ORGANISM: respiratory syncytial virus

<400> SEQUENCE: 21

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110
```

```
Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Met Asp
    435                 440                 445

Thr Val Ser Val Gly Asn Thr Leu Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Ile Met Ile Thr
    515                 520                 525
```

-continued

```
Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560
Lys Asp Gln Leu Ser Gly Ile Asn Asn Ile Ala Phe Ser Asn
                565                 570

<210> SEQ ID NO 22
<211> LENGTH: 254
<212> TYPE: PRT
<213> ORGANISM: Unknown
<220> FEATURE:
<223> OTHER INFORMATION: Human metapneumovirus

<400> SEQUENCE: 22

Met Glu Ser Tyr Leu Val Asp Thr Tyr Gln Gly Ile Pro Tyr Thr Ala
1               5                   10                  15

Ala Val Gln Val Asp Leu Ile Glu Lys Asp Leu Leu Pro Ala Ser Leu
            20                  25                  30

Thr Ile Trp Phe Pro Leu Phe Gln Ala Asn Thr Pro Pro Ala Val Leu
        35                  40                  45

Leu Asp Gln Leu Lys Thr Leu Thr Ile Thr Thr Leu Tyr Ala Ala Ser
    50                  55                  60

Gln Asn Gly Pro Ile Leu Lys Val Asn Ala Ser Ala Gln Gly Ala Ala
65                  70                  75                  80

Met Ser Val Leu Pro Lys Lys Phe Glu Val Asn Ala Thr Val Ala Leu
                85                  90                  95

Asp Glu Tyr Ser Lys Leu Glu Phe Asp Lys Leu Thr Val Cys Glu Val
            100                 105                 110

Lys Thr Val Tyr Leu Thr Thr Met Lys Pro Tyr Gly Met Val Ser Lys
        115                 120                 125

Phe Val Ser Ser Ala Lys Ser Val Gly Lys Lys Thr His Asp Leu Ile
    130                 135                 140

Ala Leu Cys Asp Phe Met Asp Leu Glu Lys Asn Thr Pro Val Thr Ile
145                 150                 155                 160

Pro Ala Phe Ile Lys Ser Val Ser Ile Lys Glu Ser Glu Ser Ala Thr
                165                 170                 175

Val Glu Ala Ala Ile Ser Ser Glu Ala Asp Gln Ala Leu Thr Gln Ala
            180                 185                 190

Lys Ile Ala Pro Tyr Ala Gly Leu Ile Met Ile Met Thr Met Asn Asn
        195                 200                 205

Pro Lys Gly Ile Phe Lys Lys Leu Gly Ala Gly Thr Gln Val Ile Val
    210                 215                 220

Glu Leu Gly Ala Tyr Val Gln Ala Glu Ser Ile Ser Lys Ile Cys Lys
225                 230                 235                 240

Thr Trp Ser His Gln Gly Thr Arg Tyr Val Leu Lys Ser Arg
                245                 250

<210> SEQ ID NO 23
<211> LENGTH: 256
<212> TYPE: PRT
<213> ORGANISM: respiratory syncytial virus

<400> SEQUENCE: 23

Met Glu Thr Tyr Val Asn Lys Leu His Glu Gly Ser Thr Tyr Thr Ala
1               5                   10                  15

Ala Val Gln Tyr Asn Val Leu Glu Lys Asp Asp Asp Pro Ala Ser Leu
```

```
              20                  25                  30
Thr Ile Trp Val Pro Met Phe Gln Ser Ser Met Pro Ala Asp Leu Leu
             35                  40                  45

Ile Lys Glu Leu Ala Asn Val Asn Ile Leu Val Lys Gln Ile Ser Thr
 50                  55                  60

Pro Lys Gly Pro Ser Leu Arg Val Met Ile Asn Ser Arg Ser Ala Val
 65                  70                  75                  80

Leu Ala Gln Met Pro Ser Lys Phe Thr Ile Cys Ala Asn Val Ser Leu
                 85                  90                  95

Asp Glu Arg Ser Lys Leu Ala Tyr Asp Val Thr Thr Pro Cys Glu Ile
            100                 105                 110

Lys Ala Cys Ser Leu Thr Cys Leu Lys Ser Lys Asn Met Leu Thr Thr
        115                 120                 125

Val Lys Asp Leu Thr Met Lys Thr Leu Asn Pro Thr His Asp Ile Ile
    130                 135                 140

Ala Leu Cys Glu Phe Glu Asn Ile Val Thr Ser Lys Lys Val Ile Ile
145                 150                 155                 160

Pro Thr Tyr Leu Arg Ser Ile Ser Val Arg Asn Lys Asp Leu Asn Thr
                165                 170                 175

Leu Glu Asn Ile Thr Thr Thr Glu Phe Lys Asn Ala Ile Thr Asn Ala
            180                 185                 190

Lys Ile Ile Pro Tyr Ser Gly Leu Leu Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Arg Phe Ala Ile Lys Pro Met Glu Asp
                245                 250                 255

<210> SEQ ID NO 24
<211> LENGTH: 4361
<212> TYPE: DNA
<213> ORGANISM: Artificial Sequence
<220> FEATURE:
<223> OTHER INFORMATION: pBR322

<400> SEQUENCE: 24
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg   120
caccgtcacc ctggatgctg taggcatagg cttggttatg ccggtactgc cgggcctctt   180
gcgggatatc gtccattccg acagcatcgc cagtcactat ggcgtgctgc tagcgctata   240
tgcgttgatg caatttctat gcgcacccgt tctcggagca ctgtccgacc gctttggccg   300
ccgcccagtc ctgctcgctt cgctacttgg agccactatc gactacgcga tcatggcgac   360
cacacccgtc ctgtggatcc tctacgccgg acgcatcgtg gccggcatca ccggcgccac   420
aggtgcggtt gctggcgcct atatcgccga catcaccgat ggggaagatc gggctcgcca   480
cttcgggctc atgagcgctt gtttcggcgt gggtatggtg caggccccg tggcggggg    540 actgttgggc gccatctcct tgcatgcacc attccttgcg gcggcggtgc tcaacggcct   600
caacctacta ctgggctgct tcctaatgca ggagtcgcat aagggagagc gtcgaccgat   660
gcccttgaga gccttcaacc cagtcagctc cttccggtgg gcgcggggca tgactatcgt   720
cgccgcactt atgactgtct tctttatcat gcaactcgta ggacaggtgc cggcagcgct   780
```

```
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggcg ccgacgcgc tgggctacgt     960 cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggacccggct aggctggcgg   1500
ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcagcgccc tgcaccatta tgttccggat ctgcatcgca   1680
ggatgctgct ggctaccctg tggaacacct acatctgtat taacgaagcg ctggcattga   1740
ccctgagtga ttttttctctg gtcccgccgc atccataccg ccagttgttt accctcacaa   1800
cgttccagta accgggcatg ttcatcatca gtaacccgta tcgtgagcat cctctctcgt   1860
ttcatcggta tcattacccc catgaacaga aatcccccctt acacggaggc atcagtgacc   1920
aaacaggaaa aaaccgccct taacatggcc cgctttatca gaagccagac attaacgctt   1980
ctggagaaac tcaacgagct ggacgcggat gaacaggcag acatctgtga atcgcttcac   2040
gaccacgctg atgagctttta ccgcagctgc ctcgcgcgtt tcggtgatga cggtgaaaac   2100
ctctgacaca tgcagctccc ggagacggtc acagcttgtc tgtaagcgga tgccgggagc   2160
agacaagccc gtcagggcgc gtcagcgggt gttggcgggt gtcggggcgc agccatgacc   2220
cagtcacgta gcgatagcgg agtgtatact ggcttaacta tgcggcatca gagcagattg   2280
tactgagagt gcaccatatg cggtgtgaaa taccgcacag atgcgtaagg agaaaatacc   2340
gcatcaggcg ctcttccgct tcctcgctca ctgactcgct gcgctcggtc gttcggctgc   2400
ggcgagcggt atcagctcac tcaaaggcgg taatacggtt atccacagaa tcaggggata   2460
acgcaggaaa gaacatgtga gcaaaaggcc agcaaaaggc caggaaccgt aaaaaggccg   2520
cgttgctggc gttttccat aggctccgcc cccctgacga gcatcacaaa atcgacgct   2580 caagtcagag gtggcgaaac ccgacaggac tataaagata ccaggcgttt ccccctggaa   2640
gctccctcgt gcgctctcct gttccgaccc tgccgcttac cggatacctg tccgcctttc   2700
tcccttcggg aagcgtggcg ctttctcata gctcacgctg taggtatctc agttcggtgt   2760
aggtcgttcg ctccaagctg ggctgtgtgc acgaaccccc cgttcagccc gaccgctgcg   2820
ccttatccgg taactatcgt cttgagtcca acccggtaag acacgactta tcgccactgg   2880
cagcagccac tggtaacagg attagcagag cgaggtatgt aggcggtgct acagagttct   2940
tgaagtggtg gcctaactac ggctacacta aaggacagt atttggtatc tgcgctctgc   3000
tgaagccagt taccttcgga aaagagttgg tagctcttg atccggcaaa caaaccaccg   3060
ctggtagcgg tggttttttt gtttgcaagc agcagattac gcgcagaaaa aaaggatctc   3120
```

```
aagaagatcc tttgatcttt tctacggggt ctgacgctca gtggaacgaa aactcacgtt    3180
aagggatttt ggtcatgaga ttatcaaaaa ggatcttcac ctagatcctt ttaaattaaa    3240
aatgaagttt taaatcaatc taaagtatat atgagtaaac ttggtctgac agttaccaat    3300
gcttaatcag tgaggcacct atctcagcga tctgtctatt tcgttcatcc atagttgcct    3360
gactccccgt cgtgtagata actacgatac gggagggctt accatctggc cccagtgctg    3420
caatgatacc gcgagaccca cgctcaccgg ctccagattt atcagcaata aaccagccag    3480
ccggaagggc cgagcgcaga agtggtcctg caactttatc cgcctccatc cagtctatta    3540
attgttgccg ggaagctaga gtaagtagtt cgccagttaa tagtttgcgc aacgttgttg    3600
ccattgctgc aggcatcgtg gtgtcacgct cgtcgtttgg tatggcttca ttcagctccg    3660
gttcccaacg atcaaggcga gttacatgat cccccatgtt gtgcaaaaaa gcggttagct    3720
ccttcggtcc tccgatcgtt gtcagaagta agttggccgc agtgttatca ctcatggtta    3780
tggcagcact gcataattct cttactgtca tgccatccgt aagatgcttt tctgtgactg    3840
gtgagtactc aaccaagtca ttctgagaat agtgtatgcg gcgaccgagt tgctcttgcc    3900
cggcgtcaac acgggataat accgcgccac atagcagaac tttaaaagtg ctcatcattg    3960
gaaaacgttc ttcggggcga aaactctcaa ggatcttacc gctgttgaga tccagttcga    4020
tgtaacccac tcgtgcaccc aactgatctt cagcatcttt tactttcacc agcgtttctg    4080
ggtgagcaaa aacaggaagg caaaatgccg caaaaaaggg aataagggcg acacggaaat    4140
gttgaatact catactcttc cttttcaat attattgaag catttatcag ggttattgtc    4200
tcatgagcgg atacatattt gaatgtattt agaaaaataa acaaataggg gttccgcgca    4260
catttccccg aaaagtgcca cctgacgtct aagaaaccat tattatcatg acattaacct    4320
ataaaaatag gcgtatcacg aggccctttc gtcttcaaga a    4361
```

<210> SEQ ID NO 25
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: I
<220> FEATURE:
<221> NAME/KEY: misc_feature

```
<222> LOCATION: (7)..(7)
<223> OTHER INFORMATION: n is a, c, g, or t
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: modified_base
<222> LOCATION: (19)..(19)
<223> OTHER INFORMATION: I
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: modified_base
<222> LOCATION: (23)..(23)
<223> OTHER INFORMATION: I
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is a, c, g, or t

<400> SEQUENCE: 25
ncncncncnc ncncncncnc ncncnc                                     26
```

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Lys Leu Lys Leu Leu Leu Leu Leu Lys Leu Lys
1               5                   10

<210> SEQ ID NO 27
<211> LENGTH: 1620
<212> TYPE: DNA
<213> ORGANISM: Unknown
<220> FEATURE:
<223> OTHER INFORMATION: Human metapneumovirus

<400> SEQUENCE: 27
atgtcttgga aagtggtgat catttttca ttgttaataa cacctcaaca cggtcttaaa 60
gagagctact tagaagagtc atgtagcact ataactgaag gatatctcag tgttctgagg 120
acaggttggt acaccaatgt ttttacactg gaggtaggcg atgtagagaa ccttacatgt 180
gccgatggac ccagcttaat aaaaacagaa ttagacctga ccaaaagtgc actaagagag 240
ctcagaacag tttctgctga tcaactggca agagaggagc aaattgaaaa tcccagacaa 300
tctagattcg ttctaggagc aatagcactc ggtgttgcaa ctgcagctgc agttacagca 360
ggtgttgcaa ttgccaaaac catccggctt gaaagtgaag taacagcaat taagaatgcc 420
ctcaaaaaga ccaatgaagc agtatctaca ttggggaatg gagttcgtgt gttggcaact 480
gcagtgagag agctgaaaga ttttgtgagc aagaatctaa cacgtgcaat caacaaaaac 540
aagtgcgaca ttgctgacct gaaaatggcc gttagcttca gtcaattcaa cagaaggttc 600
ctaaatgttg tgcggcaatt ttcagacaac gctggaataa caccagcaat atctttggac 660
ttaatgacag atgctgaact agccagagct gtttccaaca tgccaacatc tgcaggacaa 720
ataaaactga tgttggagaa ccgtgcaatg gtaagaagaa aagggttcgg attcctgata 780
ggagtttacg gaagctccgt aatttacatg gtgcaactgc caatctttgg ggttatagac 840
acgccttgct ggatagtaaa agcagcccct tcttgttcag aaaaaaaggg aaactatgct 900
tgcctcttaa gagaagacca aggatggtat tgtcaaaatg cagggtcaac tgtttactac 960
ccaaatgaaa aagactgtga aacaagagga gaccatgtct tttgcgacac agcagcagga 1020
atcaatgttg ctgagcagtc aaaggagtgc aacataaaca tatctactac taattaccca 1080
tgcaaagtta gcacaggaag acatcctatc agtatggttg cactatctcc tcttggggct 1140
ttggttgctt gctacaaggg agtgagctgt tccattggca gcaacagagt agggatcatc 1200
aagcaactga acaaaggctg ctcttatata accaaccaag acgcagacac agtgacaata 1260
gacaacactg tataccagct aagcaaagtt gaaggcgaac agcatgttat aaaaggaagg 1320
ccagtgtcaa gcagctttga cccagtcaag tttcctgaag atcaattcaa tgttgcactt 1380
gaccaagttt tcgagagcat tgagaacagt caggccttgg tggatcaatc aaacagaatc 1440
ctaagcagtg cagagaaagg aaacactggc ttcatcattg taataattct aattgctgtc 1500
cttggctcta ccatgatcct agtgagtgtt tttatcataa taaagaaaac aaagaaaccc 1560
acaggagcac ctccagagct gagtggtgtc acaaacaatg gcttcatacc acataattag 1620

<210> SEQ ID NO 28

<211> LENGTH: 1620
<212> TYPE: DNA
<213> ORGANISM: Artificial Sequence
<220> FEATURE:
<223> OTHER INFORMATION: Synthetic

<400> SEQUENCE: 28

| | | | | | |
|---|---|---|---|---|---|
| atgagctgga | aggtggtcat | catcttcagc | ctgctgatca | cccctcagca | cggcctgaaa | 60 |
| gagagctacc | tggaagagtc | ctgcagcacc | atcaccgagg | gctacctgag | cgtgctgaga | 120 |
| accggctggt | acaccaacgt | gttcaccctg | gaagtgggcg | acgtggaaaa | cctgacctgt | 180 |
| gccgatggac | ccagcctgat | caagaccgag | ctggacctga | caagagcgc | cctgagagag | 240 |
| ctgaggacag | tctctgcaga | tcagctggcc | agagaggaac | agatcgagaa | ccccagacag | 300 |
| agcagattcg | tgctgggagc | tatcgccctg | ggagttgcta | cagctgctgc | tgtgacagct | 360 |
| ggcgtggcca | ttgccaagac | catccggctg | gaaagcgaag | tgaccgccat | caagaacgcc | 420 |
| ctgaaaaaga | ccaacgaggc | cgtgtctacc | ctcggcaatg | cgttagagt | gctggccaca | 480 |
| gccgtgcgcg | agctgaagga | tttcgtgtcc | aagaacctga | ccagggccat | caacaagaac | 540 |
| aagtgcgaca | ttgccgacct | gaagatggcc | gtgtccttca | gccagttcaa | ccggcggttc | 600 |
| ctgaatgtcg | tgcggcagtt | ctctgacaac | gccggcatca | caccagccat | cagcctggat | 660 |
| ctgatgaccg | atgccgaact | ggctagagcc | gtgtccaaca | tgcctacatc | tgccggccag | 720 |
| atcaagctga | tgctggaaaa | cagagccatg | gtccgacgaa | aaggcttcgg | cttttctgatc | 780 |
| ggcgtgtacg | gcagcagcgt | gatctacatg | gtgcagctgc | ctatcttcgg | cgtgatcgac | 840 |
| acccccttgct | ggatcgtgaa | agccgctcct | agctgcagcg | agaagaaggg | caattacgcc | 900 |
| tgcctgctga | gagaggacca | aggctggtac | tgtcagaatg | ccggcagcac | cgtgtactac | 960 |
| cccaacgaga | aggactgcga | gacaagaggc | gaccacgtgt | ctgtgatac | cgccgctgga | 1020 |
| atcaacgtgg | ccgagcagag | caaagagtgc | aacatcaaca | tcagcaccac | aaactacccc | 1080 |
| tgcaaggtgt | ccaccggcag | acaccctatc | agcatggtgg | ctctgtctcc | actgggagcc | 1140 |
| ctggtggctt | gttataaggg | cgtgtcctgt | agcatcggca | gcaacagagt | gggcatcatc | 1200 |
| aagcagctga | caagggctg | ctcctacatc | accaaccagg | acgccgatac | cgtgaccatc | 1260 |
| gacaataccg | tgtatcagct | gagcaaggtg | aaggcgaac | agcacgtgat | caagggcaga | 1320 |
| cctgtgtcca | gcagcttcga | ccccgtgaag | ttccccgagg | accagttcaa | tgtggccctg | 1380 |
| gaccaggtgt | tcgagagcat | cgagaatagc | caggctctgg | tggaccagtc | caaccggatt | 1440 |
| ctgtctagcg | ccgagaaggg | aaacaccggc | ttcatcatcg | tgatcatcct | gatcgccgtg | 1500 |
| ctgggctcca | ccatgatcct | ggtgtccgtg | ttcatcatca | tcaaaaagac | gaagaagccc | 1560 |
| acaggcgccc | ctccagaact | gtctggcgtg | accaacaatg | gcttcatccc | tcacaactag | 1620 |

<210> SEQ ID NO 29
<211> LENGTH: 1620
<212> TYPE: DNA
<213> ORGANISM: Artificial Sequence
<220> FEATURE:
<223> OTHER INFORMATION: Synthetic

<400> SEQUENCE: 29

| | | | | | |
|---|---|---|---|---|---|
| atgtcttgga | aggtggtcat | catctttagc | ctgctgatca | ccccacagca | cggcctgaag | 60 |
| gagagctacc | tggaggagtc | ctgttctacc | atcacagagg | gctacctgtc | cgtgctgaga | 120 |
| accggctggt | atacaaacgt | gttcaccctg | gaggtcggcg | atgtggagaa | tctgacatgc | 180 |
| gccgacggcc | cttccctgat | caagacagag | ctggatctga | ccaagagcgc | cctgagggag | 240 |

```
ctgagaaccg tgtccgccga ccagctggcc agggaggagc agatcgagaa cccaaggcag      300
tctcgctttg tgctgggagc aatcgccctg ggagtggcaa ccgccgccgc cgtgaccgcc      360
ggcgtggcca tcgccaagac aatccgcctg gagtctgagg tgaccgccat caagaacgcc      420
ctgaagaaga caaatgaggc cgtgagcacc ctgggaaacg cgtgcgggt gctggccaca       480 gccgtgagag agctgaagga tttcgtgtcc aagaatctga cccgggccat caacaagaat      540
aagtgtgaca tcgccgatct gaagatggcc gtgagcttct cccagtttaa ccggagattt      600
ctgaatgtgg tgagacagtt ctctgacaac gccggcatca caccagccat cagcctggac      660
ctgatgaccc atgcagagct ggccagggcc gtgtctaaca tgcccacaag cgccggccag      720
atcaagctga tgctggagaa tagggctatg gtgcggagga agggattcgg ctttctgatc      780
ggcgtgtacg gcagctccgt gatctatatg gtgcagctgc ctatctttgg cgtgatcgat      840
acaccatgct ggatcgtgaa ggccgccccc tcttgtagcg agaagaaggg caattacgca      900
tgcctgctga gggaggatca gggatggtat tgtcagaacg ccggctccac cgtgtactat      960
cccaatgaga aggactgtga acaagaggc gaccacgtgt tctgcgatac cgccgccggc     1020
atcaacgtgg cagagcagtc caaggagtgt aacatcaata tctctaccac aaattaccct     1080
tgcaaggtga gcaccggcag gcaccctatc agcatggtgg ccctgtctcc actgggcgcc     1140
ctggtggcct gctataaggg cgtgtcctgt tctatcggct ccaaccgcgt gggcatcatc     1200
aagcagctga caagggctg ctcttacatc acaaatcagg acgccgatac cgtgacaatc      1260
gataataccg tgtatcagct gtccaaggtg gagggagagc agcacgtgat caagggacgg     1320
cccgtgtcta gctccttcga cccagtgaag tttcccgagg atcagttcaa cgtggccctg     1380
gaccaggtgt ttgagagcat cgagaactcc caggccctgg tggaccagag caatagaatc     1440
ctgagcagcg ccgagaaggg caatacaggc tttatcatcg tgatcatcct gatcgccgtg     1500
ctgggcagca ccatgatcct ggtgtccgtg ttcatcatca tcaagaagac aaagaagcca     1560
accggcgccc ctcctgagct gagcggcgtg accaacaatg gcttcatccc tcacaactag     1620
```

<210> SEQ ID NO 30
<211> LENGTH: 1620
<212> TYPE: DNA
<213> ORGANISM: Artificial Sequence
<220> FEATURE:
<223> OTHER INFORMATION: Synthetic

<400> SEQUENCE: 30

```
atgtcgtgga aggtcgtcat catcttctcg ctgctgatca cgccgcagca cggcctgaaa       60
gagtcgtacc tcgaagagtc gtgctcgacg atcacggagg ctacctgtc ggtgctgcgg       120 acgggctggt acacgaacgt gttcacgctc gaagtcggcg acgtcgaaaa cctgacgtgc      180
gcggacggac cgtcgctgat caagacggag ctcgacctga cgaagtcggc gctgcgcgag      240
ctgcggacgt tctcggcgga tcagctcgcg cgcgaggaac agatcgagaa cccgcggcag      300
tcgcggttcg tgctcggcgc gatcgcgctc ggcgtcgcga cggcggcggc ggtgacggcg      360
ggcgtcgcga tcgcgaagac gatccggctc gaatcggaag tgacggcgat caagaacgcg      420
ctgaaaaaga cgaacgaggc ggtgtcgacg ctcggcaacg cgttcgcgt gctcgcgacg       480 gcggtgcgcg agctgaagga tttcgtgtcg aagaacctga cgcgcgcgat caacaagaac      540
aagtgcgaca tcgcggacct gaagatggcc gtgtcgttct cgcagttcaa ccggcggttc      600
ctgaacgtcg tgcggcagtt ctcggacaac gcgggcatca cgccggcgat ctcgctcgat      660
```

```
ctgatgacgg acgcggaact cgcgcgcgcg gtgtcgaaca tgccgacgtc ggcgggccag    720
atcaagctga tgctcgaaaa ccgcgcgatg gtccgacgga aaggcttcgg ctttctgatc    780
ggcgtgtacg gctcgtcggt gatctacatg gtgcagctgc cgatcttcgg cgtgatcgac    840
acgccgtgct ggatcgtgaa agcggcgccg tcgtgctcgg agaagaaggg caattacgcg    900
tgcctgctgc gcgaggacca aggctggtac tgtcagaacg cgggctcgac ggtgtactac    960
ccgaacgaga aggactgcga gacgcgcggc gaccacgtgt tctgcgatac ggcggcggga   1020
atcaacgtcg cggagcagtc gaaagagtgc aacatcaaca tctcgacgac gaactacccg   1080
tgcaaggtgt cgacgggccg gcacccgatc tcgatggtcg cgctgtcgcc gctcggcgcg   1140
ctcgtcgcgt gttataaggg cgtgtcgtgt tcgatcggct cgaaccgcgt cggcatcatc   1200
aagcagctga acaagggctg ctcgtacatc acgaaccagg acgcggatac ggtgacgatc   1260
gacaatacgg tgtatcagct gtcgaaggtc gaaggcgaac agcacgtgat caagggccgc   1320
ccggtgtcgt cgtcgttcga cccggtgaag ttcccggagg accagttcaa cgtcgcgctc   1380
gaccaggtgt tcgagtcgat cgagaattcg caggcgctcg tcgaccagtc gaaccggatt   1440
ctgtcgtcgg cggagaaggg aaacacgggc ttcatcatcg tgatcatcct gatcgcggtg   1500
ctcggctcga cgatgatcct cgtgtcggtg ttcatcatca tcaaaaagac gaagaagccg   1560
acgggcgcgc cgccggaact gtcgggcgtg acgaacaacg gcttcatccc gcacaactag   1620
```

<210> SEQ ID NO 31
<211> LENGTH: 1659
<212> TYPE: DNA
<213> ORGANISM: Artificial Sequence
<220> FEATURE:
<223> OTHER INFORMATION: Synthetic

<400> SEQUENCE: 31

```
atgggcagca gacccagcac caagaatccc gctcctatga tgctgaccat cagagtggcc     60
ctggtgctga gctgtatctg ccccgccaat agcctgaaag agagctacct ggaagagtcc    120
tgcagcacca tcaccgaggg ctacctgagc gtgctgagaa ccggctggta caccaacgtg    180 ttcacccctgg aagtgggcga cgtggaaaac ctgacctgtg ccgatggacc cagcctgatc    240
aagaccgagc tggacctgac aaagagcgcc ctgagagagc tgaggacagt ctctgcagat    300
cagctggcca gagaggaaca gatcgagaac cccagacaga gcagattcgt gctgggagct    360
atcgccctgg gagttgctac agctgctgct gtgacagctg gcgtggccat tgccaagacc    420
atccggctgg aaagcgaagt gaccgccatc aagaacgccc tgaaaaagac caacgaggcc    480
gtgtctaccc tcggcaatgg cgttagagtg ctggccacag ccgtgcgcga gctgaaggat    540
ttcgtgtcca agaacctgac cagggccatc aacaagaaca agtgcgacat tgccgacctg    600
aagatggccg tgtccttcag ccagttcaac cggcggttcc tgaatgtcgt gcggcagttc    660
tctgacaacg ccggcatcac accagccatc agcctggatc tgatgaccga tgccgaactg    720
gctagagccg tgtccaacat gcctacatct gccggccaga tcaagctgat gctggaaaac    780
agagccatgg tccgacggaa aggcttcggc tttctgatcg gcgtgtacgg cagcagcgtg    840
atctacatgg tgcagctgcc tatcttcggc gtgatcgaca ccccttgctg gatcgtgaaa    900
gccgctccta gctgcagcga aaagaaaggc aattacgcct gcctgctgag agaggaccaa    960
ggctggtact gtcagaatgc cggcagcacc gtgtactacc ccaacgagaa ggactgcgag   1020
acaagaggcg accacgtgtt ctgtgatacc gccgctggaa tcaacgtggc cgagcagagc   1080
aaagagtgca acatcaacat cagcaccaca aactacccct gcaaggtgtc caccggcaga   1140
```

| | |
|---|---|
| caccctatca gcatggtggc tctgtctcca ctgggagccc tggtggcttg ttataagggc | 1200 |
| gtgtcctgta gcatcggcag caacagagtg ggcatcatca agcagctgaa caagggctgc | 1260 |
| tcctacatca ccaaccagga cgccgatacc gtgaccatcg acaataccgt gtatcagctg | 1320 |
| agcaaggtgg aaggcgaaca gcacgtgatc aagggcagac tgtgtccag cagcttcgac | 1380 |
| cccgtgaagt tccccgagga ccagttcaat gtggccctgg accaggtgtt cgagagcatc | 1440 |
| gagaatagcc aggctctggt ggaccagtcc aaccggattc tgtctagcgc cgagaaggga | 1500 |
| aacaccggct tcatcatcgt gatcatcctg atcgccgtgc tgggctccac catgatcctg | 1560 |
| gtgtccgtgt tcatcatcat caaaaagacg aagaagccca caggcgcccc tccagaactg | 1620 |
| tctggcgtga ccaacaatgg cttcatccct cacaactag | 1659 |

<210> SEQ ID NO 32
<211> LENGTH: 1620
<212> TYPE: DNA
<213> ORGANISM: Artificial Sequence
<220> FEATURE:
<223> OTHER INFORMATION: Synthetic

<400> SEQUENCE: 32

| | |
|---|---|
| atgagctgga aggtggtcat catcttcagc ctgctgatca cccctcagca tggcctgaaa | 60 |
| gagagctacc tggaagagtc ctgcagcacc atcacagagg gctacctgag tgtgctgaga | 120 |
| acaggctggt acaccaatgt gttcaccctg gaagtggggg atgtggaaaa cctgacctgt | 180 |
| gctgatggac ccagcctgat caagacagag ctggacctga caaagagtgc cctgagagag | 240 |
| ctgaggacag tctctgcaga tcagctggcc agagaggaac agattgagaa ccccagacag | 300 |
| agcagatttg tgctgggagc tattgccctg ggagttgcta cagctgctgc tgtgacagct | 360 |
| ggggtggcca ttgccaagac catcagactg gaaagtgaag tgacagccat caagaatgcc | 420 |
| ctgaaaaaga ccaatgaggc tgtgtctacc ctgggcaatg gggttagagt gctgccaca | 480 |
| gctgtgagag agctgaagga ttttgtgtcc aagaacctga ccagggccat caacaagaac | 540 |
| aagtgtgaca ttgctgacct gaagatggct gtgtccttca gccagttcaa cagaagattc | 600 |
| ctgaatgtgg tgagacagtt ctctgacaat gctggcatca caccagccat cagcctggat | 660 |
| ctgatgacag atgctgaact ggctagagct gtgtccaaca tgcctacatc tgctggccag | 720 |
| atcaagctga tgctggaaaa cagagccatg gtcagaagaa aaggctttgg ctttctgatt | 780 |
| ggggtgtatg gcagcagtgt gatctacatg gtgcagctgc ctatctttgg ggtgattgac | 840 |
| accccttgct ggattgtgaa agctgctcct agctgcagtg agaagaaggg caattatgcc | 900 |
| tgcctgctga gagaggacca aggctggtac tgtcagaatg ctggcagcac agtgtactac | 960 |
| cccaatgaga aggactgtga caagagggg accatgtgt tctgtgatac agctgctgga | 1020 |
| atcaatgtgg ctgagcagag caaagagtgc aacatcaaca tcagcaccac aaactacccc | 1080 |
| tgcaaggtgt ccacaggcag acacctatc agcatggtgg ctctgtctcc actgggagcc | 1140 |
| ctggtggctt gttataaggg ggtgtcctgt agcattggca gcaacagagt gggcatcatc | 1200 |
| aagcagctga acaagggctg ctcctacatc accaaccagg atgctgatac agtgaccatt | 1260 |
| gacaatacag tgtatcagct gagcaaggtg gaagggaac agcatgtgat caagggcaga | 1320 |
| cctgtgtcca gcagctttga ccctgtgaag ttccctgagg accagttcaa tgtggccctg | 1380 |
| gaccaggtgt ttgagagcat tgagaatagc caggctctgg tggaccagtc caacagaatt | 1440 |
| ctgtctagtg ctgagaaggg aaacacaggc ttcatcattg tgatcatcct gattgctgtg | 1500 |

-continued

```
ctgggctcca ccatgatcct ggtgagtgtg ttcatcatca tcaaaaagac aaagaagccc   1560
acaggggccc ctccagaact gtctggggtg accaacaatg gcttcatccc tcacaactag   1620

<210> SEQ ID NO 33
<211> LENGTH: 734
<212> TYPE: DNA
<213> ORGANISM: Artificial Sequence
<220> FEATURE:
<223> OTHER INFORMATION: Synthesized

<400> SEQUENCE: 33
catggcgcgc ctaagaaaaa atacgggtag aagccaccat gcccgccatg aagatcgagt     60
gccgcatcac cggcaccctg aacggcgtgg agttcgagct ggtgggcggc ggagagggca    120
cccccgagca gggccgcatg accaacaaga tgaagagcac caaaggcgcc ctgaccttca    180
gcccctacct gctgagccac gtgatgggct acggcttcta ccacttcggc acctacccca    240
gcggctacga gaaccccttc ctgcacgcca tcaacaacgg cggctacacc aacacccgca    300
tcgagaagta cgaggacggc ggcgtgctgc acgtgagctt cagctaccgc tacgaggccg    360
gccgcgtgat cggcgacttc aaggtggtgg gcaccggctt ccccgaggac agcgtgatct    420
tcaccgacaa gatcatccgc agcaacgcca ccgtggagca cctgcacccc atgggcgata    480
acgtgctggt gggcagcttc gcccgcacct tcagcctgcg cgacggcggc tactacagct    540
tcgtggtgga cagccacatg cacttcaaga gcgccatcca ccccagcatc ctgcagaacg    600
ggggccccat gttcgccttc cgccgcgtgg aggagctgca cagcaacacc gagctgggca    660
tcgtggagta ccagcacgcc ttcaagaccc ccatcgcctt cgccagatct cgagctcgat    720
aggggcgcgc cggc                                                      734

<210> SEQ ID NO 34
<211> LENGTH: 894
<212> TYPE: DNA
<213> ORGANISM: Unknown
<220> FEATURE:
<223> OTHER INFORMATION: Human metapneumovirus

<400> SEQUENCE: 34
ggccgcgcgg gccttaatta aacgcgtggc cggccggcgc gcctaagaaa aaatacgggt     60
agaagccacc atggagtcct acctagtaga cacctatcaa ggcattcctt acacagcagc    120
tgttcaagtt gatctaatag aaaaggacct gttacctgca agcctaacaa tatggttccc    180
tttgtttcag gccaacacac caccagcagt gctgctcgat cagctaaaaa ccctgacaat    240
aaccactctg tatgctgcat cacaaaatgg tccaatactc aaagtgaatg catcagccca    300
aggtgcagca atgtctgtac ttcccaaaaa atttgaagtc aatgcgactg tagcactcga    360
tgaatatagc aaactggaat ttgacaaact cacagtctgt gaagtaaaaa cagtttactt    420
aacaaccatg aaaccatacg ggatggtatc aaaatttgtg agctcagcca aatcagttgg    480
caaaaaaaca catgatctaa tcgcactatg tgattttatg gatctagaaa agaacacacc    540
tgttacaata ccagcattca tcaaatcagt ttcaatcaaa gagagtgagt cagctactgt    600
tgaagctgct ataagcagtg aagcagacca agctctaaca caggccaaaa ttgcacctta    660
tgcgggatta attatgatca tgactatgaa caatcccaaa ggcatattca aaaagcttgg    720
agctgggact caagtcatag tagaactagg agcatatgtc caggctgaaa gcataagcaa    780
aatatgcaag acttggagcc atcaagggac aagatatgtc ttgaagtcca gataatagat    840
aatggcgcgc catggccggc cacgcgtaat taattaatat aggccgcgcg ggcc          894
```

<210> SEQ ID NO 35
<211> LENGTH: 750
<212> TYPE: DNA
<213> ORGANISM: Unknown
<220> FEATURE:
<223> OTHER INFORMATION: Cytomegalovirus

<400> SEQUENCE: 35

| | | | | | |
|---|---|---|---|---|---|
| tcaatattgg | ccattagcca | tattattcat | tggttatata | gcataaatca | atattggcta | 60 |
| ttggccattg | catacgttgt | atctatatca | taatatgtac | atttatattg | gctcatgtcc | 120 |
| aatatgaccg | ccatgttggc | attgattatt | gactagttat | taatagtaat | caattacggg | 180 |
| gtcattagtt | catagcccat | atatggagtt | ccgcgttaca | taacttacgg | taaatggccc | 240 |
| gcctggctga | ccgcccaacg | accccgccc | attgacgtca | ataatgacgt | atgttcccat | 300 |
| agtaacgcca | atagggactt | tccattgacg | tcaatgggtg | gagtatttac | ggtaaactgc | 360 |
| ccacttggca | gtacatcaag | tgtatcatat | gccaagtccg | cccctattg | acgtcaatga | 420 |
| cggtaaatgg | cccgcctggc | attatgccca | gtacatgacc | ttacgggact | ttcctacttg | 480 |
| gcagtacatc | tacgtattag | tcatcgctat | taccatggtg | atgcggtttt | ggcagtacac | 540 |
| caatgggcgt | ggatagcggt | ttgactcacg | gggatttcca | agtctccacc | ccattgacgt | 600 |
| caatgggagt | ttgttttggc | accaaaatca | acgggacttt | ccaaaatgtc | gtaacaactg | 660 |
| cgatcgcccg | ccccgttgac | gcaaatgggc | ggtaggcgtg | tacggtggga | ggtctatata | 720 |
| agcagagctc | gtttagtgaa | ccgtcagatc | | | | 750 |

<210> SEQ ID NO 36
<211> LENGTH: 534
<212> TYPE: DNA
<213> ORGANISM: Artificial Sequence
<220> FEATURE:
<223> OTHER INFORMATION: Synthesized

<400> SEQUENCE: 36

| | | | | | |
|---|---|---|---|---|---|
| ggtaccatat | ctcgggtcaa | agacacagga | gaggagagct | gcctcacttg | caaaaatagc | 60 |
| tcatatgtcg | ccacatgtaa | aggctgccct | aagggcatca | tccgtgttga | tctgggctta | 120 |
| tggggataat | gaagtaaatt | ggactgctgc | tcttacgatt | gcaaaatctc | ggtgtaatgt | 180 |
| aaacttagag | tatcttcggt | tactgtcccc | tttaccacg | gctgggaatc | ttcaacatag | 240 |
| actagatgat | ggtataactc | agatgacatt | caccctgca | tctctctaca | gggtgtcacc | 300 |
| ttacattcac | atatccaatg | attctcaaag | gctgttcact | gaagaaggag | tcaaagaggg | 360 |
| gaatgtggtt | taccaacaga | tcatgctctt | gggtttatct | ctaatcgaat | cgatctttcc | 420 |
| aatgacaaca | accaggacat | atgatgagat | cacactgcac | ctacatagta | aatttagttg | 480 |
| ctgtatcaga | gaagcacctg | ttgcggttcc | tttcgagcta | cttggggtgg | tacc | 534 |

<210> SEQ ID NO 37
<211> LENGTH: 1747
<212> TYPE: DNA
<213> ORGANISM: Artificial Sequence
<220> FEATURE:
<223> OTHER INFORMATION: Synthesized

<400> SEQUENCE: 37

| | | | | | |
|---|---|---|---|---|---|
| ggccgcgcgg | gccattaatt | aataatacgc | gtggccggcc | atggcgcgcc | taagaaaaaa | 60 |
| tacgggtaga | agccaccatg | tcttggaaag | tggtgatcat | tttttcattg | ttaataacac | 120 |

| | |
|---|---|
| ctcaacacgg tcttaaagag agctacttag aagagtcatg tagcactata actgaaggat | 180 |
| atctcagtgt tctgaggaca ggttggtaca ccaatgtttt tacactggag gtaggcgatg | 240 |
| tagagaacct tacatgtgcc gatggaccca gcttaataaa aacagaatta gacctgacca | 300 |
| aaagtgcact aagagagctc agaacagttt ctgctgatca actggcaaga gaggagcaaa | 360 |
| ttgaaaatcc cagacaatct agattcgttc taggagcaat agcactcggt gttgcaactg | 420 |
| cagctgcagt tacagcaggt gttgcaattg ccaaaaccat ccggcttgaa agtgaagtaa | 480 |
| cagcaattaa gaatgccctc aaaaagacca atgaagcagt atctacattg gggaatggag | 540 |
| ttcgtgtgtt ggcaactgca gtgagagagc tgaaagattt tgtgagcaag aatctaacac | 600 |
| gtgcaatcaa caaaaacaag tgcgacattg ctgacctgaa aatggccgtt agcttcagtc | 660 |
| aattcaacag aaggttccta aatgttgtgc ggcaattttc agacaacgct ggaataacac | 720 |
| cagcaatatc tttggactta atgacagatg ctgaactagc cagagctgtt tccaacatgc | 780 |
| caacatctgc aggacaaata aaactgatgt tggagaaccg tgcaatggta agaagaaaag | 840 |
| ggttcggatt cctgatagga gtttacggaa gctccgtaat ttacatggtg caactgccaa | 900 |
| tctttggggt tatagacacg ccttgctgga tagtaaaagc agccccttct tgttcagaaa | 960 |
| aaaagggaaa ctatgcttgc ctcttaagag aagaccaagg atggtattgt caaaatgcag | 1020 |
| ggtcaactgt ttactaccca aatgaaaaag actgtgaaac aagaggagac catgtctttt | 1080 |
| gcgacacagc agcaggaatc aatgttgctg agcagtcaaa ggagtgcaac ataaacatat | 1140 |
| ctactactaa ttacccatgc aaagttagca caggaagaca tcctatcagt atggttgcac | 1200 |
| tatctcctct tgggggcttttg gttgcttgct acaagggagt gagctgttcc attggcagca | 1260 |
| acagagtagg gatcatcaag caactgaaca aaggctgctc ttatataacc aaccaagacg | 1320 |
| cagacacagt gacaatagac aacactgtat accagctaag caaagttgaa ggcgaacagc | 1380 |
| atgttataaa aggaaggcca gtgtcaagca gctttgaccc agtcaagttt cctgaagatc | 1440 |
| aattcaatgt tgcacttgac caagtttttcg agagcattga gaacagtcag gccttggtgg | 1500 |
| atcaatcaaa cagaatccta agcagtgcag agaaaggaaa cactggcttc atcattgtaa | 1560 |
| taattctaat tgctgtcctt ggctctacca tgatcctagt gagtgttttt atcataataa | 1620 |
| agaaaacaaa gaaacccaca ggagcacctc cagagctgag tggtgtcaca aacaatggct | 1680 |
| tcataccaca taattagagg cgcgccggcc ggccattaac gcgtttaatt aataggccgc | 1740 |
| gcgggcc | 1747 |

<210> SEQ ID NO 38
<211> LENGTH: 5472
<212> TYPE: DNA
<213> ORGANISM: Artificial Sequence
<220> FEATURE:
<223> OTHER INFORMATION: Synthesized

<400> SEQUENCE: 38

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg ccccctattg acgtcaatga | 420 |

```
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagaatt cacgcgtggt acctctagag tcgacccggg cggccgcttc   1140
cctttagtga gggttaatgc ttcgagcaga catgataaga tacattgatg agtttggaca   1200
aaccacaact agaatgcagt gaaaaaaatg ctttatttgt gaaatttgtg atgctattgc   1260
tttatttgta accattataa gctgcaataa acaagttaac aacaacaatt gcattcattt   1320
tatgtttcag gttcagggggg agatgtggga ggttttttaa agcaagtaaa acctctacaa   1380
atgtggtaaa atccgataag gatcgatccg ggctggcgta atagcgaaga ggcccgcacc   1440
gatcgccctt cccaacagtt gcgcagcctg aatggcgaat ggacgcgccc tgtagcggcg   1500
cattaagcgc ggcgggtgtg gtggttacgc gcagcgtgac cgctacactt gccagcgccc   1560
tagcgcccgc tcctttcgct ttcttccctt cctttctcgc cacgttcgcc ggctttcccc   1620
gtcaagctct aaatcggggg ctccctttag ggttccgatt tagtgcttta cggcacctcg   1680
accccaaaaa acttgattag ggtgatggtt cacgtagtgg gccatcgccc tgatagacgg   1740
tttttcgccc tttgacgttg gagtccacgt tctttaatag tggactcttg ttccaaactg   1800
gaacaacact caaccctatc tcggtctatt cttttgattt ataagggatt ttgccgattt   1860
cggcctattg gttaaaaaat gagctgattt aacaaaaatt taacgcgaat tttaacaaaa   1920
tattaacgct tacaatttcc tgatgcggta ttttctcctt acgcatctgt gcggtatttc   1980
acaccgcata cgcggatctg cgcagcacca tggcctgaaa taacctctga agaggaact   2040 tggttaggta ccttctgagg cggaaagaac cagctgtgga atgtgtgtca gttagggtgt   2100
ggaaagtccc caggctcccc agcaggcaga agtatgcaaa gcatgcatct caattagtca   2160
gcaaccaggt gtggaaagtc cccaggctcc ccagcaggca gaagtatgca aagcatgcat   2220
ctcaattagt cagcaaccat agtcccgccc ctaactccgc ccatcccgcc ctaactccg   2280 cccagttccg cccattctcc gccccatggc tgactaattt ttttattta tgcagaggcc   2340 gaggccgcct cggcctctga ctattccag aagtagtgag gaggcttttt tggaggccta   2400
ggcttttgca aaaagcttga ttcttctgac acaacagtct cgaacttaag gctagagcca   2460
ccatgattga acaagatgga ttgcacgcag gttctccggc cgcttgggtg gagaggctat   2520
tcggctatga ctgggcacaa cagacaatcg gctgctctga tgccgccgtg ttccggctgt   2580
cagcgcaggg gcgcccggtt ctttttgtca agaccgacct gtccggtgcc ctgaatgaac   2640
tgcaggacga ggcagcgcgg ctatcgtggc tggccacgac gggcgttcct tgcgcagctg   2700
tgctcgacgt tgtcactgaa gcgggaaggg actggctgct attgggcgaa gtgccggggc   2760
```

```
aggatctcct gtcatctcac cttgctcctg ccgagaaagt atccatcatg gctgatgcaa    2820
tgcggcggct gcatacgctt gatccggcta cctgcccatt cgaccaccaa gcgaaacatc    2880
gcatcgagcg agcacgtact cggatggaag ccggtcttgt cgatcaggat gatctggacg    2940
aagagcatca ggggctcgcg ccagccgaac tgttcgccag gctcaaggcg cgcatgcccg    3000
acggcgagga tctcgtcgtg acccatggcg atgcctgctt gccgaatatc atggtggaaa    3060
atggccgctt ttctggattc atcgactgtg gccggctggg tgtggcggac cgctatcagg    3120
acatagcgtt ggctacccgt gatattgctg aagagcttgg cggcgaatgg gctgaccgct    3180
tcctcgtgct ttacggtatc gccgctcccg attcgcagcg catcgccttc tatcgccttc    3240
ttgacgagtt cttctgagcg ggactctggg gttcgaaatg accgaccaag cgacgcccaa    3300
cctgccatca cgatggccgc aataaaatat ctttattttc attacatctg tgtgttggtt    3360
ttttgtgtga atcgatagcg ataaggatcc gcgtatggtg cactctcagt acaatctgct    3420
ctgatgccgc atagttaagc cagccccgac acccgccaac accgctgac gcgccctgac    3480 gggcttgtct gctcccggca tccgcttaca gacaagctgt gaccgtctcc gggagctgca    3540
tgtgtcagag gttttcaccg tcatcaccga aacgcgcgag acgaaagggc ctcgtgatac    3600
gcctattttt ataggttaat gtcatgataa taatggtttc ttagacgtca ggtggcactt    3660
ttcggggaaa tgtgcgcgga acccctattt gtttattttt ctaaatacat tcaaatatgt    3720
atccgctcat gagacaataa ccctgataaa tgcttcaata atattgaaaa aggaagagta    3780
tgagtattca acatttccgt gtcgccctta ttcccttttt tgcggcattt tgccttcctg    3840
tttttgctca cccagaaacg ctggtgaaag taaaagatgc tgaagatcag ttgggtgcac    3900
gagtgggtta catcgaactg gatctcaaca gcggtaagat ccttgagagt tttcgccccg    3960
aagaacgttt tccaatgatg agcactttta aagttctgct atgtggcgcg gtattatccc    4020
gtattgacgc cgggcaagag caactcggtc gccgcataca ctattctcag aatgacttgg    4080
ttgagtactc accagtcaca gaaaagcatc ttacggatgg catgacagta agagaattat    4140
gcagtgctgc cataaccatg agtgataaca ctgcggccaa cttacttctg acaacgatcg    4200
gaggaccgaa ggagctaacc gcttttttgc acaacatggg gatcatgta actcgccttg    4260 atcgttggga accggagctg aatgaagcca taccaaacga cgagcgtgac accacgatgc    4320
ctgtagcaat ggcaacaacg ttgcgcaaac tattaactgg cgaactactt actctagctt    4380
cccggcaaca attaatagac tggatggagg cggataaagt tgcaggacca cttctgcgct    4440
cggcccttcc ggctggctgg tttattgctg ataaatctgg agccggtgag cgtgggtctc    4500
gcggtatcat tgcagcactg gggccagatg gtaagccctc ccgtatcgta gttatctaca    4560
cgacggggag tcaggcaact atggatgaac gaaatagaca gatcgctgag ataggtgcct    4620
cactgattaa gcattggtaa ctgtcagacc aagtttactc atatatactt tagattgatt    4680
taaaacttca tttttaattt aaaaggatct aggtgaagat cctttttgat aatctcatga    4740
ccaaaatccc ttaacgtgag ttttcgttcc actgagcgtc agaccccgta gaaaagatca    4800
aaggatcttc ttgagatcct ttttttctgc gcgtaatctg ctgcttgcaa acaaaaaaac    4860
caccgctacc agcggtggtt tgtttgccgg atcaagagct accaactctt tttccgaagg    4920
taactggctt cagcagagcg cagataccaa atactgttct tctagtgtag ccgtagttag    4980
gccaccactt caagaactct gtagcaccgc ctacatacct cgctctgcta atcctgttac    5040
cagtggctgc tgccagtggc gataagtcgt gtcttaccgg gttggactca agacgatagt    5100
taccggataa ggcgcagcgg tcgggctgaa cggggggttc gtgcacacag cccagcttgg    5160
```

-continued

```
agcgaacgac ctacaccgaa ctgagatacc tacagcgtga gctatgagaa agcgccacgc    5220
ttcccgaagg gagaaaggcg gacaggtatc cggtaagcgg cagggtcgga acaggagagc    5280
gcacgaggga gcttccaggg ggaaacgcct ggtatcttta tagtcctgtc gggtttcgcc    5340
acctctgact tgagcgtcga ttttttgtgat gctcgtcagg ggggcggagc ctatggaaaa    5400
acgccagcaa cgcggccttt ttacggttcc tggccttttg ctggcctttt gctcacatgg    5460
ctcgacagat ct                                                        5472
```

<210> SEQ ID NO 39
<211> LENGTH: 2892
<212> TYPE: DNA
<213> ORGANISM: Unknown
<220> FEATURE:
<223> OTHER INFORMATION: Cytomegalovirus Newcastle disease virus

<400> SEQUENCE: 39

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact tcctacttg     480 gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata     720
agcagagctc gtttagtgaa ccgtcagatc actagaagct ttattgcggt agtttatcac     780
agttaaattg ctaacgcagt cagtgcttct gacacaacag tctcgaactt aagctgcagt     840
gactctctta aggtagcctt gcagaagttg gtcgtgaggc actgggcagg taagtatcaa     900
ggttacaaga caggtttaag gagaccaata gaaactgggc ttgtcgagac agagaagact     960
cttgcgtttc tgataggcac ctattggtct tactgacatc cactttgcct ttctctccac    1020
aggtgtccac tcccagttca attacagctc ttaaggctag agtacttaat acgactcact    1080
ataggctagc ctcgagaatt ccgagtgcga gcccgaagca caaactcgag aaagccttct    1140
gccaacatgt cttccgtatt tgatgagtac aacagctcc tcgcggctca gactcgcccc    1200
aatggagctc atggagggg agaaaaaggg agtaccttaa aagtagacgt cccggtattc    1260
actcttaaca gtgatgaccc agaagataga tggagctttg tggtattctg cctccggatt    1320
gctgttagcg aagatgccaa caaccactc aggcaaggtg ctctcatatc tctttatgc    1380 tcccactcac aggtaatgag gaaccatgtt gccattgcag ggaaacagaa tgaagccaca    1440
ttggccgtgc ttgagattga tggctttgcc aacggcacgc cccagttcaa caataggagt    1500
ggagtgtctg aagagagagc acagagattt gcgatgatag caggatctct ccctcgggca    1560
tgcagcaacg gaacccgtt cgtcacagcc ggggcagaag atgatgcacc agaagacatc    1620
accgataccc tggagaggat cctctctatc caggctcaag tatgggtcac agtagcaaaa    1680
```

```
gccatgactg cgtatgagac tgcagatgag tcggaaacaa ggcgaatcaa taagtatatg    1740
cagcaaggca gggtccaaaa gaaatacatc ctctaccccg tatgcaggag cacaatccaa    1800
ctcacgatca gacagtctct tgcagtccgc atcttttcgg ttagcgagct caagagaggc    1860
```
(Note: line 1860 - reading "atctttttgg")
```
ctcacgatca gacagtctct tgcagtccgc atctttttgg ttagcgagct caagagaggc    1860
cgcaacacgg caggtggtac ctctacttat tataacctgg taggggacgt agactcatac    1920
atcaggaata ccgggcttac tgcattcttc ttgacactca agtacggaat caacaccaag    1980
acatcagccc ttgcacttag tagcctctca ggcgacatcc agaagatgaa gcagctcatg    2040
cgtttgtatc ggatgaaagg agataatgcg ccgtacatga cattacttgg tgatagtgac    2100
cagatgagct ttgcgcctgc cgagtatgca caactttact cctttgccat gggtatggca    2160
tcagtcctag ataaaggtac tgggaaatac caatttgcca gggactttat gagcacatca    2220
ttctggagac ttggagtaga gtacgctcag gctcagggaa gtagcattaa cgaggatatg    2280
gctgccgagc taaagctaac cccagcagca atgaagggcc tggcagctgc tgcccaacgg    2340
gtctccgacg ataccagcag catatacatg cctactcaac aagtcggagt cctcactggg    2400
cttagcgagg gggggtccca agctctacaa ggcggatcga atagatcgca agggcaacca    2460
gaagccgggg atggggagac ccaattcctg gatctgatga gagcggtagc aaatagcatg    2520
agggaggcgc caaactctgc acagggcact ccccaatcgg ggcctccccc aactcctggg    2580
ccatcccaag ataacgacac cgactggggg tattgacctg caggcatgca agggcggccg    2640 cttccctttta gtgagggtta atgcttcgag cagacatgat aagatacatt gatgagtttg    2700
gacaaaccac aactagaatg cagtgaaaaa aatgctttat tgtgaaatt tgtgatgcta    2760 ttgctttatt tgtaaccatt ataagctgca ataaacaagt taacaacaac aattgcattc    2820
attttatgtt tcaggttcag ggggagatgt gggaggtttt ttaaagcaag taaaacctct    2880
acaaatgtgg ta                                                        2892

<210> SEQ ID NO 40
<211> LENGTH: 2658
<212> TYPE: DNA
<213> ORGANISM: Unknown
<220> FEATURE:
<223> OTHER INFORMATION: Cytomegalovirus Newcastle disease virus

<400> SEQUENCE: 40
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg accccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga    420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca gtctccacc ccattgacgt    600 caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
```

```
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagaatt cagaaaaaag tacgggtaga agagggatat tcagagatca   1140
gggcaagtct cccgagtctc tgctctctcc tctacctgat agaccaggac aaacaatggc   1200 caccttttaca gatgcagaga tcgacgagct atttgagaca gtggaactg tcattgacaa    1260 cataattaca gcccagggta aaccagcaga gactgttgga aggagtgcaa tcccacaagg   1320
caagaccaag gtgctgagcg cagcatggga gaagcatggg agcatccagc caccggccag   1380
tcaagacaac cccgatcgac aggacagatc tgacaaacaa ccatccacac ccgagcaaac   1440
gaccccgcat gacagcccgc cggccacatc cgccgaccag ccccccaccc aggccacaga   1500
cgaagccgtc gacacacagc tcaggaccgg agcaagcaac tctctgctgt tgatgcttga   1560
caagctcagc aataaatcgt ccaatgctaa aagggccca tggtcgagcc cccaagaggg    1620
gaatcaccaa cgtccgactc aacagcaggg gagtcaaccc agtcgcggaa acagtcagga   1680
aagaccgcag aaccaagtca aggccgcccc tggaaaccag ggcacagacg tgaacacagc   1740
atatcatgga caatgggagg agtcacaact atcagctggt gcaacccctc atgctctccg   1800
atcaaggcag agccaagaca ataccettgt atctgcggat catgtccagc cacctgtaga   1860
ctttgtgcaa gcgatgatgt ctatgatgga ggcgatatca cagagagtaa gtaaggttga   1920
ctatcagcta gatcttgtct tgaaacagac atcctccatc cctatgatgc ggtccgaaat   1980 ccaacgctg aaaacatctg ttgcagtcat ggaagccaac ttgggaatga tgaagattct    2040
ggatcccggt tgtgccaaca tttcatctct gagtgatcta cgggcagttg cccgatctca   2100
cccggtttta gtttcaggcc ctggagaccc ctctccctat gtgacacaag gaggcgaaat   2160
ggcacttaat aaactttcgc aaccagtgcc acatccatct gaattgatta aactcgccac   2220
tgcatgcggg cctgatatag gagtggaaaa ggacactgtc cgtgcattga tcatgtcacg   2280
cccaatgcac ccgagttctt cagccaagct cctaagcaag ttagatgcag ccgggtcgat   2340
cgaggaaatc aggaaaatca agcgccttgc agtgaatggc taatctagag tcgacccggg   2400
cggccgcttc cctttagtga gggttaatgc ttcgagcaga catgataaga tacattgatg   2460
agtttggaca aaccacaact agaatgcagt gaaaaaaatg ctttatttgt gaaatttgtg   2520
atgctattgc tttatttgta accattataa gctgcaataa acaagttaac aacaacaatt   2580
gcattcattt tatgtttcag gttcaggggg agatgtggga ggttttttaa agcaagtaaa   2640
acctctacaa atgtggta                                                  2658
```

<210> SEQ ID NO 41
<211> LENGTH: 7989
<212> TYPE: DNA
<213> ORGANISM: Unknown
<220> FEATURE:
<223> OTHER INFORMATION: Cytomegalovirus Newcastle disease virus

<400> SEQUENCE: 41

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
```

```
gtcattagtt catagcccat atatggagtt ccgcgttaca taacttacgg taaatggccc    240
gcctggctga ccgcccaacg accccgccc attgacgtca ataatgacgt atgttcccat     300
agtaacgcca atagggactt tccattgacg tcaatgggtg gagtatttac ggtaaactgc    360
ccacttggca gtacatcaag tgtatcatat gccaagtccg cccctattg acgtcaatga     420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca gtctccacc ccattgacgt     600 caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac    1020
aggtgtccac tcccagttca attacagctc ttaaggctag agtacttaat acgactcact    1080
ataggctagc ctcgagaatt cacgcgtaat tatggcgagc tccggtcctg aaagggcaga    1140
gcatcagatt atcctaccag agccacacct gtcttcacca ttggtcaagc acaaactact    1200
ctattactgg aaattaactg gctaccgct tcctgatgaa tgtgacttcg accacctcat     1260
tctcagccga caatggaaaa aaatacttga atcggcctct cctgatactg agagaatgat    1320
aaaactcgga agggcagtac accaaactct taaccacaat tccagaataa ccggagtgct    1380
ccaccccagg tgtttagaac aactggctaa tattgaggtc ccagattcaa ccaacaaatt    1440
tcggaagatt gagaagaaga tccaaattca caacacgaga tatggagaac tgttcacaag    1500
gctgtgtacg catatagaga agaaactgct ggggtcatct tggtctaaca atgtccccg     1560 gtcagaggag ttcagcagca ttcgtacgga tccggcattc tggtttcact caaaatggtc    1620
cacagccaag tttgcatggc tccatataaa acagatccag aggcatctga tggtggcagc    1680
taagacaagg tctgcggcca acaaattggt gatgctaacc cataaggtag gccaagtctt    1740
tgtcactcct gaacttgtcg ttgtgacgca tacgaatgag aacaagttca catgtcttac    1800
ccaggaactt gtattgatgt atgcagatat gatggagggc agagatatgg tcaacataat    1860
atcaaccacg gcggtgcatc tcagaagctt atcagagaaa attgatgaca ttttgcggtt    1920
aatagacgct ctggcaaaag acttgggtaa tcaagtctac gatgttgtat cactaatgga    1980
gggatttgca tacggagctg tccagctact cgagccgtca ggtacatttg caggagattt    2040
cttcgcattc aacctgcagg agcttaaaga cattctaatt ggcctcctcc ccaatgatat    2100
agcagaatcc gtgactcatg caatcgctac tgtattctct ggtttagaac agaatcaagc    2160
agctgagatg ttgtgtctgt tgcgtctgtg gggtcaccca ctgcttgagt cccgtattgc    2220
agcaaaggca gtcaggagcc aaatgtgcgc accgaaaatg gtagactttg atatgatcct    2280
tcaggtactg tctttcttca agggaacaat catcaacggg tacagaaaga gaatgcagg    2340 tgtgtggccg cgagtcaaag tggatacaat atatgggaag gtcattgggc aactacatgc    2400
agattcagca gagatttcac acgatatcat gttgagagag tataagagtt tatctgcact    2460
tgaatttgag ccatgtatag aatatgaccc tgtcaccaac ctgagcatgt tcctaaaaga    2520
caaggcaatc gcacacccca acgataattg gcttgcctcg tttaggcgga accttctctc    2580
```

```
cgaagaccag aagaaacatg taaaagaagc aacttcgact aatcgcctct tgatagagtt    2640
tttagagtca aatgattttg atccatataa agagatggaa tatctgacga cccttgagta    2700
ccttagagat gacaatgtgg cagtatcata ctcgctcaag gagaaggaag tgaaagttaa    2760
tggacggatc ttcgctaagc tgacaaagaa gttaaggaac tgtcaggtga tggcggaagg    2820
gatcctagcc gatcagattg cacctttctt tcagggaaat ggagtcattc aggatagcat    2880
atccttgacc aagagtatgc tagcgatgag tcaactgtct tttaacagca ataagaaacg    2940
tatcactgac tgtaaagaaa gagtatcttc aaaccgcaat catgatccga aaagcaagaa    3000
ccgtcggaga gttgcaacct tcataacaac tgacctgcaa aagtactgtc ttaattggag    3060
atatcagaca atcaaattgt tcgctcatgc catcaatcag ttgatgggcc tacctcactt    3120
cttcgaatgg attcacctaa gactgatgga cactacgatg ttcgtaggag accctttcaa    3180
tcctccaagt gaccctactg actgtgacct ctcaagagtc cctaatgatg acatatatat    3240
tgtcagtgcc agagggggta tcgaaggatt atgccagaag ctatggacaa tgatctcaat    3300
tgctgcaatc caacttgctg cagctagatc gcattgtcgt gttgcctgta tggtacaggg    3360
tgataatcaa gtaatagcag taacgagaga ggtaagatca gacgactctc cggagatggt    3420
gttgacacag ttgcatcaag ccagtgataa tttcttcaag gaattaattc atgtcaatca    3480
tttgattggc cataatttga aggatcgtga aaccatcagg tcagacacat tcttcatata    3540
cagcaaacga atcttcaaag atggagcaat cctcagtcaa gtcctcaaaa attcatctaa    3600
attagtgcta gtgtcaggtg atctcagtga aaacaccgta atgtcctgtg ccaacattgc    3660
ctctactgta gcacggctat gcgagaacgg gcttcccaaa gacttctgtt actatttaaa    3720
ctatataatg agttgtgtgc agacatactt tgactctgag ttctccatca ccaacaattc    3780
gcaccccgat cttaatcagt cgtggattga ggacatctct tttgtgcact catatgttct    3840
gactcctgcc caattagggg gactgagtaa ccttcaatac tcaaggctct acactagaaa    3900
tatcggtgac ccggggacta ctgcttttgc agagatcaag cgactagaag cagtgggatt    3960
actgagtcct aacattatga ctaatatctt aactaggccg cctgggaatg gagattgggc    4020
cagtctgtgc aacgacccat actctttcaa ttttgagact gttgcaagcc caaatattgt    4080
tcttaagaaa catacgcaaa gagtcctatt tgaaacttgt tcaaatccct tattgtctgg    4140
agtgcacaca gaggataatg aggcagaaga gaaggcattg gctgaattct tgcttaatca    4200
agaggtgatt catccccgcg ttgcgcatgc catcatggag gcaagctctg taggtaggag    4260
aaagcaaatt caagggcttg ttgacacaac aaacaccgta attaagattg cgcttactag    4320
gaggccatta ggcatcaaga ggctgatgcg gatagtcaat tattctagca tgcatgcaat    4380
gctgtttaga gacgatgttt tttcctccag tagatccaac cacccttag tctcttctaa     4440 tatgtgttct ctgacactgg cagactatgc acggaataga agctggtcac ctttgacggg    4500
aggcaggaaa atactgggtg tatctaatcc tgatacgata gaactcgtag agggtgagat    4560
tcttagtgta agcggagggt gtacaagatg tgacagcgga gatgaacaat ttacttggtt    4620
ccatcttcca agcaatatag aattgaccga tgacaccagc aagaatcctc cgatgagggt    4680
accatatctc gggtcaaaga cacaggagag gagagctgcc tcacttgcaa aaatagctca    4740
tatgtcgcca catgtaaagg ctgccctaag ggcatcatcc gtgttgatct gggcttatgg    4800
ggataatgaa gtaaattgga ctgctgctct tacgattgca aaatctcggt gtaatgtaaa    4860
cttagagtat cttcggttac tgtcccctt acccacggct gggaatcttc aacatagact     4920
```

```
agatgatggt ataactcaga tgacattcac ccctgcatct ctctacaggg tgtcaccta      4980 cattcacata tccaatgatt ctcaaaggct gttcactgaa gaaggagtca aagagggaa      5040 tgtggtttac caacagatca tgctcttggg tttatctcta atcgaatcga tctttccaat    5100
gacaacaacc aggacatatg atgagatcac actgcaccta catagtaaat ttagttgctg    5160
tatcagagaa gcacctgttg cggttccttt cgagctactt ggggtggtac cggaactgag    5220
gacagtgacc tcaaataagt ttatgtatga tcctagccct gtatcggagg gagactttgc    5280
gagacttgac ttagctatct tcaagagtta tgagcttaat ctggagtcat atcccacgat    5340
agagctaatg aacattcttt caatatccag cgggaagttg attggccagt ctgtggtttc    5400
ttatgatgaa gatacctcca taaagaatga cgccataata gtgtatgaca atacccgaaa    5460
ttggatcagt gaagctcaga attcagatgt ggtccgccta tttgaatatg cagcacttga    5520
agtgctcctc gactgttctt accaactcta ttacctgaga gtaagaggcc tagacaatat    5580
tgtcttatat atgggtgatt tatacaagaa tatgccagga attctacttt ccaacattgc    5640
agctacaata tctcatcccg tcattcattc aaggttacat gcagtgggcc tggtcaacca    5700
tgacggatca caccaacttg cagatacgga ttttatcgaa atgtctgcaa aactattagt    5760
atcttgcacc cgacgtgtga tctccggctt atattcagga ataagtatg atctgctgtt     5820 cccatctgtc ttagatgata acctgaatga gaagatgctt cagctgatat cccggttatg    5880
ctgtctgtac acggtactct tgctacaac aagagaaatc ccgaaaataa gaggcttaac     5940
tgcagaagag aaatgttcaa tactcactga gtatttactg tcggatgctg tgaaaccatt    6000
acttagcccc gatcaagtga gctctatcat gtctcctaac ataattacat cccagctaa     6060 tctgtactac atgtctcgga gagcctcaa tttgatcagg gaaagggagg acagggatac     6120
tatcctggcg ttgttgttcc cccaagagcc attattagag ttcccttctg tgcaagatat    6180
tggtgctcga gtgaaagatc cattcacccg acaacctgcg gcattttgc aagagttaga     6240 tttgagtgct ccagcaaggt atgacgcatt cacacttagt cagattcatc ctgaactcac    6300
atctccaaat ccggaggaag actacttagt acgatacttg ttcagaggga tagggactgc    6360
atcttcctct tggtataagg catctcatct cctttctgta cccgaggtaa gatgtgcaag    6420
acacgggaac tccttatact tagctgaagg gagcggagcc atcatgagtc ttctcgaact    6480
gcatgtacca catgaaacta tctattacaa tacgctcttt tcaaatgaga tgaacccccc    6540
gcaacgacat ttcgggccga ccccaactca gttttgaat tcggttgttt ataggaatct     6600
acaggcggag gtaacatgca aagatggatt tgtccaagag ttccgtccat tatggagaga    6660
aaatacagag gaaagtgacc tgacctcaga taaagcagtg gggtatatta catctgcagt    6720
gccctacaga tctgtatcat tgctgcattg tgacattgaa attcctccag ggtccaatca    6780
aagcttacta gatcaactag ctatcaattt atctctgatt gccatgcatt ctgtaaggga    6840
gggcggggta gtaatcatca aagtgttgta tgcaatggga tactactttc atctactcat    6900
gaacttgttt gctccgtgtt ccacaaaagg atatattctc tctaatggtt atgcatgtcg    6960
aggagatatg gagtgttacc tggtatttgt catgggttac ctgggcgggc ctacatttgt    7020
acatgaggtg tgaggatgg caaaaactct ggtgcagcgg cacggtacgc tcttgtctaa     7080
atcagatgag atcacactga ccaggttatt cacctcacag cggcagcgtg tgacagacat    7140
cctatccagt cctttaccaa gattaataaa gtacttgagg aagaatattg acactgcgct    7200
gattgaagcc gggggacagc ccgtccgtcc attctgtgcg gagagtctgg tgagcacgct    7260
agcgaacata actcagataa cccagattat cgctagtcac attgacacag ttatccggtc    7320
```

```
tgtgatatat atggaagctg agggtgatct cgctgacaca gtatttctat ttacccctta    7380
caatctctct actgacggga aaagaggac atcacttata cagtgcacga gacagatcct    7440
agaggttaca atactaggtc ttagagtcga aaatctcaat aaaataggcg atataatcag    7500
cctagtgctt aaaggcatga tctcaatgga ggaccttatc ccactaagga catacttgaa    7560
gcatagtacc tgccctaaat atttgaaggc tgtcctaggt attaccaaac tcaaagaaat    7620
gtttacagac acttctgtat tgtacttgac tcgtgctcaa caaaaattct acatgaaaac    7680
tataggcaat gcagtcaaag gatattacag taactgtgac tcttaatgaa gcggccgctt    7740
ccctttagtg agggttaatg cttcgagcag acatgataag atacattgat gagtttggac    7800
aaaccacaac tagaatgcag tgaaaaaaat gctttatttg tgaaatttgt gatgctattg    7860
ctttatttgt aaccattata agctgcaata aacaagttaa caacaacaat tgcattcatt    7920
ttatgtttca ggttcagggg gagatgtggg aggttttta aagcaagtaa aacctctaca    7980
aatgtggta                                                           7989
```

<210> SEQ ID NO 42
<211> LENGTH: 2655
<212> TYPE: DNA
<213> ORGANISM: Bacteriophage T7

<400> SEQUENCE: 42

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg gctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg aaacgtgct   1140 gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
```

```
aaaatccacg gtgcaaactg tgcgggtgtc gataaggttc cgttccctga gcgcatcaag    1440
ttcattgagg aaaaccacga gaacatcatg gcttgcgcta agtctccact ggagaacact    1500
tggtgggctg agcaagattc tccgttctgc ttccttgcgt tctgctttga gtacgctggg    1560
gtacagcacc acggcctgag ctataactgc tcccttccgc tggcgtttga cgggtcttgc    1620
tctggcatcc agcacttctc cgcgatgctc cgagatgagg taggtggtcg cgcggttaac    1680
ttgcttccta gtgaaaccgt tcaggacatc tacgggattg ttgctaagaa agtcaacgag    1740
attctacaag cagacgcaat caatgggacc gataacgaag tagttaccgt gaccgatgag    1800
aacactggtg aaatctctga gaaagtcaag ctgggcacta aggcactggc tggtcaatgg    1860
ctggcttacg gtgttactcg cagtgtgact aagcgttcag tcatgacgct ggcttacggg    1920
tccaaagagt tcggcttccg tcaacaagtg ctggaagata ccattcagcc agctattgat    1980
tccggcaagg gtctgatgtt cactcagccg aatcaggctg ctggatacat ggctaagctg    2040
atttgggaat ctgtgagcgt gacggtggta gctgcggttg aagcaatgaa ctggcttaag    2100
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca acaaagatag cgagattgat gcacacaaac aggagtctgg tatcgctcct    2340
aactttgtac acagccaaga cggtagccac cttcgtaaga ctgtagtgtg ggcacacgag    2400
aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgt aataa                                                    2655

<210> SEQ ID NO 43
<211> LENGTH: 36
<212> TYPE: DNA
<213> ORGANISM: Artificial Sequence
<220> FEATURE:
<223> OTHER INFORMATION: Synthetic

<400> SEQUENCE: 43
aaatacgcgt aattatggcg agctccggtc ctgaaa                              36

<210> SEQ ID NO 44
<211> LENGTH: 35
<212> TYPE: DNA
<213> ORGANISM: Artificial Sequence
<220> FEATURE:
<223> OTHER INFORMATION: Synthetic

<400> SEQUENCE: 44
tatggatcct atttatcatc gagctcgaga tctgg                               35

<210> SEQ ID NO 45
<211> LENGTH: 31
<212> TYPE: DNA
<213> ORGANISM: Artificial Sequence
<220> FEATURE:
<223> OTHER INFORMATION: Synthetic

<400> SEQUENCE: 45
catcgtctcc catgcccgcc atgaagatcg a                                   31
```

<210> SEQ ID NO 46
<211> LENGTH: 26
<212> TYPE: DNA
<213> ORGANISM: Artificial Sequence
<220> FEATURE:
<223> OTHER INFORMATION: Synthetic

<400> SEQUENCE: 46
cgaattctta cgcgaacgcg aagtcc                                      26

<210> SEQ ID NO 47
<211> LENGTH: 29
<212> TYPE: DNA
<213> ORGANISM: Artificial Sequence
<220> FEATURE:
<223> OTHER INFORMATION: Synthetic

<400> SEQUENCE: 47
ccggatccat gaacacgatt aacatcgct                                   29

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
aagaccgtgt tgaggtgtta tta                                         23

<210> SEQ ID NO 49
<211> LENGTH: 22
<212> TYPE: DNA
<213> ORGANISM: Artificial Sequence
<220> FEATURE:
<223> OTHER INFORMATION: Synthetic

<400> SEQUENCE: 49
tccccaatgt agatactgct tc                                          22

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tatccagcaa ggcgtgtcta                                             20

<210> SEQ ID NO 51
<211> LENGTH: 21
<212> TYPE: DNA
<213> ORGANISM: Artificial Sequence
<220> FEATURE:
<223> OTHER INFORMATION: Synthetic

<400> SEQUENCE: 51
ttgtcactgt gtctgcgtct t                                           21

<210> SEQ ID NO 52
<211> LENGTH: 23
<212> TYPE: DNA
<213> ORGANISM: Artificial Sequence
<220> FEATURE:

<223> OTHER INFORMATION: Synthetic

<400> SEQUENCE: 52
cactccaatt ctacccgtat ttt                                              23

<210> SEQ ID NO 53
<211> LENGTH: 25
<212> TYPE: DNA
<213> ORGANISM: Artificial Sequence
<220> FEATURE:
<223> OTHER INFORMATION: Synthetic

<400> SEQUENCE: 53
ctaccatgat cctagtgagt gtttt                                            25

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gctttggttg cttgctacaa                                                  20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
gaaccgtgca atggtaagaa                                                  20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
ggtgttgcaa ctgcagctgc                                                  20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
cttcctcagc cccactgaat                                                  20

<210> SEQ ID NO 58
<211> LENGTH: 26
<212> TYPE: DNA
<213> ORGANISM: Artificial Sequence
<220> FEATURE:
<223> OTHER INFORMATION: Synthetic

<400> SEQUENCE: 58
accaaacaga gaatccgtga gttacg                                           26

```
<210> SEQ ID NO 59
<211> LENGTH: 26
<212> TYPE: DNA
<213> ORGANISM: Artificial Sequence
<220> FEATURE:
<223> OTHER INFORMATION: Synthetic

<400> SEQUENCE: 59
accaaacaaa gatttggtga atgacg                                          26

<210> SEQ ID NO 60
<211> LENGTH: 33
<212> TYPE: DNA
<213> ORGANISM: Artificial Sequence
<220> FEATURE:
<223> OTHER INFORMATION: Synthetic

<400> SEQUENCE: 60
ataacgccgg cgcctcacat ggctcgacag atc                                  33

<210> SEQ ID NO 61
<211> LENGTH: 39
<212> TYPE: DNA
<213> ORGANISM: Artificial Sequence
<220> FEATURE:
<223> OTHER INFORMATION: Synthetic

<400> SEQUENCE: 61
tataggccgg ccacgccagc ccggatcgat ccttatcgg                            39

<210> SEQ ID NO 62
<211> LENGTH: 26
<212> TYPE: DNA
<213> ORGANISM: Artificial Sequence
<220> FEATURE:
<223> OTHER INFORMATION: Synthetic

<400> SEQUENCE: 62
atggtgatgg tgatggtggc ttcccc                                          26

<210> SEQ ID NO 63
<211> LENGTH: 25
<212> TYPE: DNA
<213> ORGANISM: Artificial Sequence
<220> FEATURE:
<223> OTHER INFORMATION: Synthetic

<400> SEQUENCE: 63
ggtggcttcc ccttggcacc agtcc                                           25

<210> SEQ ID NO 64
<211> LENGTH: 22
<212> TYPE: DNA
<213> ORGANISM: Artificial Sequence
<220> FEATURE:
<223> OTHER INFORMATION: Synthetic

<400> SEQUENCE: 64
atagcgccca gcacgaatct cc                                              22

<210> SEQ ID NO 65
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 65
tgccgcacga cgttcaggaa                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
tggtcctctc tcagcaggca                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
agcccttgtt cagctgcttg                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
gaaagtaagg tccaattgcc                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
cagagtgggc atcatcaagc                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
tggcgagaag ggcaactacg                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
cagttcaacc ggcggttcct                                              20

<210> SEQ ID NO 72
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 72
agatcgagaa ccctcgggct                                          20

<210> SEQ ID NO 73
<211> LENGTH: 22
<212> TYPE: DNA
<213> ORGANISM: Artificial Sequence
<220> FEATURE:
<223> OTHER INFORMATION: Synthetic

<400> SEQUENCE: 73
aaacttgtcg acgctagcgc cg                                       22

<210> SEQ ID NO 74
<211> LENGTH: 35
<212> TYPE: DNA
<213> ORGANISM: Artificial Sequence
<220> FEATURE:
<223> OTHER INFORMATION: Synthetic

<400> SEQUENCE: 74
ccagctcgag tcattagcca tttagagcaa ggcgc                         35

<210> SEQ ID NO 75
<211> LENGTH: 36
<212> TYPE: DNA
<213> ORGANISM: Artificial Sequence
<220> FEATURE:
<223> OTHER INFORMATION: Synthetic

<400> SEQUENCE: 75
ccgcatcgtc tcccatggcc acctttacag atgcag                        36

<210> SEQ ID NO 76
<211> LENGTH: 37
<212> TYPE: DNA
<213> ORGANISM: Artificial Sequence
<220> FEATURE:
<223> OTHER INFORMATION: Synthetic

<400> SEQUENCE: 76
ttatctcgag ttttatcagt accccagtc ggtgtcg                        37

<210> SEQ ID NO 77
<211> LENGTH: 30
<212> TYPE: DNA
<213> ORGANISM: Artificial Sequence
<220> FEATURE:
<223> OTHER INFORMATION: Synthetic

<400> SEQUENCE: 77
cgcatacatg tcttccgtat ttgatgagta                               30

<210> SEQ ID NO 78
<211> LENGTH: 28
<212> TYPE: DNA
<213> ORGANISM: Artificial Sequence
<220> FEATURE:
<223> OTHER INFORMATION: Synthetic

<400> SEQUENCE: 78
```

```
caaaggatat tacagtaact gtgactct                                      28

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
actgcgctga ttgaagccgg                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
catctgcagt gccctacaga                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
cattcacccg acaacctgcg                                               20

<210> SEQ ID NO 82
<211> LENGTH: 21
<212> TYPE: DNA
<213> ORGANISM: Artificial Sequence
<220> FEATURE:
<223> OTHER INFORMATION: Synthetic

<400> SEQUENCE: 82
tcacaccaac ttgcagatac g                                             21

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
accggaactg aggacagtga                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
acaggagagg agagctgcct                                               20

<210> SEQ ID NO 85
<211> LENGTH: 20
<212> TYPE: DNA
<213> ORGANISM: Artificial Sequence
```

<220> FEATURE:
<223> OTHER INFORMATION: Synthetic

<400> SEQUENCE: 85
tgattcatcc ccgcgttgcg                                                    20

<210> SEQ ID NO 86
<211> LENGTH: 28
<212> TYPE: DNA
<213> ORGANISM: Artificial Sequence
<220> FEATURE:
<223> OTHER INFORMATION: Synthetic

<400> SEQUENCE: 86
gcttcccaaa gacttctgtt actattta                                           28

<210> SEQ ID NO 87
<211> LENGTH: 21
<212> TYPE: DNA
<213> ORGANISM: Artificial Sequence
<220> FEATURE:
<223> OTHER INFORMATION: Synthetic

<400> SEQUENCE: 87
tgtgacctct caagagtccc t                                                  21

<210> SEQ ID NO 88
<211> LENGTH: 22
<212> TYPE: DNA
<213> ORGANISM: Artificial Sequence
<220> FEATURE:
<223> OTHER INFORMATION: Synthetic

<400> SEQUENCE: 88
ccttagagat gacaatgtgg ca                                                 22

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
gcttgagtcc cgtattgcag                                                    20

<210> SEQ ID NO 90
<211> LENGTH: 22
<212> TYPE: DNA
<213> ORGANISM: Artificial Sequence
<220> FEATURE:
<223> OTHER INFORMATION: Synthetic

<400> SEQUENCE: 90
caacaaattg gtgatgctaa cc                                                 22

<210> SEQ ID NO 91
<211> LENGTH: 28
<212> TYPE: DNA
<213> ORGANISM: Artificial Sequence
<220> FEATURE:
<223> OTHER INFORMATION: Synthetic

<400> SEQUENCE: 91
caagcacaaa ctactctatt actggaaa                                           28

<210> SEQ ID NO 92
<211> LENGTH: 21
<212> TYPE: DNA
<213> ORGANISM: Artificial Sequence
<220> FEATURE:
<223> OTHER INFORMATION: Synthetic

<400> SEQUENCE: 92
caagcagtac caaagcagca t                                      21

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
attcgaatgg ccaagtcttc                                        20

<210> SEQ ID NO 94
<211> LENGTH: 23
<212> TYPE: DNA
<213> ORGANISM: Artificial Sequence
<220> FEATURE:
<223> OTHER INFORMATION: Synthetic

<400> SEQUENCE: 94
cccattactg ctacacccat aat                                    23

<210> SEQ ID NO 95
<211> LENGTH: 24
<212> TYPE: DNA
<213> ORGANISM: Artificial Sequence
<220> FEATURE:
<223> OTHER INFORMATION: Synthetic

<400> SEQUENCE: 95
gcaaaaaata catggcgctt gata                                   24

<210> SEQ ID NO 96
<211> LENGTH: 25
<212> TYPE: DNA
<213> ORGANISM: Artificial Sequence
<220> FEATURE:
<223> OTHER INFORMATION: Synthetic

<400> SEQUENCE: 96
caactcgatc agtaatgctt tgaat                                  25

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
cgtaagcaca accagggat                                         20

<210> SEQ ID NO 98
<211> LENGTH: 22
<212> TYPE: DNA
<213> ORGANISM: Artificial Sequence
<220> FEATURE:
<223> OTHER INFORMATION: Synthetic

<400> SEQUENCE: 98
agctctgata caagccaaac aa                                              22

<210> SEQ ID NO 99
<211> LENGTH: 22
<212> TYPE: DNA
<213> ORGANISM: Artificial Sequence
<220> FEATURE:
<223> OTHER INFORMATION: Synthetic

<400> SEQUENCE: 99
cccagatcat catgacacaa aa                                              22

<210> SEQ ID NO 100
<211> LENGTH: 21
<212> TYPE: DNA
<213> ORGANISM: Artificial Sequence
<220> FEATURE:
<223> OTHER INFORMATION: Synthetic

<400> SEQUENCE: 100
ttgtctaagt ctgacagcgg a                                               21

<210> SEQ ID NO 101
<211> LENGTH: 23
<212> TYPE: DNA
<213> ORGANISM: Artificial Sequence
<220> FEATURE:
<223> OTHER INFORMATION: Synthetic

<400> SEQUENCE: 101
cagtattcat caccacctat gga                                             23

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
tgatcatgtc acgcccaatg                                                 20

<210> SEQ ID NO 103
<211> LENGTH: 22
<212> TYPE: DNA
<213> ORGANISM: Artificial Sequence
<220> FEATURE:
<223> OTHER INFORMATION: Synthetic

<400> SEQUENCE: 103
cacaactatc agctggtgca ac                                              22

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
ttacagccca gggtaaacca                                                 20

<210> SEQ ID NO 105

```
<211> LENGTH: 20
<212> TYPE: DNA
<213> ORGANISM: Artificial Sequence
<220> FEATURE:
<223> OTHER INFORMATION: Synthetic

<400> SEQUENCE: 105
cccaattcct ggatctgatg                                                    20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
gacatcagcc cttgcactta                                                    20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
gccccagttc aacaatagga                                                    20

<210> SEQ ID NO 108
<211> LENGTH: 22
<212> TYPE: DNA
<213> ORGANISM: Artificial Sequence
<220> FEATURE:
<223> OTHER INFORMATION: Synthetic

<400> SEQUENCE: 108 cccttttcgtc ttcaagaatt ct                                                22

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
ttgttgaact ggggcgtgcc                                                    20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
aacgcatgag ctgcttcatc                                                    20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
```
tcgttatctt gggatggccc                                           20

<210> SEQ ID NO 112
<211> LENGTH: 21
<212> TYPE: DNA
<213> ORGANISM: Artificial Sequence
<220> FEATURE:
<223> OTHER INFORMATION: Synthetic

<400> SEQUENCE: 112
gggtgtggat ggttgtttgt c                                         21

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
gatttcggac cgcatcatag                                           20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
attaattacg gttggccggc                                           20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
ttctctggcg ctttcacgtg                                           20

<210> SEQ ID NO 116
<211> LENGTH: 25
<212> TYPE: DNA
<213> ORGANISM: Artificial Sequence
<220> FEATURE:
<223> OTHER INFORMATION: Synthetic

<400> SEQUENCE: 116
tagaggtaac ctcgtggtcg gcggt                                     25

<210> SEQ ID NO 117
<211> LENGTH: 21
<212> TYPE: DNA
<213> ORGANISM: Artificial Sequence
<220> FEATURE:
<223> OTHER INFORMATION: Synthetic

<400> SEQUENCE: 117 cccccctccag atgtagtcac a                                        21

<210> SEQ ID NO 118
<211> LENGTH: 21
<212> TYPE: DNA

<213> ORGANISM: Artificial Sequence
<220> FEATURE:
<223> OTHER INFORMATION: Synthetic

<400> SEQUENCE: 118
ttaggttccc gactgaaggt a				21

<210> SEQ ID NO 119
<211> LENGTH: 28
<212> TYPE: DNA
<213> ORGANISM: Artificial Sequence
<220> FEATURE:
<223> OTHER INFORMATION: Synthetic

<400> SEQUENCE: 119
ctgttgcttt cctctaactt attcaaag				28

<210> SEQ ID NO 120
<211> LENGTH: 26
<212> TYPE: DNA
<213> ORGANISM: Artificial Sequence
<220> FEATURE:
<223> OTHER INFORMATION: Synthetic

<400> SEQUENCE: 120
gctacagata tagccaaggt cactac				26

<210> SEQ ID NO 121
<211> LENGTH: 24
<212> TYPE: DNA
<213> ORGANISM: Artificial Sequence
<220> FEATURE:
<223> OTHER INFORMATION: Synthetic

<400> SEQUENCE: 121
cgcagagtag aaaagaatac cctc				24

<210> SEQ ID NO 122
<211> LENGTH: 23
<212> TYPE: DNA
<213> ORGANISM: Artificial Sequence
<220> FEATURE:
<223> OTHER INFORMATION: Synthetic

<400> SEQUENCE: 122
ccctactgtg agaattctgc ctt				23

<210> SEQ ID NO 123
<211> LENGTH: 23
<212> TYPE: DNA
<213> ORGANISM: Artificial Sequence
<220> FEATURE:
<223> OTHER INFORMATION: Synthetic

<400> SEQUENCE: 123
gatacaatgc catctttcca act				23

<210> SEQ ID NO 124
<211> LENGTH: 25
<212> TYPE: DNA
<213> ORGANISM: Artificial Sequence
<220> FEATURE:
<223> OTHER INFORMATION: Synthetic

<400> SEQUENCE: 124
gtgaatttgg atcttcttct caatc				25

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
gctcgagtag ctggacagct                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
cctaaacgag gcaagccaat                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
tgaggtaggc ccatcaactg                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
cagtagaggc aatgttggca                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
gcggggatga atcacctctt                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
ccttagggca gcctttacat                                              20

<210> SEQ ID NO 131
<211> LENGTH: 26
<212> TYPE: DNA
<213> ORGANISM: Artificial Sequence
<220> FEATURE:

```
<223> OTHER INFORMATION: Synthetic

<400> SEQUENCE: 131
tgactccaga ttaagctcat aactct                                          26

<210> SEQ ID NO 132
<211> LENGTH: 21
<212> TYPE: DNA
<213> ORGANISM: Artificial Sequence
<220> FEATURE:
<223> OTHER INFORMATION: Synthetic

<400> SEQUENCE: 132
cgggatatca gctgaagcat c                                               21

<210> SEQ ID NO 133
<211> LENGTH: 22
<212> TYPE: DNA
<213> ORGANISM: Artificial Sequence
<220> FEATURE:
<223> OTHER INFORMATION: Synthetic

<400> SEQUENCE: 133
ccgtgtcttg cacatcttac ct                                              22

<210> SEQ ID NO 134
<211> LENGTH: 22
<212> TYPE: DNA
<213> ORGANISM: Artificial Sequence
<220> FEATURE:
<223> OTHER INFORMATION: Synthetic

<400> SEQUENCE: 134
aacactccat atctcctcga ca                                              22

<210> SEQ ID NO 135
<211> LENGTH: 21
<212> TYPE: DNA
<213> ORGANISM: Artificial Sequence
<220> FEATURE:
<223> OTHER INFORMATION: Synthetic

<400> SEQUENCE: 135
atggagatca tgcctttaag c                                               21

<210> SEQ ID NO 136
<211> LENGTH: 24
<212> TYPE: DNA
<213> ORGANISM: Artificial Sequence
<220> FEATURE:
<223> OTHER INFORMATION: Synthetic

<400> SEQUENCE: 136
gtgataaact accgcattaa agct                                            24

<210> SEQ ID NO 137
<211> LENGTH: 13
<212> TYPE: DNA
<213> ORGANISM: Avian orthoavulavirus 1

<400> SEQUENCE: 137
gccggcgcgt gct                                                        13

<210> SEQ

-continued

```
<212> TYPE: DNA
<213> ORGANISM: Artificial Sequence
<220> FEATURE:
<223> OTHER INFORMATION: Synthetic

<400> SEQUENCE: 138
ggccgcgcgg gcc                                                         13

<210> SEQ ID NO 139
<211> LENGTH: 147
<212> TYPE: DNA
<213> ORGANISM: Artificial Sequence
<220> FEATURE:
<223> OTHER INFORMATION: Synthetic

<400> SEQUENCE: 139
ctctacaggt gtcaccttac attcacatat ccaatgattc tcaaaggctg ttcactgaag      60
aaggagtcaa agagggggaat gtggtttacc aacagagtca tgctcttggg tttaatcgaa   120
tcgatctttc caatgacaac aaccagg                                        147

<210> SEQ ID NO 140
<211> LENGTH: 140
<212> TYPE: PRT
<213> ORGANISM: Artificial Sequence
<220> FEATURE:
<223> OTHER INFORMATION: Synthetic

<400> SEQUENCE: 140

Pro Thr Ala Gly Asn Leu Gln His Arg Leu Asp Asp Gly Ile Thr Gln
  1               5                  10                  15

Met Thr Phe Thr Pro Ser Ala Leu Tyr Arg Val Ser Pro Tyr Ile His
             20                  25                  30

Ile Ser Asn Asp Ser Gln Arg Leu Phe Thr Glu Glu Gly Val Lys Glu
         35                  40                  45

Gly Asn Val Val Tyr Gln Gln Ile Met Leu Leu Gly Leu Ser Leu Ile
     50                  55                  60

Glu Ser Ile Phe Pro Met Thr Thr Arg Thr Tyr Asp Glu Ile Thr
 65                  70                  75                  80

Leu His Leu His Ser Lys Phe Ser Cys Cys Ile Arg Glu Ala Pro Val
                 85                  90                  95

Ala Val Pro Phe Glu Leu Leu Gly Val Val Pro Glu Leu Arg Thr Val
            100                 105                 110

Thr Ser Asn Lys Phe Met Tyr Asp Pro Ser Pro Val Ser Glu Gly Asp
        115                 120                 125

Phe Ala Arg Leu Asp Leu Ala Ile Phe Lys Ser Tyr
    130                 135                 140

<210> SEQ ID NO 141
<211> LENGTH: 140
<212> TYPE: PRT
<213> ORGANISM: Artificial Sequence
<220> FEATURE:
<223> OTHER INFORMATION: Synthetic

<400> SEQUENCE: 141

Pro Thr Ala Gly Asn Leu Gln His Arg Leu Asp Asp Gly Ile Thr Gln
  1               5                  10                  15

Met Thr Phe Thr Pro Ala Ser Leu Tyr Arg Cys His Leu Thr Phe Thr
             20                  25                  30

Tyr Pro Met Ile Leu Lys Gly Cys Ser Leu Lys Lys Glu Ser Lys Arg
```

```
                    35                  40                  45
Gly Met Trp Phe Thr Asn Arg Val Met Leu Leu Gly Leu Ser Leu Ile
        50                  55                  60

Glu Ser Ile Phe Pro Met Thr Thr Thr Arg Thr Tyr Asp Glu Ile Thr
 65                  70                  75                  80

Leu His Leu His Ser Lys Phe Ser Cys Cys Ile Arg Glu Ala Pro Val
                 85                  90                  95

Ala Val Pro Phe Glu Leu Leu Gly Val Val Pro Glu Leu Arg Thr Val
                100                 105                 110

Thr Ser Asn Lys Phe Met Tyr Asp Pro Ser Pro Val Ser Glu Gly Asp
            115                 120                 125

Phe Ala Arg Leu Asp Leu Ala Ile Phe Lys Ser Tyr
            130                 135                 140

<210> SEQ ID NO 142
<211> LENGTH: 30
<212> TYPE: DNA
<213> ORGANISM: Artificial Sequence
<220> FEATURE:
<223> OTHER INFORMATION: Synthetic

<400> SEQUENCE: 142
taagaaaaaa tacgggtaga agccaccatg                                      30
```

METHOD FOR RESCUING AND PRODUCING A VIRUS IN AVIAN CELLS

RELATED APPLICATION

This application is a national stage filing under 35 U.S.C. 371 of International Patent Application Serial No. PCT/EP2019/069030, filed Jul. 15, 2019, the contents of which is incorporated by reference herein in its entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Aug. 22, 2023, is named I04227013611500-SUBSEQ-NTJ and is 148,617 bytes in size.

FIELD OF THE INVENTION

The present invention relates to methods of rescue and/or propagation of paramyxovirus species, particularly wherein both rescue and propagation are carried out in the same cell type; i.e., without the use of helper cells for viral rescue. The paramyxoviruses produced by the disclosed methods may encompass wild-type viruses, chimeric viruses, recombinant viruses or engineered viral products such as virus like particles (VLP). Viruses and/or viral products produced in the method according to the current invention are suitable for medical or veterinary use in such applications as treating or preventing infectious diseases, particularly avian paramyxovirus and human respiratory virus infections, and cancer treatment.

BACKGROUND OF THE INVENTION

Paramyxoviruses, family Paramyxoviridae, are single-stranded non-segmented negative-sense RNA viruses belonging to the order Mononegavirales. Avian paramyxoviruses (genus Avulavirus) comprise at least 13 species, the best characterized of which is Newcastle Disease virus (NDV), also known as avian paramyxovirus serotype 1 (APMV-1; Murphy F.A., et al., 1995, Virus Taxonomy). NDV is the major cause of respiratory and neurologic disease in birds and poultry. The severity of Newcastle disease in poultry ranges from asymptomatic to deadly, depending on the pathotype (Kumar, S., et al., 2011, J. Virol. (85)13:6521-6534) and can result in losses of up to 90% of infected flocks. Even in geographical areas where NDV is well-controlled, it remains an economic burden due to the need to vaccinate and maintain strict biosecurity measures (Alexander, D J, 2000, Rev. sci. tech. Off. int. Epiz. 19(2): 443-462). Naturally occurring low virulent NDV strains, such as LaSota and Hitchner B1 strains, are widely used as live-attenuated vaccines to control Newcastle disease in poultry.

Medical applications of NDV include human and veterinary vaccines and uses in cancer therapy. In contrast to other replicating viral vectors, NDV has several advantages as a vaccine vector. For example, there is generally no pre-existing immunity to NDV in humans. Humans and other mammals are largely unaffected by NDV due to natural host range restriction, although exposure to NDV can result in conjunctivitis and/or mild flu-like symptoms in humans. This RNA virus replicates in the cytoplasm, does not integrate into host cell DNA, and does not establish persistent infection, making NDV very safe. Additionally, recombination involving NDV is extremely rare. Also advantageous with regard to immunogenicity, NDV delivery via the intranasal route induces humoral and cellular immune responses both at the mucosal and systemic levels in avian, murine and non-human primate models (Nakaya et al., 2001, J. Virol., 75(23):11868-11873; Bukreyev et al., 2005, J. Virol., 79(21):13275-13284; DiNapoli et al., 2010, Vaccine 29(1): 17-25; Ge et al., 2007, J. Virol., 81(1):150-158). NDV is additionally a potent inducer viral-specific immune responses and dendritic cell maturation (Qian, et al., 2017, Virus Genes, 53(4):555-564).

Newcastle Disease virus selectively replicates in and lyses tumorigenic cells, due at least in part to a dysfunctional type-I interferon (IFN) cascade in tumorigenic cells (Fiola, et al., 2006, Int. J. Cancer: 119:328-338). NDV has been used in numerous studies as an oncolytic agent, as it fulfills criteria in this capacity including efficient oncolysis, strong immunogenicity and tumor selectivity (Kalyanasundram, et al., 2018, Acta *Tropica* 183:126-133). In this regard, NDV has been shown to have oncolytic effect, including the triggering of apoptosis selectively in tumor cells. Furthermore, tumor debris, in combination with NDV components (pathogen-associated molecular patterns; PAMP), can stimulate a tumoricidal immune cascade (Kalyanasundram, et al., supra). Thus, NDV has usefulness both as a directly oncolytic agent and in anti-cancer vaccines prepared from NDV-infected whole cancer cells or cell lysates (PubMed Health "Newcastle Disease Virus (PDQ®) Health Professional Version"; published online Nov. 2, 2016; ncbi.nlm-.nih.gov/pubmedhealth/PMH0032658/accessed May 15, 2018).

The NDV genome is a non-segmented single-stranded negative-sense RNA with a length of 15,186, 15,192 or 15,198 nucleotides (Miller and Koch, 2013, Newcastle disease. In: Swayne, D. E., Glisson, J. R., McDougald, L. R., Nolan, L. K., Suarez, D. L., Nair, V. (Eds.), Diseases of Poultry. John Wiley & Sons, pp. 89-138). The NDV genome contains six genes which encode for nucleocapsid protein (NP), phosphoprotein (P), matrix protein (M), fusion protein (F), hemagglutinin protein (HN) and large protein (L). Additionally, V and W proteins are produced by RNA editing during P gene transcription (Millar and Emmerson, 1988; Stewad et al., 1993). It has been demonstrated that a foreign gene can be inserted as an autonomous transcription unit in NDV genome, leading to expression of the foreign gene in infected cells (Zhao et al., 2015, J. Gen. Virol., 96:40-45). Furthermore, delivery of a foreign gene to host cells by NDV can be accomplished without resulting in virus spread and infection (Kim and Samal, 2016, Viruses 8:183). NDV is thus promising as a recombinant vector for experimental vaccines against infectious diseases. It has been demonstrated that foreign genes can be inserted at different positions throughout the NDV genome without severely affecting replication efficiency or virus yield (Zhao and Peeters, 2003, J. Gen. Virol., 84:781-788). The NDV genome can be modified in various ways; for example, to contain additional elements, modified genes and/or heterologous coding sequences, such as sequences encoding antigens from other viral pathogens. Because of the ease of modifying the NDV genome, a recombinant NDV expression vector can be readily produced.

In particular, a recombinant NDV vector may be used for the delivery of antigens from other viral pathogens, such as respiratory viral pathogens, e.g. human metapneumovirus (hMPV) and/or respiratory syncytial virus (RSV). Human metapneumovirus (hMPV) was discovered in 2001 and is one of the most common causes for upper and lower respiratory tract infections in young children. Currently no vaccines are available. Antigens derived from hMPV and RSV include, e.g., fusion glycoprotein (F-protein) and matrix (M) protein. An hMPV vaccine—and in particular combined to a vaccine against Respiratory Syncytial Virus (RSV)—appears as an attractive medical and commercial option. Studies with inactivated RSV showed that natural infection with RSV following vaccination of infants with no prior exposure to the virus could result in enhanced respiratory disease (ERD), in some cases leading to death (Kim, et al., 1969, American J. of Epidem. 89(4):422-434). Since that study, it has been shown that vaccination with inactivated hMPV can likewise result in ERD in experimental animals (Yim, et al., 2007, Vaccine, 25(27):5034-5040), with a similar Th2 response as observed in earlier RSV studies. The potential causes for enhanced disease following vaccination with inactivated RSV are thought to be Th2-biased T-cell-memory responses, formaldehyde hypersensitivity and/or immature antibody production and its associated weak recognition of hRSV epitopes from natural infections (Ren, et al., 2015, J Gen. Virol. 96(Pt 7):1515-1520). Therefore, a vaccine against hMPV should ideally not only elicit strong mucosal and systemic immune responses, including the production of neutralizing antibodies and a CD8 T cell response (IFN response), but also a balanced Th1/Th2 immune response.

One well-known challenge to producing negative-strand RNA viruses, including NDV, is that naked viral RNA alone is not infectious. Expression of components of the viral ribonucleoprotein complex (RNP), namely N (alternatively referred to as "NP"), P, and L proteins of the virus, is essential for initiation of the first round of RNA synthesis leading to packaging of infectious viral particles ("viral rescue") and for establishment of infection in the host cell. Mammalian cells are permissive to NDV rescue, but the virus is generally unable to replicate in mammalian cells or replicates only at very low levels, due at least in part to the induction of a strong interferon response, which leads to death of infected normal (not tumor) cells (Krishnamurthy S., et al., 2006, J. Virol. 80(11):5145-5155).

In this regard, the first reported rescue of a Mononegavirales from full-length cDNA was done with rabies virus (Schnell, et al., 1994, EMBO J. 13:4195-4203). Following that report, similar techniques were used to recover vesicular stomatitis virus, measles virus, respiratory syncytial virus (RSV) and Sendai virus (Inoue et al., 2003, J. Virolog. Methods 107:229-236). This technique consisted of providing individual plasmids encoding each of the three proteins forming the viral polymerase complex (i.e., N, P and L) along with a plasmid encoding the full-length viral cDNA, with all plasmids under the control of a T7 promoter. The required T7 RNA polymerase can be supplied in the host cell, e.g., by infection of the host cell with recombinant vaccinia virus, vTF7-3, or by transfecting cells with a T7 expression vector under constitutive expression (e.g., with a CMV immediate-early promoter). While an efficient way of providing T7 polymerase, the presence of the vaccinia virus is not desirable in the production of drug products. Furthermore, the vaccinia virus may interfere with rescue of the virus of interest (see, e.g., WO2004/113517) and has a cytopathic effect that may obscure detection of the CPE of the rescued virus. An alternative method of providing T7 is to use a cell line which constitutively expresses T7 RNA polymerase, e.g., BHKT7 or BSR-T7/5. These T7-expressing host cells lines (or "helper cells") are transfected together with the three helper plasmids and the viral expression plasmid under T7 promoter control to rescue infectious viral particles. These cells generally express much lower levels of T7, however, which reduces rescue efficiency.

Although T7-expressing helper cells are useful for viral rescue, they are generally not susceptible to viral infection, but must be co-cultured with permissive host cells, also referred to as "plaque expansion cells". Co-culture with cells susceptible to virus infection facilitates amplification of the extremely low numbers of viral particles produced by the helper cells and allows propagation of a titer useful for many applications.

The rescue of Paramyxoviruses is known in the art to be of very low efficiency and often complex, requiring large numbers of transfected cells and repeated attempts, making the study and use of these viruses challenging (Beatty, et al., 2017, mSphere 2:e00376-16. doi.org/10.1128/mSphere.00376-16). While more efficient methods of rescue are regularly reported, these methods are generally optimizations of the above-described method; particularly with regard to requiring two cell types. The use of one cell type for both rescue and propagation has been described for paramyxoviruses, however, efficiency and reproducibility is poor, making it unsuitable for industrial application (see, e.g., WO2004/113517). Furthermore, many reported rescue protocols require additional steps, such as a heat shock step to increase efficiency of transfection (e.g., WO2004/113517) or multiple freeze-thaw cycles to release the vanishingly small numbers of viral particles obtained by rescue (e.g., Schnell, et al., 1994, supra). These steps are not ideal for inclusion in an industrial process, as they require significant time and energy input.

The current invention provides simple and efficient methods for both rescue and propagation of viral particles in a single cell type. The herein disclosed methods comprise co-transfecting a recombinant paramyxovirus expression vector and three helper plasmids under T7 or CMV control, respectively, along with a constitutive T7 polymerase expression vector, into a paramyxovirus-susceptible avian cell line which is competent for propagation of the rescued viral particles. The process does not require the use of helper cells such as BHKT7, which are often not desirable for production of products for use in humans. Additionally, the disclosed rescue method is highly efficient (reproducible). An additional advantage is the relatively short time needed from transfection to harvest of a high-titer master virus seed bank, which can be reduced from several weeks using some of the prior art methods to as less than about one week. Prior art methods may be fast with low yield or slower. The herein disclosed invention is rapid, reproducible and leads to high titer.

In sum, previously-reported methods of virus rescue and propagation for paramyxoviruses are not optimal for industrial application. As disclosed herein, the current invention provides a robust and reproducible method of propagating viral particles in the same avian cell line as used for viral rescue. This method has the advantages of being simple, efficient, reliable and lacking various undesirable products from the use of helper cells, vaccinia virus, etc. Disclosed herein are steps for the cloning of a recombinant NDV full length genome and helper plasmids necessary for NDV rescue using the methods of the invention. In addition, the expression of foreign proteins by insertion of heterologous coding sequences into the recombinant NDV genome is demonstrated, illustrating the suitability of the methods of the current invention for the production of vaccines for the prevention of diverse diseases.

SUMMARY OF THE INVENTION

The present invention relates to improved methods for producing infectious paramyxovirus particles. Furthermore, the invention provides a recombinant paramyxovirus nucleic acid which is useful for production of wild-type paramyxovirus particles as well as for co-expression of heterologous proteins by reverse genetics. The invention further provides infectious viral particles and/or virus like particles, particularly for the preparation of pharmaceutical compositions or vaccines for use in methods of treating or preventing paramyxovirus infections or other viral infections in a subject.

Accordingly, it was an aim of the current invention to provide an improved method of rescue and propagation of paramyxoviruses. Preferably, the method is highly reproducible, simpler and more efficient than current methods and does not require the presence of products undesirable in a preparation for medical use. Furthermore, the method should reduce the necessity of the rescued virus to adapt to a heterologous host cell (such as a mammalian cell), potentially altering viral characteristics such as sequence, host infectivity and immunogenicity.

The problem underlying the current invention is solved by a method comprising a transfection step for virus rescue and a culturing step for virus propagation, both carried out in the same virus-susceptible cell line. The one-cell methods disclosed herein simplify and accelerate the production of high titers of infectious paramyxovirus particles by reverse genetics. The methods disclosed herein not only eliminate the need for the use of helper cells for paramyxovirus production, but also substantially reduce the time needed from rescue to drug product compared with state of the art methods. In sum, these improvements lead to a more pure drug product in a shorter timeframe.

In the current invention, it was found that the use of a virus-susceptible cell line increased the efficiency of virus rescue compared with previously-disclosed methods and substantially reduced the time needed from transfection of cells to obtaining high viral titers. As shown in the Examples, the rescue of an infectious Newcastle Disease virus (NDV) from a recombinant genomic vector (rNDV) in an avian cell line was highly efficient and reproducible, allowing subsequent rapid propagation of high titers of infectious NDV. Additionally, insertion of coding sequences of heterologous proteins into rNDV is easily performed, and viral rescue with these recombinant vectors resulted in high levels of expression of the heterologous proteins.

BRIEF DESCRIPTION OF THE DRAWINGS

The present invention is further illustrated by the following Figures, Tables, Examples and the Sequence listing, from which further features, embodiments and advantages may be taken. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

In Connection with the Present Invention

FIG. 5 Cloning of foreign genes into the rNDV genomic coding sequence. (A) Autonomous transcription unit (ATU). Each foreign sequence is constructed as an ATU, which comprises a gene-end NDV sequence, a start-end NDV sequence, a kozak sequence and the foreign gene (SEQ ID NO: 143). Conserved nucleotide sequence motifs define the transcriptional gene start with addition of a cap structure to the mRNA and conserved nucleotide sequence motifs that define the gene end and cause the addition of poly(A) to the mRNA in all families. A region of genome RNA between the gene-end and gene-start sequences is found, which is called the intercistronic region. This region is not transcribed into mRNA and can range from two nucleotides to hundreds of nucleotides. For correct and efficient NDV virus replication, the design of the ATU necessarily follows the "rule of 6", based on the observation that efficient replication of NDV RNA requires that the genome size is a multiple of six nucleotides (Peeters, et al., 2000, Archives of Virology, 145(9):1829-1845). (B) An example of an rNDV vector containing an ATU with the coding sequence for a full-length F-protein from a B2 strain of hMPV inserted between coding sequences for NDV proteins P and M (using inserted restriction site FseI).

FIG. 10 Post-transfection kinetics and yield of rNDV-GFP with F-protein mutations in EB66 cells. Comparison of NDV-GFP production with wild-type F-protein cleavage site (trypsin; SEQ ID NO: 1) or introduced furin cleavage sites (furin sites 2, 3, 5 and 6; SEQ ID NOs: 2-5, respectively), or a Y527A point mutation. The GFP-coding nucleotide sequence (SEQ ID NO: 33) was inserted between the P and M NDV proteins using the xxx restriction enzyme. (A) Kinetics of virus rescue from day 2 to day 5 post-transfection as assessed by GFP expression and cytopathic effect. Titers (TCID$_{50}$, indicated in log scale) were determined by measuring cytopathic effect (CPE) under visible light and by GFP production under UV light. Control constructs were rNDV-GFP with a wild-type (trypsin) cleavage site, the test constructs were rNDV-GFP vectors with four different furin cleavage site variations (2, 3, 5, 6) replacing the trypsin cleavage site or a Y527A point mutation. (B) Table showing $TCID_{50}$ on days 3 and 6 post-infection under white light and UV light. (C) $TCID_{50}$ curves of NDV-GFP (trypsin) and NDV-GFP with insertion of furin site 5 with and without daily addition of Trypzean at 0.75 USP/mL after infection.

FIG. 11 The rNDV platform of the invention offers a rapid process from recombinant sequence generation to obtaining an infectious titer of $10^{9.5}$ to $10^{10.5}$ $TCID_{50}$/mL rNDV. (A) Schematic of production timeline; (B) Viral titers observed at day 2 following infection of EB66 cells with rNDV rescued from several of the herein disclosed constructs (see table) and representative coomassie and silver staining of the harvested virus. NDV proteins L, HN, F, P, M and V (a product of editing during P gene transcription) are indicated by arrows.

DETAILED DESCRIPTION OF THE INVENTION

Accordingly, in one aspect, it was an object of the present invention to provide an improved method for production of paramyxoviruses. In a first aspect, the present invention relates to a method of producing infectious paramyxovirus particles comprising the steps of (a) transfecting an avian cell line with a vector comprising a paramyxovirus nucleic acid sequence under T7 control, a T7 RNA polymerase expression vector and three (helper) expression vectors comprising, respectively, paramyxovirus phosphoprotein (P), nucleoprotein (N) and polymerase (L) coding sequences under T7 control; and (b) culturing said transfected avian cell line under conditions favorable for virus propagation. In one aspect, the T7 RNA polymerase expression vector is under the control of a constitutive promoter; e.g., under CMV promoter control. In one aspect, the CMV promoter comprises an enhancer region, such as, e.g., the CMV promoter and enhancer sequence as provided by SEQ ID NO: 35.

in one aspect, the vector comprising a paramyxovirus nucleic acid sequence under T7 control further comprises a T7 promoter sequence and a T7 terminator sequence. In one aspect, the T7 promoter sequence is positioned 5' from the start of the paramyxovirus nucleic acid sequence, particularly immediately 5' from the start of the paramyxovirus nucleic acid sequence. In one aspect, the T7 terminator sequence is positioned 3' from the end of the paramyxovirus nucleic acid sequence, particularly immediately 3' from the end of the paramyxovirus nucleic acid sequence. In a preferred aspect, the T7 promoter sequence has a sequence as defined by SEQ ID NO: 6 and the T7 terminator sequence has a sequence as defined by SEQ ID NO: 7. In a preferred aspect, the vector comprising a paramyxovirus nucleic acid sequence under T7 control further comprises a ribozyme sequence, especially a Hepatitis delta virus ribozyme sequence (HDV Rz) as defined by SEQ ID NO: 8. In one aspect, the HDV Rz sequence is positioned 3' from the end of the paramyxovirus nucleic acid sequence. In a preferred aspect, the HDV Rz sequence is positioned 3' to the end of the paramyxovirus nuclei acid sequence and 5' from the start of the T7 terminator sequence. In one aspect, the vector comprising a paramyxovirus nucleic acid sequence under T7 control comprises 2 G residues or 3 G residues inserted 5' to the paramyxovirus coding sequence.

In one aspect, the transfection step (a) of the invention includes an electroporation step. Electroporation, also known as electropermeabilization, is a technique known in the art of applying electrical pulses to cells to allow the introduction of genetic material, such as DNA, inside of the cell. This process of introducing genetic material is referred to as "transfection" when applied to eukaryotic cells and "transformation" when applied to prokaryotic cells. Electroporation of mammalian cells for transfection purposes can be accomplished in a variety of different ways with readily available protocols and devices, typically by the use of purpose-built electroporators, such as, e.g., the MaxCyte STX® Scalable Transfection System (MaxCyte, Inc.). Electroporators are devices which allow the application of an electrostatic field to a cell solution, typically cells in aqueous solution mixed with the genetic material for transfection of the cell. The mixture is placed into electroporation cuvettes and subject to electrical pulses in the electroporator.

In one aspect, the transfection step (a) of the invention includes the use of chemical transfection reagents. Chemical transfection reagents are positively charged compounds or molecules which complex with the negatively charged nucleic acids to be transfected and which are also attracted to the negatively charged cell membrane. Through a process involving endocytosis and phagocytosis, the complexes pass through the eukaryotic cell membrane and into the nucleus. In a preferred embodiment, the transfection reagents for use in methods of the invention include cationic liposome formulations, such as, e.g., lipofectamine reagents (Invitrogen), or calcium phosphate.

In one aspect, said favorable conditions in the culturing step (b) of the method of the current invention include the addition of trypsin to the culture at regular intervals, for example addition every few hours, addition twice or three times per day, addition once daily, addition every other day, preferably addition once daily. Trypsin cleavage sites are commonly present in viral proteins, particularly viral fusion proteins (F-proteins). The presence of trypsin during propagation of viruses can facilitate the efficient formation of infectious viral particles by aiding in processing of viral proteins, particularly viral F-proteins, and subsequent assembly of the particles, significantly increasing yields. In some cases, as outlined below, mutation of the trypsin cleavage site in F-proteins can eliminate the need for added trypsin during propagation. In a preferred aspect, favorable conditions for virus propagation in the culturing step (b) of the method of the current invention do not include the addition of trypsin to the culture.

In one aspect, transfection step (a) and culturing step (b) of the methods of the invention are carried out fully or in part in a chemically-defined (CD) cell culture medium. Chemically-defined culture media contain defined, highly-controlled and thus traceable components, virtually eliminating inconsistencies between batches that are related to media variability. Chemically-defined culture media are thus desirable for industrial processes, increasing production reliability and improving end-product quality. These advantages can also help reduce regulatory hurdles. In a preferred embodiment, the media for use in the methods of the invention are free from animal-derived components, e.g., sera. An absence of animal-derived components also improves product consistency and can simplify regulatory processes for new pharmaceutical products derived from cultured cells. In one embodiment, the chemically-defined medium is specially formulated for culturing of eukaryotic cell types, especially avian cell types. In a preferred embodiment, the chemically-defined medium is HyClone™ CDM4Avian medium (GE Healthcare Life Sciences).

In one aspect, the method of the current invention, particularly both transfection (a) and culturing (b) steps, is carried out in one eukaryotic cell type, such as a primary eukaryotic cell or a cell line. In one aspect, the eukaryotic

Figure 1:
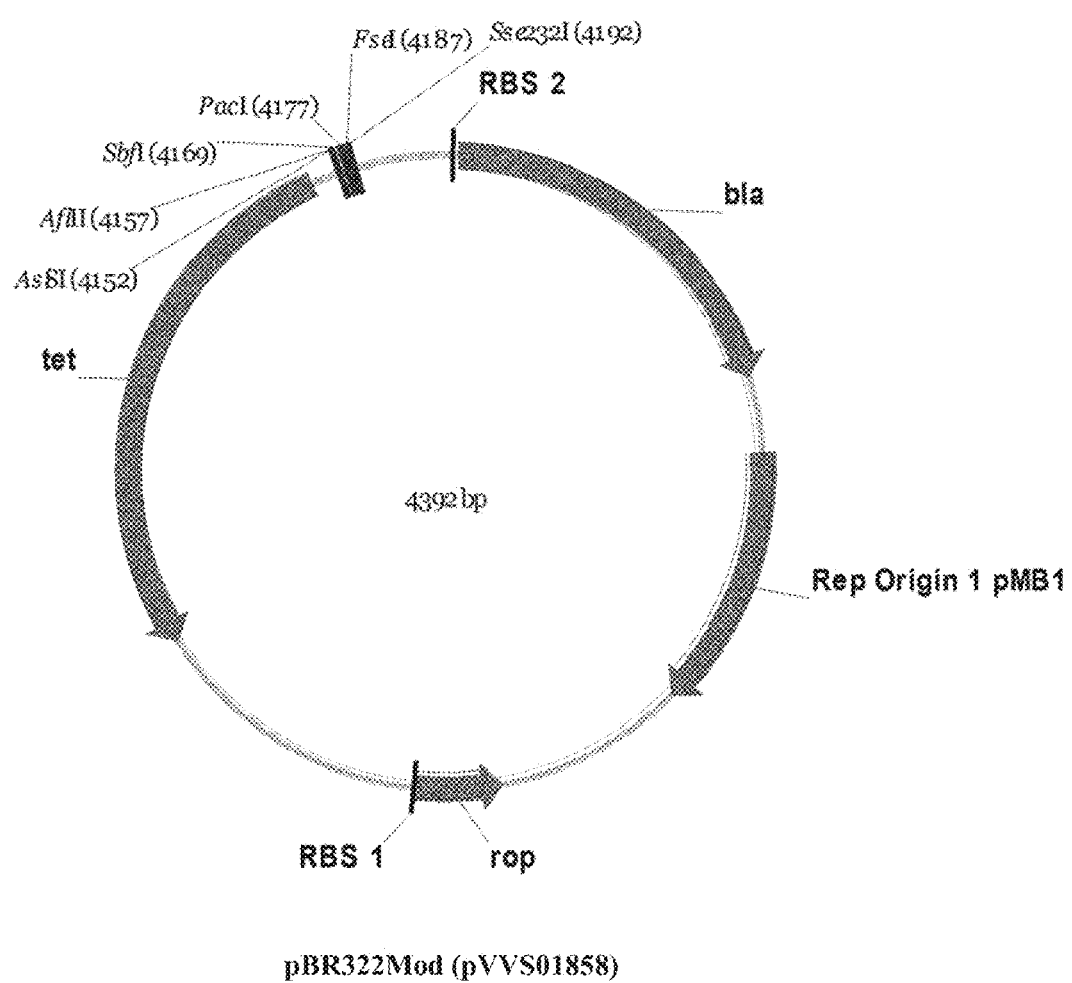
FIG. 1 Map of the modified plasmid of the invention: "pBR322Mod" (pVVS01858). The low-copy-number plasmid pBR322 (SEQ ID NO: 24) was modified by insertion of a linker containing six restriction enzyme sites necessary for NDV genome cloning (Sse232I, FseI, PacI, SbfI, AflII, AsiSI), with half restriction sites on the ends for insertion into the pBR322 double digested with EcoRI and HindIII. The linker was constructed by annealing nucleic acid oligomers oVVS01279 and oVVS01278 (SEQ ID NOs: 9 and 10, respectively) and inserted into EcoRI/HindII double-digested pBR322.

cell may be a yeast cell. In one aspect, the primary eukaryotic cell may be an embryonic cell. In one aspect, the eukaryotic cell may be a mammalian, avian or insect cell line, e.g., a mammalian cell line, such as, e.g. an HEK293 cell line or a Vero cell line. In a preferred aspect, the method of the current invention is carried out in an avian cell line; in particular, in the same avian cell line for both transfection (a) and culturing (b) steps of the methods of the invention. Avian cells are permissive to infection by avian viruses, including avian paramyxoviruses. Susceptibility of the cell line to infection by avian paramyxoviruses is an important feature of the methods disclosed herein. In one aspect, the avian cell line is derived from chicken, turkey, quail, pheasant or duck cells. In one aspect, the cell line is a primary cell line. In one aspect, the cell line is derived from stem cells. In one aspect, the cell line is an immortalized cell line.

In a preferred aspect, the avian cell line is a duck cell line. In one aspect, the duck cell line is an immortalized duck cell line. In a preferred embodiment, the duck cell line of the invention is a continuous diploid cell produced from embryonated duck eggs, such as an EBx cell line as described in WO03/076601A1 and WO08/129058A1, which are incorporated herein by reference in their entirety. Briefly, the EBx cell lines are continuous diploid duck cells which are obtained by isolation, culture and expansion of embryonic stem cells from birds that do not contain complete endogenous proviral sequences or fragments thereof. In a first step, the cells are cultured in complete culture medium containing all factors to support cell growth and in the presence of a feeder layer, supplemented with animal serum and any additional additives as needed. In a second step, the culture medium is modified gradually to finally obtain complete withdrawal of the feeder layer, sera and any additives. This gradual withdrawal "weans" the cells to finally result in an adherent or suspension avian cell line which does not produce replication-competent endogenous retrovirus particles, which is capable of proliferating over a long period of time in a basal medium in the absence of endogenous growth factors, feeder cells and serum. Most preferably, the avian cell line is an EB66 ® cell line, a cell line which is particularly useful for the production of vaccines (Brown and Mehtali, 2010, PDA J Pharm Sci Technol. 64(5):419-25).

In one embodiment, the duck cells are derived from duck retina or embryonic fibroblasts, such as those described in WO2005/042728, which is incorporated herein by reference in its entirety. In a preferred embodiment, the duck cells are an immortalized duck cell line, particularly an AGE1.CR cell line, i.e., AGE1.CR.pIX, or a DuckCelt®-T17 cell line. Particularly, the DuckCelt®-T17 cell line is a cell line with an ECACC accession number of 09070701, 09070702, 009070703, 08060501 or 08060502.

In one aspect, the paramyxovirus nucleic acid sequence is a genomic nucleic acid sequence; e.g., an entire genomic sequence, such as a wild-type genomic sequence. As used herein, the terms "recombinant paramyxovirus nucleic acid sequence" and "paramyxovirus nucleic acid sequence" are used interchangeably and may refer to a paramyxovirus nucleic acid sequence that has been modified to code for an altered (mutated) protein, a paramyxovirus nucleic acid sequence which has been altered strictly for improved expression ("codon optimized") or a wild-type paramyxovirus nucleic acid sequence which has been artificially constructed. In one aspect, the paramyxovirus nucleic acid sequence is a partial genomic nucleic acid sequence. In one aspect, the paramyxovirus nucleic acid sequence is an engineered genomic nucleic acid sequence or partial genomic nucleic acid sequence; i.e., a recombinant nucleic acid sequence. In one aspect, the nucleic acid sequence encodes a chimeric paramyxovirus; i.e., a virus comprising components from two or more viruses. As used herein, genomic sequence shall mean a sequence containing adequate genetic information to generate and pack infectious paramyxovirus particles; i.e., a wild-type or engineered genomic nucleic acid. In one aspect, the nucleic acid sequence may be a wild-type sequence or, alternatively, a sequence which is codon optimized for improved expression. In one aspect, the engineered genomic nucleic acid sequence or partial genomic nucleic acid sequence allows the production of infectious paramyxovirus particles, live-attenuated paramyxovirus particles and/or virus-like particles (VLPs). In one aspect, the VLPs are paramyxovirus VLPs. In a preferred aspect, the VLPs are heterologous VLPs, e.g., VLPs of human metapneumovirus or respiratory syncytial virus.

In one aspect, the paramyxovirus nucleic acid sequence used in the methods of the current invention, particularly in transfection step (a), comprises a paramyxovirus genomic coding sequence in whole or in part. As used herein, a "genomic sequence" or "genomic coding sequence" can be used interchangeably. Also as used herein, "paramyxovirus genomic coding sequence" and "paramyxovirus nucleic acid sequence" can be used interchangeably. These terms refer to a DNA or a cDNA sequence, which contains sufficient genetic information to allow packing of an infectious paramyxovirus particle under rescue conditions as described herein. It should be noted that a viral genome may contain, in addition to protein-coding regions, intervening non-coding regions, e.g., introns. In one aspect, the infectious paramyxovirus encoded by the paramyxovirus genomic coding sequence is a wild-type paramyxovirus, a chimeric paramyxovirus or a recombinant paramyxovirus. In one aspect, the paramyxovirus nucleic acid sequence of the invention is at least 50% identical, 60% identical, 70% identical, 80% identical, at least 85% identical, at least 90% identical, at least 95% identical, especially at least 96%, at least 97%, at least 98%, at least 99% or 100% identical to the wild-type paramyxovirus genomic nucleotide sequence or, preferably, to a paramyxovirus genomic nucleotide sequence which is codon-optimized for expression in a cell of choice.

In one aspect, the paramyxovirus nucleic acid sequence codes for proteins which are at least 85%, at least 86%, at least 87%, at least 88%, or at least 89% identical to the wild-type paramyxovirus proteins, more preferably at least 90%, at least 91%, at least 92%, at least 93%, at least 94%, at least 95% identical to the wild-type paramyxovirus proteins, even more preferably at least 96%, at least 97%, at least 98%, most preferably at least 99% or especially 100% identical to the wild-type paramyxovirus proteins. In particular, the paramyxovirus F-protein may deviate from the wild-type F-protein sequence, particularly with regard to the trypsin cleavage site.

In a preferred aspect, the paramyxovirus nucleic acid sequence contains introduced mutations between the protein-coding regions of the viral genome. In one aspect, the paramyxovirus nucleic acid sequence is modified to contain one or more sites for insertion of heterologous coding sequences, i.e., restriction enzyme sites. In one aspect, the one or more sites for insertion of heterologous coding sequences are located before, after or between the paramyxovirus protein coding sequences. In one aspect, the one or more sites for insertion of heterologous coding sequences are located within the paramyxovirus coding sequences. In a preferred aspect, the sites for insertion of heterologous coding sequences are located between the NP and P coding sequences and/or the P and M coding sequences. In one aspect, the restriction enzyme sites are included between one or more of the protein coding sequences of the paramyxovirus; i.e., between NP and P, between P and M, between M and F, between F and HN and/or between HN and L. In a preferred aspect, the restriction enzyme sites are included between each of the protein coding sequences of the paramyxovirus; i.e., between NP and P, between P and M, between M and F, between F and HN and between HN and L. In one aspect, the modified paramyxovirus nucleic acid sequence contains a sequence for enhancement of translation of inserted heterologous coding sequences, e.g., an internal ribosome entry site (IRES). An internal ribosome entry site (IRES) enables the translation machinery, i.e., the ribosome complex, to initiate translation at sites other than the viral initiation site.

In one aspect, the modified paramyxovirus nucleic acid sequence contains one or more heterologous coding sequences; i.e. coding sequences for one or more foreign antigens or proteins (e.g., foreign genes), particularly antigens from viral pathogens, oncolytic proteins and/or immunomodulating proteins. In a preferred aspect, the heterologous coding sequences from a viral pathogen encode hMPV and/or RSV antigens. In one aspect, the hMPV or RSV antigen is an F protein or an M protein. In one aspect, heterologous coding sequences expressing F and M proteins are contained in the modified paramyxovirus nucleic sequence and can assemble to produce virus like particles; i.e., hMPV or RSV virus like particles (VLPs). In a preferred aspect, the heterologous protein is an hMPV or RSV fusion protein (F-protein). In one aspect, the F-protein is from an hMPV virus, particularly an A1, A2, B1 or B2 strain of hMPV virus. In a preferred aspect, the hMPV F-protein is selected from the group consisting of SEQ ID NOs: 17-20, or an immunogenic protein with at least 95% sequence identity to any one of the amino acid sequences provided by SEQ ID NOs: 17-20. In a preferred aspect, the hMPV F-protein is a soluble F-protein, particularly a soluble F-protein modified to be stabilized in a pre-fusion or post-fusion configuration, especially a pre-fusion configuration. In one aspect, the RSV F protein is selected from any strain of RSV. In a preferred aspect, the F-protein is a protein with the amino acid sequence as provided by SEQ ID NOs: 21, or a protein with at least 95% sequence identity to the amino acid sequence of SEQ ID NO: 21.

In one aspect, the heterologous protein is an hMPV or RSV matrix protein (M-protein). In one aspect, the M-protein is from an hMPV virus, particularly an A1, A2, B1 or B2 strain of hMPV virus. In a preferred aspect, the hMPV M-protein comprises the amino acid sequence as provided by SEQ ID NO: 22, or an immunogenic variant with at least about 95% sequence identity to SEQ ID NO: 22. In one embodiment, the M-protein is from an RSV virus. In a preferred aspect, the RSV M-protein comprises the amino acid sequence as provided by SEQ ID NO: 23, or an immunogenic variant with at least about 95% sequence identity to SEQ ID NO: 23.

In one aspect, the modified paramyxovirus nucleic acid sequence contains coding sequences for both hMPV and RSV F-proteins. In one aspect, the heterologous F-protein is a wild-type F protein. In one aspect, the heterologous F-protein is a soluble F protein; i.e., modified to omit at least the transmembrane region and cytoplasmic tail of the F-protein. In one aspect, the F-protein or soluble F-protein is modified to express a stabilized post-fusion conformation. In a preferred aspect, the F-protein or soluble F-protein is modified to form a stabilized pre-fusion conformation. In a preferred aspect, the F-protein or modified F-protein is an hMPV F-protein. In a preferred aspect, the foreign coding sequences are inserted into the paramyxovirus nucleic acid sequence as additional transcriptional units (ATU). In one aspect, an ATU according to the invention comprises or consists of a gene start sequence (GS) the foreign gene coding sequence, and the paramyxovirus gene end (GE) sequence. In a preferred aspect, the ATU is inserted into a multicistronic system which allows the independent expression of the foreign gene(s) by the use of Internal Ribosome Entry Site(s) (IRES) or other such expression systems.

In one aspect, the one or more heterologous coding sequences are for oncolytic proteins. In one aspect, the oncolytic proteins promote selective targeting of tumor cells in vivo or in vitro. In one aspect, the oncolytic proteins reduce viral clearance from the body, e.g., the body of a mammalian or avian subject, especially a human subject. In one aspect, the oncolytic proteins enhance tumor cell killing. In a preferred aspect, the oncolytic proteins are proteins known in the art to enhance tumor cell killing, i.e., apoptosis, e.g., an inducible heat shock protein (hsp), such as, e.g., hsp-70 or gp96. In one aspect, the oncolytic proteins are secreted toxins or prodrug convertases. In one aspect, the one or more heterologous coding sequences are selected from immunomodulating proteins. Immunomodulation is a strategy used in cancer therapy as a way of harnessing the immune system to attack and weaken the defenses of malignant cells. In this regard, preferred immunomodulating proteins are, for example, interferons (IFN), such as type I, type II or type III interferons and interleukins, such as especially IL-2. In one aspect, the foreign protein may be a protein which can inhibit tumor cell checkpoint inhibitors such as PD-1, PD-L1 or CTLA-4. In one aspect, the foreign protein is an antibody or an antibody fragment having an anti-tumor effect.

In one aspect, the avian paramyxovirus of the invention is selected from any of avian paramyxoviruses (APMV) 1 to 13, also known as Avian avulaviruses 1 to 13. In a preferred aspect, the avian paramyxovirus is a Newcastle Disease Virus (NDV; APMV-1); i.e., the paramyxovirus nucleic acid sequence is an NDV nucleic acid sequence. In one aspect, the NDV is a lentigenic strain of NDV, especially a LaSota or Hitchner B 1 strain. A lentigenic strain is defined as having relatively lower virulence in birds. In one aspect, the NDV genomic coding sequence is from a moderate to high virulent strain of NDV, i.e., a mesogenic or velogenic strain, such as, e.g., AF2240. In one aspect, the NDV strain is an oncolytic strain; i.e., a strain with capacity to selectively induce apoptosis in tumors or cancer cells in vivo or in vitro. In one aspect, the oncolytic strain is a LaSota strain of NDV. In a preferred aspect, the oncolytic strain is the highly virulent AF2240 strain of NDV. In one aspect, the F-protein of the recombinant paramyxovirus nucleic acid sequence is modified, particularly to comprise a furin cleavage site instead of a trypsin site, to enhance tumorigenicity. In one aspect, the F-protein of the recombinant paramyxovirus nucleic acid comprises a mutation of a conserved tyrosine residue, especially an alanine substitution. In one aspect, the paramyxovirus nucleic acid sequence is genetically modified to increase virus thermostability. In one embodiment, the NDV nucleic acid sequence of the invention encodes a wild-type NDV genome, a chimeric NDV genome, a recombinant NDV genome or a virus-like particle comprising NDV elements; especially a recombinant NDV (rNDV or rNDV-FL) as defined by SEQ ID NO: 16.

In one aspect, the NDV obtainable by the method of the invention is used as a virotherapeutic agent for cancer treatment; i.e., is oncolytic. In one aspect, the oncolytic NDV has a direct role in tumor cell killing. In one aspect, the oncolytic NDV has a mode of action including selective targeting of tumor cells, reduction of virus clearance from the subject's body and/or improved tumor cell killing. In one aspect, the oncolytic NDV is engineered to have enhanced therapeutic activity. In one aspect, the enhanced therapeutic activity of the oncolytic NDV includes expression of secreted toxins, prodrug convertases and/or proteins activating antitumor immunity. In one aspect, the anti-tumor effect of the NDV may be potentiated by the route of administration of the NDV particles (e.g., intratumor, intravenous, etc.) or by co-administration with other agents.

In one aspect, the recombinant NDV of the invention comprises an NDV F-protein with a modified protease cleavage site. The presence of a furin site (instead of a trypsin site) in the F-protein of some NDV strains correlates with higher virulence. This effect is likely due to more favorable processing of viral proteins for assembly of infectious particles. This modification in a recombinant NDV F-protein serves to facilitate the cleavage of the NDV F protein, which optimizes virus release from cells and can substantially increase virus yields during production. Additionally, this feature eliminates the need for trypsin during production, which must otherwise be removed during manufacture. The improved cleavage of the F-protein containing a furin site also serves to facilitate $TCID_{50}$ reading (visible CPEs). In one embodiment, the wild-type protease (trypsin) cleavage site of the recombinant NDV F-protein (SEQ ID NO: 1) is modified to 112 RRQKR1L 117, from Beaudette C strain ("Site 2", SEQ ID NO: 2; Panda et al., 2004, Microbial Pathogenesis, 36(1):1-10). In one embodiment, the protease cleavage site is modified to 112 RRRRR1L 117 from avian metapneumovirus ("Site 3", SEQ ID NO: 3; Biacchesi et al., 2006, J. Virol. 80(12): 5798-5806). In one embodiment, the protease cleavage site is modified to 112 RRQRR1F 117 from virulent and mesogenic NDV strains ("Site 5", SEQ ID NO: 4; Leeuw et al., 2003, J. Gen. Virol. 84:475-484). In one embodiment, the protease cleavage site is modified to 112 KKRKR1L 117, which is derived from the furin cleavage site of RSV ("Site 6", SEQ ID NO: 5; Rawling, et al., 2008, J. Virol., 82(12):5986-5998). In a preferred aspect, the trypsin cleavage site of NDV (SEQ ID NO: 1) is replaced with a furin cleavage site, particularly a furin cleavage site selected from the group consisting of SEQ ID NOs: 2-5.

In one embodiment, the F-protein of the recombinant NDV virus of the invention comprises a Y527A mutation. Tyrosine 527 is a highly conserved amino acid in the cytoplasmic domain of the NDV F-protein. A single Y527A point mutation, when introduced into the F-protein of LaSota NDV, resulted in a hyperfusogenic virus with increased replication and immunogenicity (Manoharan, et al., 2016, J. Gen. Virol., 97:287-292). In a preferred embodiment, the Y527A mutation is effected by replacing the codon TAC (Tyr) by GCC (Ala) in the position corresponding to amino acid 527 in the NDV F protein coding sequence.

In one aspect of the invention, the NDV nucleic acid sequence further comprises at least one nucleic acid sequence encoding at least one heterologous antigen. In one embodiment, the heterologous antigen is a wild-type or modified antigen from a human pathogen. In one aspect, the human pathogen is a respiratory pathogen, particularly a respiratory virus. In a preferred aspect, the human pathogen is a human metapneumovirus (hMPV) or a respiratory syncytial virus (RSV), most preferably an hMPV, especially an A1, A2, B1 or B2 strain of hMPV. In one aspect, the heterologous antigen is an F-protein, preferably an hMPV or RSV F-protein, especially an hMPV F-protein. In one aspect, the F-protein is a full-length wild-type F-protein. In one aspect, the F-protein is a soluble mutant lacking the transmembrane and cytoplasmic portions. In one aspect, the soluble F-protein mutant is further modified to form a stabilized pre-fusion or post-fusion form. In one aspect, the heterologous antigen is an M protein from hMPV or RSV. In a preferred aspect the heterologous antigen is selected from the group comprising or consisting of hMPV F-proteins, e.g., as provided by SEQ ID NO: 17-20, RSV F-proteins, e.g., such as provided by SEQ ID NO: 21, hMPV M proteins, e.g., as provided by SEQ ID NO: 22 and RSV M proteins, e.g., as provided by SEQ ID NO: 23. In a preferred aspect, the nucleic acid sequence encoding the at least one heterologous antigen is codon optimized.

In general, codon optimization refers to the use of the degeneracy of the genetic code to change bases within codons in a given nucleic acid sequence such that protein expression is more favorable (e.g., in a particular cell type), but to maintain the amino acid sequence of the protein. Codon optimization addresses one or more parameters that are critical to transcription, translation and/or protein folding. In one aspect, the nucleic acid sequences provided by the invention, i.e., the paramyxovirus nucleic acid sequences and/or the nucleic acid sequences encoding heterologous proteins, are codon optimized. In one aspect, the nucleic acid sequence is optimized by the use of an algorithm, e.g., such as those provided by GenScript (GS) or GeneArt (GA). In one aspect, the optimized nucleic acid sequence is modified to contain more CG (also referred to a CpG) dinucleotide pairs than the wild-type sequence; e.g., more than 20% CG dinucleotide pairs in the modified sequence, more than 25%, more than 30%, especially at least 33%. In one aspect, the optimized nucleic acid sequence is modified to contain less CG nucleotide pairs than the wild-type sequence; e.g., less than 20% CG dinucleotide pairs in the modified sequence, less than 10%, less than 5%, especially less than 1%, preferably 0%. In one aspect, the optimized nucleic acid sequence contains a substitute element from a heterologous protein. In a preferred aspect, the substitute element is a signal peptide.

In one aspect, the nucleic acid sequence encoding the heterologous protein is placed between the coding sequences for NDV NP and P proteins, between the coding sequences for NDV P and M proteins, between the coding sequences for NDV M and F proteins, between the coding sequences for NDV F and HN proteins or between the coding sequences for NDV HN and L proteins. In one aspect, the nucleic acid sequence encoding the heterologous protein is placed in the recombinant NDV genome vector by use of restriction sites introduced into the recombinant NDV vector, preferably the recombinant NDV defined by SEQ ID NO: 16, i.e., restriction sites AscI (NP/P), FseI (P/M), MluI (M/F), PacI (F/HN) and SfiI (HN/L). Restriction sites are well-known in the art and can be identified readily by reference to sources such as, e.g., Addgene, an online plasmid repository (addgene.org/mol-bio-reference/restriction-enzymes/) and a wide range of restriction enzymes are available commercially.

In one aspect, the method of the invention also comprises at least one purification step following culturing step (b). In a preferred aspect, the at least one purification step comprises a filtration step. In a preferred embodiment, the filtration step removes larger viral particles while retaining smaller viral particles. Such filtration steps are outlined, for example, in WO2016/156613A1, which is incorporated herein in its entirety by reference.

In one aspect, the method of the invention is followed by an inactivation step, preferably a formaldehyde inactivation step. That is, following propagation of infectious viral particles, either before, during or after further purification steps, the virus particles are inactivated, i.e., rendered non-infectious. In one aspect, the inactivation step may be accomplished by any method known in the art, such as by application of heat or radiation or by chemical inactivation, e.g., by use of formaldehyde. In a preferred aspect, the inactivation is carried out with formaldehyde.

In one aspect, the method of the current invention is used for the manufacture of a composition for immunization against a virus infection. In one aspect, the virus infection is caused by an avian paramyxovirus, especially a Newcastle Disease virus. In one aspect, the virus infection may be caused by any viral pathogen, preferably a pathogen infecting birds, mammals or, most preferably, humans. In a further aspect, the virus infection is caused by a human respiratory viral pathogen. In a preferred aspect, the virus infection is caused by an hMPV virus or an RSV virus, most preferably an hMPV virus.

In one aspect, the current invention provides a pharmaceutical composition comprising the virus particles obtainable or obtained by the methods disclosed herein for treating and/or preventing an infection, such as e.g. an NDV, hMPV or RSV infection. As used herein, the term "preventing" shall mean "protecting from", e.g., completely eliminating the development of signs and symptoms of disease following exposure to a pathogen or greatly reducing the severity, duration or serious sequelae of the disease. A pharmaceutical composition is a composition intended for use in the pharmaceutical field or as pharmaceutic. It may optionally contain any pharmaceutically acceptable carrier or excipient, such as buffer substances, stabilizers or further active ingredients, especially ingredients known in connection with pharmaceutical compositions and/or vaccine production. In general, the nature of the excipients will depend on the particular mode of administration being employed. Such carriers may include, but are not limited to, saline, buffered saline, dextrose, water, glycerol, ethanol and combinations thereof. In a preferred aspect, the pharmaceutically acceptable carrier or excipient is an adjuvant as outline in greater detail below. The formulation should suit the mode of administration. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically neutral carriers, pharmaceutical compositions to be administered can contain minor amounts of non-toxic auxiliary substances, such as wetting or emulsifying agents, preservatives, and pH buffering agents and the like.

In a preferred embodiment the pharmaceutical composition is a vaccine composition, e.g., a vaccine. Preferably, such vaccine composition is conveniently in injectable form. Conventional adjuvants may be employed to enhance the immune response. The pharmaceutical composition or vaccine of the present invention may be used to protect a bird or a mammal, especially a human, susceptible to infection, by means of administering said pharmaceutical composition or vaccine via a systemic or mucosal route. These administrations may include injection via the intramuscular, intravenous, intraperitoneal, intradermal or subcutaneous routes; or via mucosal administration to the oral/alimentary, respiratory or genitourinary tracts. Although the vaccine of the invention may be administered as a single dose, components thereof may also be co-administered together at the same time or at different times. In the case of flock vaccination (i.e., to poultry), the vaccine of the invention may be administered in a variety of ways, e.g., in ovo; through intramuscular or subcutaneous injection; by wing stab; by feather follicle introduction; by nasal, ocular, cloacal or oral routes; by introduction to drinking water; or by spray, e.g., using an atomizer. In one aspect, the pharmaceutical composition comprises at least $10^1$ viral particles, at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$ viral particles, preferably between $10^6$ and $10^{14}$ viral particles. In one aspect, the final dose administered to a subject is about $10^6$ particles/kg body weight of subject, about $10^7$ particles/kg, about $10^8$ particles/kg, about $10^9$ particles/kg, about $10^{10}$ particles/kg, about $10^{11}$ particles/kg, about $10^{12}$ particles/kg, about $10^{13}$ particles/kg body weight of subject, preferably between about $10^9$ and $10^{12}$ particles/kg body weight of subject.

In one embodiment, the pharmaceutical composition further comprises an adjuvant or immunostimulatory compound or substance. Adjuvants are substances that stimulate, enhance or enable a protective immune response against an antigen. The choice of a suitable adjuvant to be mixed with the viral particles made using the methods of the invention is within the knowledge of the person skilled in the art. Suitable adjuvants include an aluminium salt such as aluminium hydroxide or aluminum phosphate, but may also be other metal salts such as those of calcium, magnesium, iron or zinc, or may be an insoluble suspension of acylated tyrosine, or acylated sugars, cationically or anionically derivatized saccharides, or polyphosphazenes. The use of an aluminium hydroxide and/or aluminium phosphate adjuvant is particularly preferred, and antigens are generally adsorbed to these salts. Preferably, aluminium hydroxide is present at a final concentration of 0.15%. A useful aluminium phosphate adjuvant is amorphous aluminium hydroxyphosphate with PO 4/Al molar ratio between 0.84 and 0.92. Another adjuvant useful in the current invention is an aluminium salt that is able to provide an aqueous composition having less than 350 ppb heavy metal based on the weight of the aqueous composition, particularly an aluminium hydroxide containing less than 1.25 ppb Cu based on the final pharmaceutical composition comprising the virus, according to WO2013/083726A1, which is incorporated herein by reference in its entirety. The purity of alum adjuvant can influence the stability of viral vaccine compositions (Schlegl, et al., 2015, Vaccine 33:5989-5996). A further useful aluminium-based adjuvant is ASO4, a combination of aluminium hydroxide and monophosphoryl lipid A (MPL).

Immunostimulatory compounds or substances (adjuvants) may be used in compositions of the invention. In a preferred embodiment, the immunostimulatory compound in pharmaceutical compositions according to the present invention is selected from the group of polycationic substances, especially polycationic peptides, immunostimulatory nucleic acids molecules, preferably immunostimulatory deoxynucleotides, especially oligo(dIdC)$_{13}$ (SEQ ID NO: 25), peptides containing at least two LysLeuLys motifs, especially peptide KLKLLLLLKLK (SEQ ID NO: 26), neuroactive compounds, especially human growth hormone, aluminium hydroxide, aluminium phosphate, Freund's complete or incomplete adjuvants, or combinations thereof. Preferably, the immunostimulatory substance is a combination of either a polycationic polymer (such as e.g., polyarginine) and immunostimulatory deoxynucleotides or of a peptide containing at least two LysLeuLys motifs and immunostimulatory deoxynucleotides, preferably a combination of KLKLLLLLKLK (SEQ ID NO: 26) and oligo(dIdC)$_{13}$ (SEQ ID NO: 25); i.e., IC31®. In one aspect, the immunostimulatory substances are oil-in-water or water-in-oil emulsions, MF59, aluminium salts, Freund's complete adjuvant, Freund's incomplete adjuvant, neuroactive compounds, especially human growth hormone, or combinations thereof.

In one embodiment, the pharmaceutical composition may comprise a stabilizer. The term "stabilizer" refers to a substance or vaccine excipient which protects the immunogenic composition of the vaccine from adverse conditions, such as those which occur during heating or freezing, and/or prolongs the stability or shelf-life of the immunogenic composition in a stable and immunogenic condition or state. Examples of stabilizers include, but are not limited to, sugars, such as sucrose, lactose and mannose; sugar alcohols, such as mannitol; amino acids, such as glycine or glutamic acid; and proteins, such as human serum albumin or gelatin.

TABLE A-1

Terms and abbreviations

| | |
|---|---|
| aa | Amino acid |
| ATU | Autonomous Transcriptional Unit |
| CB | Cell Boost |
| CD Avian | CDM4 defined avian medium (Hyclone) |
| Cfu | colony forming units |
| CMV | Cytomegalovirus |
| CPE | Cytopathic effect |
| DNA | Deoxyribonucleic acid |
| Dpi | Day post infection |
| DS | Drug substance |
| FBS | Fetal bovine serum |
| FGT | fragment |
| GFP | Green Fluorescent Protein |
| Gln | Glutamine |
| GMEM | Glasgow's Minimal Essential medium |
| GRO-I | EX-CELL EBx-GRO-I |
| hMPV | human Metapneumovirus |
| IC | Internal control |
| LB | Luria-Bertani medium |
| MOI | Multiplicity of infection |
| MVC/ml | Million viable cells per ml |
| MVSB | Master virus seed bank |
| NDV | Newcastle Disease Virus |
| NDV FL | NDV full length recombinant plasmid aka rNDV |
| Nt | nucleotide |
| PCR | Polymerase Chain Reaction |
| PD | Process development |
| Pfu | Plaque forming unit |
| PRO-I | EX-CELL EBx-PRO-I |
| PS | Protamine sulfate |
| RE | Restriction enzyme |
| RNA | ribonucleic acid |
| RSV | Respiratory Syncytial virus |
| TB | Terrific-Broth |
| TCID50 | 50% tissue culture infectious dose |
| TOI | Time of infection |
| TPCK | N-tosyl-L-phenylalanine chloromethyl ketone |
| USP | Upstream process |
| WCB | Working cell bank |
| WVSB | Working virus seed bank |
| WP | Work package |

EXAMPLES

Example 1 Generation of a Recombinant NDV Full-Length Genome Plasmid and Helper Plasmids for Viral Rescue The NDV genome is a single-stranded negative-sense (anti-sense) RNA, which is non-segmented; i.e., follows a sequential pattern of gene expression. The genome of NDV is 15,186 nucleotides long (Krishnamurthy and Samal, 1998, J Gen Virol 79:2419-2424 and de Leeuw and Peeters, 1999, J Gen Virol 80:131-136) and contains six genes, which encode nucleocapsid protein (NP), phosphoprotein (P), matrix protein (M), fusion protein (F), hemagglutinin protein (HN) and large protein (L). Additionally, V and W proteins can be produced by RNA editing during P gene transcription (Steward et al., 1993, J Gen Virol 74:2539-2547).

One aspect of NDV and other negative-sense RNA viruses is that naked RNA alone is not infectious. In order to "rescue" infectious viral particles from a host cell transfected with a recombinant virus expression vector, the presence of components of the viral ribonucleoprotein complex (RNP), namely NP, P, and L proteins, is essential to initiate the first round of RNA synthesis. Therefore, the current technique of virus rescue for negative-sense RNA viruses by reverse genetics involves co-transfection into permissive cells of a vector containing the viral genome (rNDV), under the control of a T7 promoter, along with helper plasmids expressing NP, P, and L proteins. The T7 RNA polymerase is provided herein by an expression plasmid (also a "helper" plasmid) under constitutive expression which is transfected together with the other plasmids into the host cell. This co-transfection results in reconstitution of the RNP complex inside the cell, viral RNA genome transcription and translation and the recovery ("rescue") of the full virus. From this step onwards, the viral cycle can proceed naturally, i.e., by infection of the host cell, and recombinant virions, encapsidating the modified genome, can be propagated and purified, if desired.

The aim of the work described in this example was to provide a vaccine platform based on an exemplary avian paramyxovirus, Newcastle Disease virus (NDV). Following is described the steps for cloning the NDV LaSota full-length genome into a single plasmid and the helper plasmids necessary for NDV rescue. Briefly, herein were generated 1) a plasmid carrying a recombinant NDV full-length genome under T7 control, modified by the insertion of unique restriction sites between each gene-coding sequence, 2) helper plasmids necessary to start the virus replication cycle, i.e., NP, P and L proteins of NDV and 3) a helper expression plasmid constitutively expressing T7 polymerase. The expression system described herein comprises a modified recombinant NDV nucleic acid sequence which allows insertion of foreign genes of interest in different positions in rNDV nucleic acid. The rNDV may be used to rescue wild-type NDV virus particles or to express or deliver foreign proteins or antigens of interest. The expression of heterologous proteins of interest as vaccine antigens is enabled by insertion of nucleic acid sequences encoding for them. The level of expression of heterologous proteins may be modulated depending on their position within the rNDV vector and the insertion of optional expression-enhancing sequences such as, e.g., IRES sequences.

Materials and Methods

TABLE 1

Enzymes, buffers, media and reagents

| Enzyme | Provider | Ref# |
|---|---|---|
| T4 DNA Ligase (HC) 500 u | Promega | M1794 |
| Buffer Cut smart | New England Biolabs (NEB) | B7204S |
| Buffer 1.1 | NEB | B7201S |
| Buffer 2.1 | NEB | B7202S |
| Buffer 3.1 | NEB | B7203S |
| Buffer tango | Thermo Scientific | BY5 |
| AsiSI | NEB | R0630L |
| AflII | NEB | R0520L |
| SbfI | NEB | R3642S |
| PacI | NEB | R0547L |
| FseI | NEB | R0588L |
| MluI-HF | NEB | R3198S |
| SfiI | NEB | R0123S |
| AscI | NEB | R0558S |
| MreI (Sse232I) (10 U/µL) | Thermo Scientific | ER2021 |
| Platinum Taq Hifi | Life Technologies | 11304011 |
| Prime star Max | NEB | TAKR0 45A |
| Shrimp Alkaline Phosphatase (rSAP) | NEB | M0371 |
| Maxcyte EP buffer | Maxcyte, Inc. | B201-100 |
| Hyclone CDM4Avian | GE Healthcare Life Science | SH31036.01 |
| L-Glutamine (200 mM) | Ozyme | BE17-605E |
| Trypzean | Sigma-Aldrich | T3568 |

Bacterial Strains Used for Plasmid Construction and Amplification

One Shot® MAX Efficiency® DH5aTm-T1 R Competent Cells (Life Technologies, catalog number: 12297016), F-φ80lacZΔM15 Δ(lacZY A-argF)U169 recA1 endA1 hsdR17(rk–, mk+) pho A supE44 relA1 tonA (confers resistance to phage T1).

JM110 Competent Cells (Agilent Technologies, Catalog #200239), JM110 Genotype: rpsL (Strr) thr leu thi-1 lacY galK galT ara tonA tsx dam dcm supE44 Δ(lac-proAB) [F' traD36 proAB lacIqZΔM15]. (Genes listed signify mutant alleles. Genes on the F' episome, however, are wild-type unless indicated otherwise).

Techniques for plasmid generation and sequence verification

All restriction enzyme digestions and ligations, as well as sequencing for control purposes, were done using techniques well-known in the art and enzymes and buffers as listed in Table 1. Primers for sequencing are provided by SEQ ID NOs: 43-136. Plasmids were amplified by transforming competent cells using manufacturers' protocols and purification was done using kits. All plasmids generated were checked for correctness by both restriction mapping and sequencing using standard protocols.

Construction of a modified pBR322 vector with a multiple cloning site (pBR322Mod a.k.a. pVVS01858)

The cloning vector pBR322 (SEQ ID NO: 24) was modified by insertion of a double-stranded nucleotide linker carrying all RE sites necessary for NDV genome cloning including Sse232I, FseI, PacI, SbfI, AflII and AsSI. The linker was constructed by annealing primers oVVS01279 and oVVS01278 (SEQ ID NOs: 9 and 10, respectively) and inserting the resulting double-stranded nucleotide into the EcoRI/HindII double-digested pBR322 plasmid (4330 bp) by virtue of half EcoRI and HindII sites at the ends of the annealed linker. The resulting pBR322Mod plasmid is shown schematically in FIG. 1, with the inserted MCS at the top left, indicating the relative positions of the restriction sites.

Figure 2:
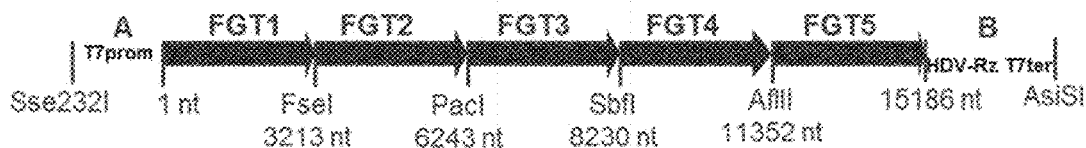
FIG. 2 Recombinant NDV genomic coding sequence for rescue of infectious NDV particles also allowing insertion of heterologous coding sequences. (A) Construction of a recombinant NDV cDNA clone encoding the complete 15,186 nucleotide (nt) genome of the LaSota NDV strain with inserted restriction sites was performed by synthesis of five individual DNA fragments (GeneArt), which were cloned into pBR322Mod: Fragment 1 (FGT1) (A-1-3238 nt; SEQ ID NO: 11); FGT2 (3213-6242 nt; SEQ ID NO: 12); FGT3 (6243-9327 nt; SEQ ID NO: 13); FGT4 (9328-11351 nt; SEQ ID NO: 14) and FGT5 (11352-15186-B; SEQ ID NO: 15). The fragments were cloned sequentially into pBR322Mod (pVVS01858) using standard cloning procedures. The sequence of T7 polymerase promoter (SEQ ID NO: 6) was added at the 5' terminus of FGT1 ("A" element in FGT1) and the sequence of the hepatitis delta virus ribozyme sequence (HDV Rz; SEQ ID NO: 8) and T7 terminator (SEQ ID NO: 7) were added at the 3' terminus of FGT5 ("B" element in FGT5). (B) Mutations were introduced into each intergenic region to create restriction enzyme sites (RE) between NDV protein coding sequences, allowing the insertion of coding sequences of foreign antigens into any desired intergenic region. The indicated RE sites within the NDV L protein coding region mark the ends of FGT4 and FGT5, which were used for cloning purposes. (C) Restriction enzymes sites in the constructed rNDV genome to facilitate cloning of inserts between NDV protein coding sequences. The table shows the identity and relative position of each restriction site as well as the mutations introduced for their insertion. The wild-type and mutant sequences of RE-5 (SfiI) are denoted as SEQ ID NOs: 137 and 138, respectively. (D) A frameshift mutation which was identified in the NDV L-protein coding sequence following splicing of FGTs 1-5 into pBR322Mod and also in the NDV L protein helper plasmid. The constructed helper L protein coding sequence "pVVS01861-Helper-prot. L NDV" (SEQ ID NOs: 139, 142) is aligned with the correct nucleotide and amino acid sequences of "PVVS01927-pClneo-L JLS)") (SEQ ID NOs: 140, 141). The frameshift resulted in failed rescue due to the 30 amino acid mutation introduced in the L protein by the frameshift mutation. To correct the frameshift in the rNDV and the NDV L protein helper plasmid, a 525 bp fragment (SEQ ID NO: 36) which contained a frame shift correction, was inserted between KpnI-KpnI restriction sites of the constructs. The resulting corrected final rNDV sequence (also referred to herein as "rNDV-FL") is provided by SEQ ID NO: 16. (E) Schematic illustration of two possible alternatives for introduction of two foreign antigen coding sequences into the engineered rNDV vector, allowing production of a bivalent vaccine or the generation of VLPs. In the first example, Antigen 1 and Antigen 2 are inserted between coding sequences for NDV proteins NP and P (using the introduced AscI restriction site) and between proteins P and M (using the introduced FseI restriction site), respectively. In the second example, Antigen 1 and Antigen 2 are inserted between coding sequences for NDV proteins P and M (using the introduced FseI restriction site) and proteins M and F (using the introduced MluI restriction site), respectively, each foreign antigen being preceded by an internal ribosome entry site (IRES) allowing multicistronic translation.
Figure 2:
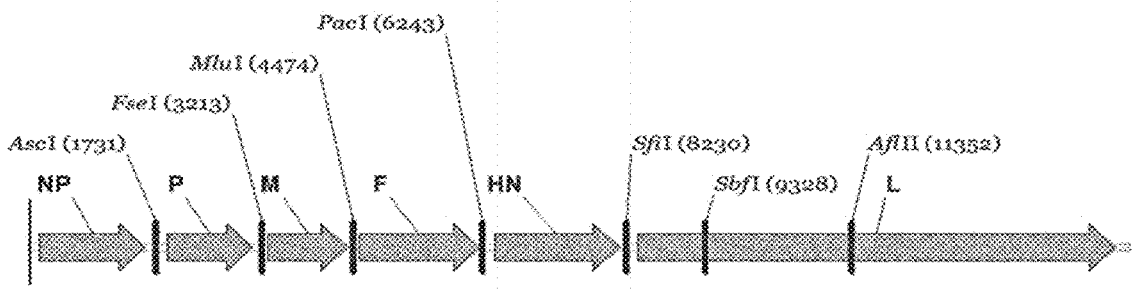
Figure 2:
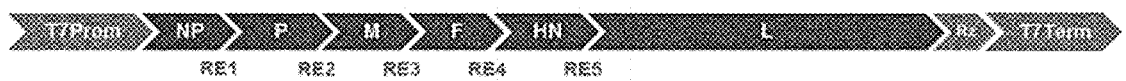
Figure 2:
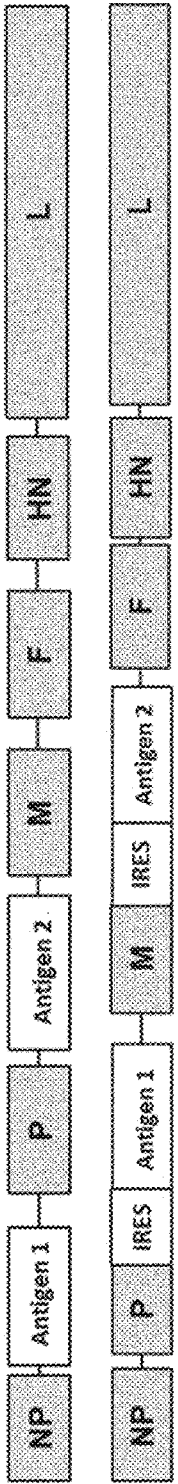

Design and construction of a recombinant NDV full length (NDV-FL a.k.a. rNDV and rNDV-FL) genome expression vector with sites for insertion of heterologous coding sequences Construction of an NDV cDNA clone encoding the complete 15,186 nucleotide NDV genome was undertaken using the sequence of LaSota strain (Accession No: AF077761) as a reference. In the final rNDV expression vector, as shown in FIG. 2A, the NDV coding sequence contained introduced restriction sites, the T7 polymerase promoter sequence was added at the 5' terminus of the NDV genome and the hepatitis delta virus ribozyme (HDV Rz) and T7 terminator sequences were added at the 3' terminus of the NDV sequence (Nakaya et al., 2001, supra). The full-length recombinant NDV expression plasmid (rNDV) was obtained by the digestion, ligation and insertion into pBR322Mod of five individual DNA fragments (FGT1-5; synthesized by GeneArt as follows: FGT1 (T7 promoter sequence plus 1-3209nt of NDV; "A-3209"; SEQ ID NO: 11), FGT2 (3210-6242nt of NDV; SEQ ID NO: 12), FGT3 (6243-9323 nt of NDV; SEQ ID NO: 13), FGT4 (9324-11355 nt of NDV; SEQ ID NO: 14) and FGT5 (11356-15186 of NDV plus HDV-Rz plus T7 terminator; "11356-15186-B"; SEQ ID NO: 15). The restriction sites, which facilitate insertion of heterologous coding sequences into the NDV genome, were inserted between the coding sequences of each of the NDV proteins; i.e., between NP and P, P and M, F and HN and HN and L coding sequences by design of synthetic nucleotide sequences, as shown in FIG. 2B. FIG. 2C shows the placement of the five inserted restriction sites (RE1-RE5) relative to the protein coding sequences of the NDV genome and the introduced sequence mutations for each one. FIG. 2E provides two possible constructs containing coding sequences for heterologous antigens, either without or with an internal ribosome entry site (IRES).

Construction of helper plasmids for virus rescue

Briefly, the helper plasmids were constructed by insertion of coding sequences for NP, P and L proteins of NDV (SEQ ID NOs: 39, 40 and 41, respectively) or T7 RNA polymerase (SEQ ID NO: 42) into pCIneo (SEQ ID NO: 38). The plasmid pCIneo (Promega) is a constitutive mammalian expression vector for transient or stable transfection, which comprises the human cytomegalovirus (CMV) immediate-early enhancer/promoter region (SEQ ID NO: 38).

Sequence analysis and correction

Sequence analysis of the full length cDNA rNDV as constructed above and the NDV L protein helper plasmid both showed 100% identity with the reference sequence (AF077761); however, virus rescue attempts using the rNDV were not successful. When the sequence of the recombinant L-protein helper (see FIG. 2D: "pVVS1861-Helper-prot L NDV") was compared with the sequence of a reference helper plasmid containing an L-protein coding sequence (FIG. 2D: "pVVS01927-pCIneo-L JLS"); kindly provided by Ben Peeters), it was determined that the full-length cDNA rNDV (as well as the L protein in the helper plasmid) had a double frameshift in the coding sequence for the L protein, resulting in a 30 amino acid section of the L-protein being erroneous (FIG. 2D). This discrepancy in the published LaSota sequence has been noted by others in the field (Römer-Oberdorfer, et al., 1999, J Gen Virol 80: 2987-2995). The frameshift is not present in the LaSota clone 30 (Accession No.: Y18898.1) or in many other published available sequences of NDV strains (i.e. Hitchner B1, Accession No.: AF375823). Because a fully-functional L protein in both the rNDV genome and the helper plasmid used for rescue is essential for initiation and maintenance of the virus replication cycle, the frameshift was corrected using LaSota clone 30 as a reference sequence, by replacing the portion of the L protein coding sequence with the error with a corrected nucleotide sequence (SEQ ID NO: 36). The sequence of the new, corrected vector was validated by restriction profile and sequencing. The final correct sequence of the rNDV is provided by SEQ ID NO: 16.

Example 2 Production of rNDV in EB66 Cells (Rescue and Propagation One-Step Method)

Virus rescue in EB66 cells

Figure 3:
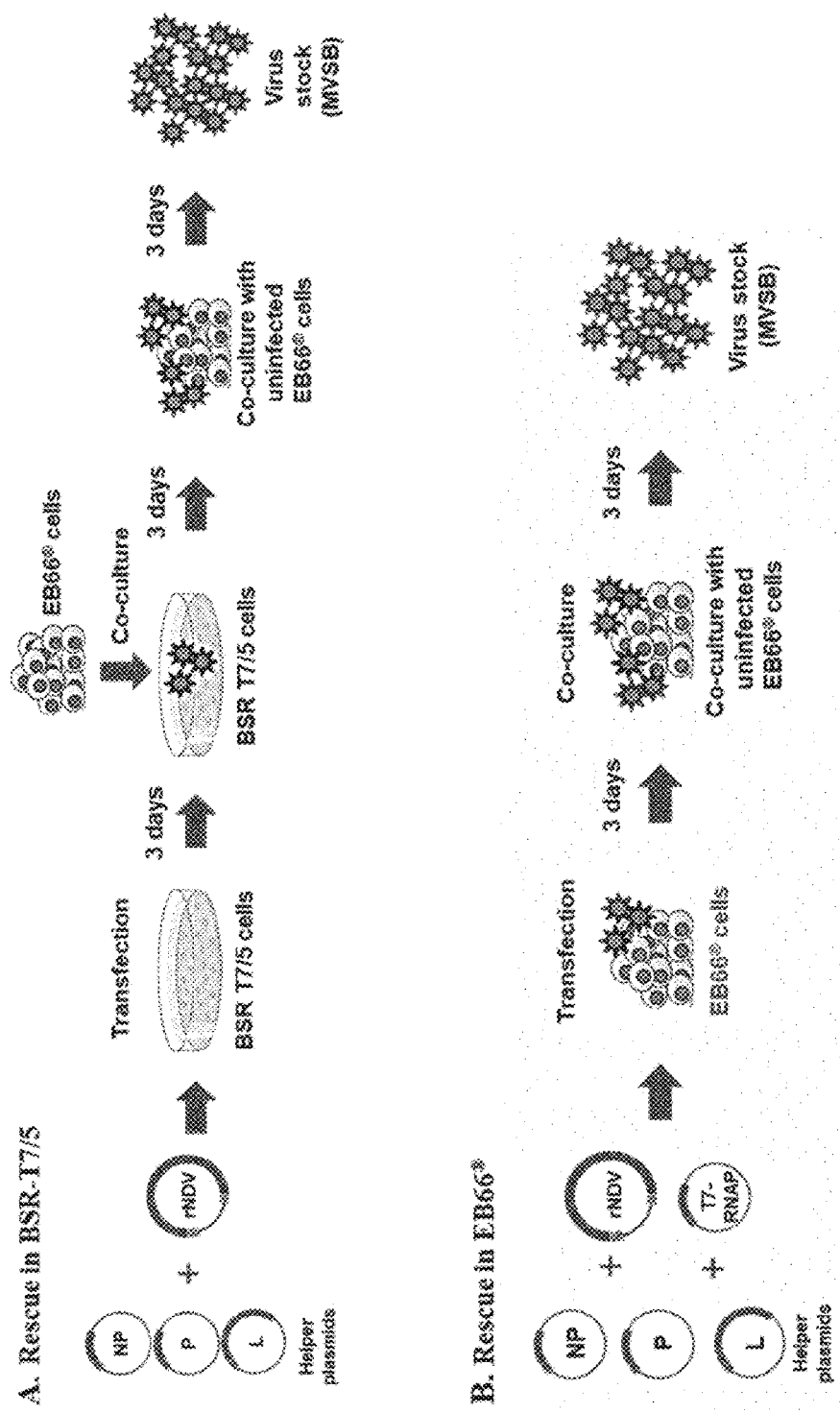
FIG. 3 Schematic comparison of conventional viral rescue and propagation with the process of the current invention using rNDV as an example. (A) Viral rescue from conventional BHK-derived cells stably expressing T7 polymerase (BSR T7/5) by transfection with rNDV and three helper plasmids, followed by viral propagation in EB66 cells; and (B) Viral rescue directly in EB66 cells by transfection with an rNDV expression vector, three helper plasmids and the addition of T7 RNA expression vector, followed by viral propagation in EB66 cells. T7-RNAP: T7 RNA polymerase under CMV promoter; NP: Nucleoprotein of NDV; P: Phosphoprotein of NDV; L: Polymerase of NDV; rNDV: recombinant NDV in pBR322Mod; MVSB: Master virus seed bank. The latter rescue protocol can facilitate the production of an rNDV master virus seed bank in as little as one week; i.e., transfection on day 0; co-culture with fresh EB66 cells at day 3 or 4 and harvest of MVSB on day 2 or 3 after infection (co-culture).

Viral rescue of RNA viruses is a method of generating viral particles by transfecting antigenomic cDNA or RNA into producing cells. As used herein, "plaque forming unit" (pfu) is used interchangeably with viral particle. In the case of rNDV rescue according to the current invention, the viral replication cycle is launched by the transfection of, in addition to the antigenomic cDNA (rNDV in pBR322Mod), helper plasmids encoding viral polymerase complex cDNAs (helpers P and L) and nucleoprotein (helper NP). Further, because EB66® cells do not constitutively express T7 polymerase, an additional plasmid expressing the T7 polymerase under a CMV promoter is also co-delivered. All helper plasmids are constructed on a pClneo plasmid (SEQ ID NO: 38) by insertion of coding sequences as provided in Table 2. A schematic comparison of a common rescue and propagation protocol using helper cells and the one-step protocol of the current disclosure is shown in FIG. 3.

The MaxCyte STX® Scalable Transfection System (MaxCyte, Inc.) was used to electroporate DNA into EB66® cells. The transfection was performed at a small scale using the OC-100 processing assembly (100 μL capacity; MaxCyte, Inc.). For each rescue, 10 μg of total DNA was transfected. The amounts and identities of the plasmids used in the transfection protocols are given in Table 2 below.

TABLE 2

Plasmids and amounts used for rNDV transfection.

| Conditions | Plasmid | SEQ ID NO of insert | μg DNA |
|---|---|---|---|
| rNDV (FL or with heterologous insert) | rNDV | 16 | 3.3 |
| | P helper | 40 | 0.7 |
| | NP helper | 39 | 1.6 |
| | L helper | 41 | 0.7 |
| | T7-RNA-pol | 42 | 4 |

DNA preparation

Thaw the DNA, homogenize by vortexing the tubes and centrifuge briefly.

Transfer into a 1.5 mL microtube the needed quantity for each tested condition. DNAs must be enough concentrated (ideally 2 to 5tig/tiL) to have maximum final volume of 10 μL.

EB66® cell preparation for transfection

Three days prior to the transfection step (d −3), cell amplification is initiated from a seeding of 0.4.10⁶ cells/mL in CDM4Avian medium+2.5 mM Gln).

Cell suspension is homogenized on d0.

1 mL of cell suspension is harvested and cells are counted.

Transfection protocol

Pre-warm culture medium (CDM4 Avian+2.5 mM Gln) to 37° C.

Homogenize the cell suspension and take the needed cell quantity for the experiment: 10×10 6 cells for each transfected condition.

Centrifuge 5 min at 1200 rpm.

Remove the supernatant and resuspend cells in MaxCyte buffer to a final concentration of 1×10 8 cells/mL.

Transfer 100 μL cell suspension into the respective microtubes containing the prepared DNA.

Homogenize cells with DNA, avoiding bubbles.

Distribute 100 μL of each transfection mix into OC-100 cassettes.

Proceed to the assembly of the OC-100 on MaxCyte device following the instructions on the computer, selecting "OC-100" and the program "OPT9".

Harvest the 100 μL of transfected cells using a P200 pipet and distribute the volume into one well of a 6-well plate, stirring with the pipet tip to distribute the cells in the well Gently agitate the plate to further distribute the cells.

Incubate plate for 30 minutes at 37° C., 7.5% $CO_2$ without shaking.

Add 2 mL per well of pre-warmed CDM4 avian media.

Figure 4:
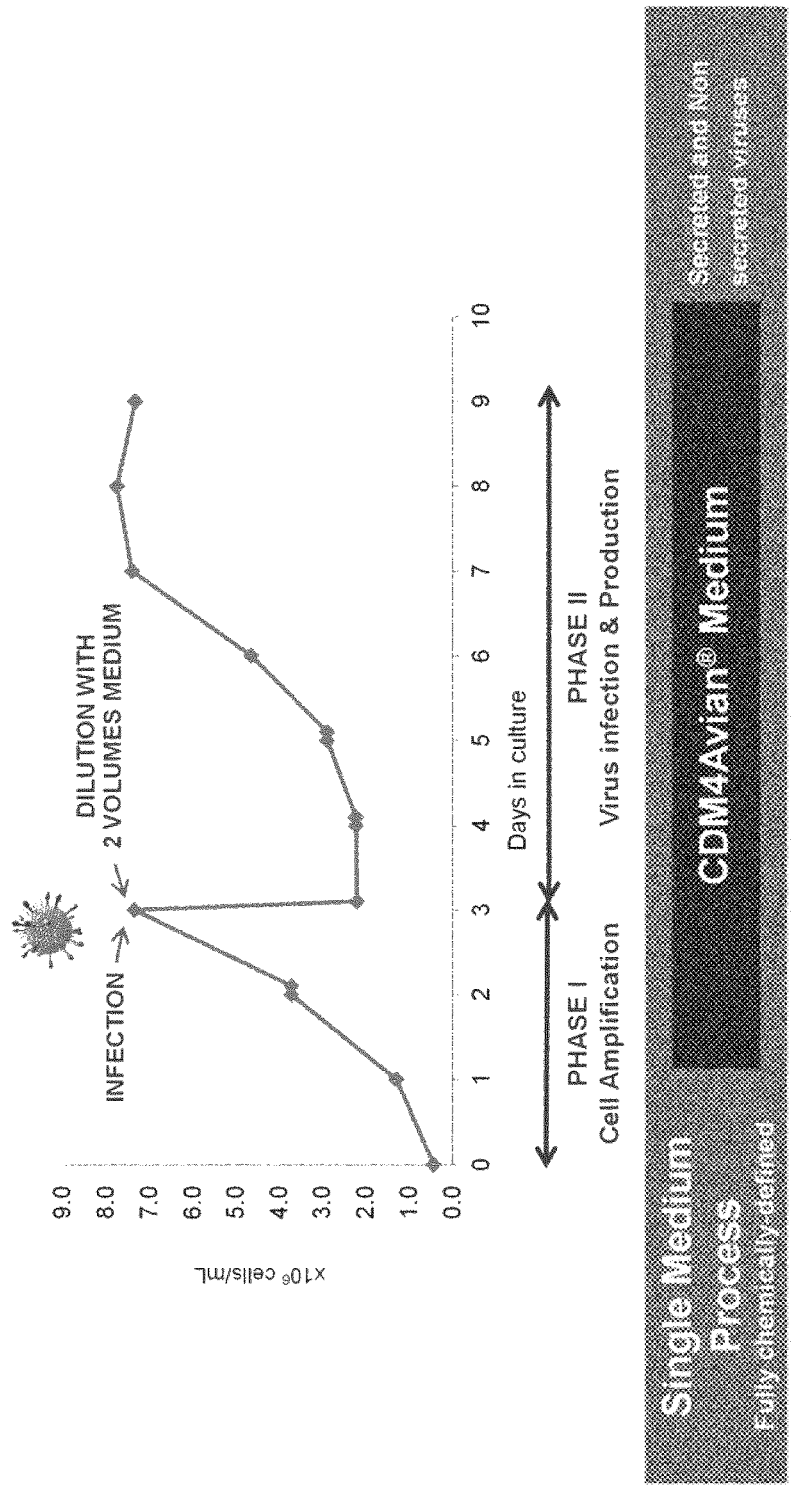
FIG. 4 Standard virus propagation process in EB66 cells grown in CDM4Avian® chemically-defined medium. In Phase I, the EB66 cells are amplified; in Phase II, the cells are diluted, infected with virus and expanded.

Incubate the cells up to 4 days, observing them daily for the appearance of CPEs Propagation of virus on EB66 cells Add fresh EB66 cells to the transfected cells Add trypzean daily at 0.75 USP/MVC Allow to incubate for 2-6 days before harvest The above one-step protocol for rescue and propagation can be used to generate a Master Virus Seed Bank, which can in turn be used to infect EB66 cells to produce Drug Substance. An example of such virus production in EB66 cells is shown schematically in FIG. 4.

Example 3 Expression of Heterologous Proteins Inserted into the rNDV Vector

Insertion of heterologous coding sequences into rNDV Heterologous sequences for insertion into the rNDV vector were synthesized (GeneArt) as autonomous transcription units (ATU), consisting of a gene-end NDV sequence, a start-end NDV sequence, a kozak sequence and the heterologous coding sequence (see FIG. 5A). To ensure correct and efficient NDV virus replication, the ATU was designed to follow the "rule of 6", based on the observation that efficient replication of NDV RNA is only possible if the genome size is a multiple of six nucleotides (Peeters, et al., 2000, Arch Virol, 145(9):1829-45). Each ATU is flanked by a restriction enzyme site for the cloning in the correct position between each gene of NDV, according to need. In the case of cloning hMPV F protein in the NDV genome, 5 different ATUs were synthesized (GeneArt), each with a single restriction site for the insertion of the F protein coding sequence into all possible intergenic positions in the NDV genome. An additional strategy was a construct with the hMPV F protein ATU being flanked by all 5 restriction enzyme sites (SEQ ID NO: 37). In one example (FIG. 5B), the hMPV F protein ATU from the B2 strain is inserted between NDV P and M protein coding sequences using the single FseI RE site (pVVS01866).

Figure 6:
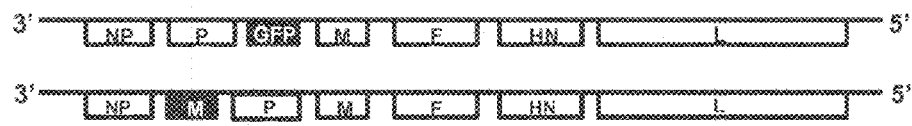
FIG. 6 Proof of principle of rNDV cloning platform for foreign gene expression. (A) An ATU containing a green fluorescent protein coding sequence (GFP; SEQ ID NO: 33) is inserted between P and M (rNDV-GFP) and an ATU containing an hMPV matrix protein (M-protein; SEQ ID NO: 34) coding sequence is inserted between NP and P of rNDV (rNDV-M); (B) Expression of proteins in EB66 cells as measured by flow cytometry in fixed EB66 cells on d2 after infection. M-protein was detected with anti-hMPV Matrix-protein-mouse IgG2a at 2 µg/mL (Genetex GTX36792).
Figure 6:
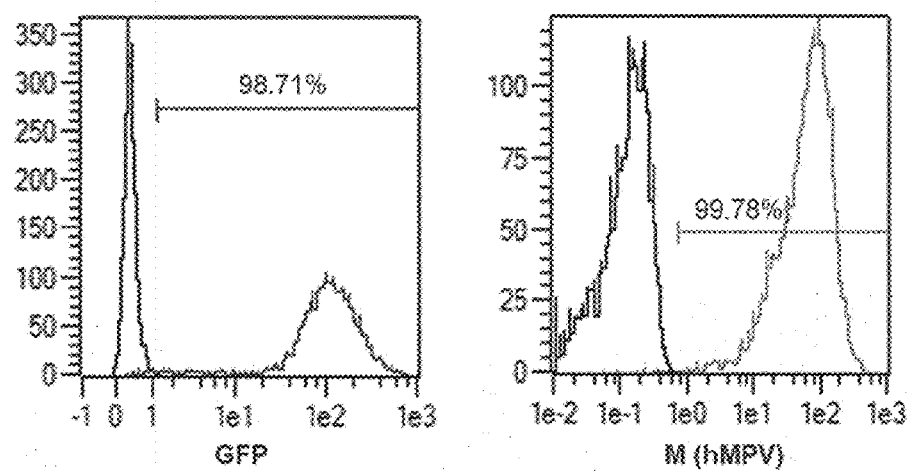

As schematically shown in FIG. 6, a coding sequence for green fluorescent protein (GFP; SEQ ID NO: 33) was inserted into rNDV between NDV P and M protein coding sequences by use of the FseI restriction site and a coding sequence for an hMPV matrix protein (M-protein; SEQ ID NO: 34) was inserted between NDV NP and P protein coding sequences by use of the AscI restriction site. Viral particles were rescued and used to infect EB66 cells. Briefly, 40 mL of EB66 amplified cells were transferred into T175 flasks, and infected with either NDV-GFP and/or NDV-M at an MOI of $10^{-3}$ TCID$_{50}$/cell. Infected cultures were incubated at 33° C., 7.5% CO$_2$, 135 rpm (IKA shaker) for one hour of adsorption. Infected cell cultures were then diluted with 60 mL (T175) of production media (CDM4 Avian) and re-incubated for infection kinetic. Trypzean at 0.75 USP/10$^6$ cells was added in all cultures at infection time and daily post infection.

Cells were fixed with paraformaldehyde and stained 2 days post-infection for flow cytometric analysis. For internal staining, cells were permeabilized before addition of the primary antibody with Perm/Wash buffer (Becton Dickinson). For surface staining, primary antibody was added before fixing the cells. The primary antibody was GTX36792 Anti M hMPV-mouse IgG2a (Genetex) at 211.g/mL and the secondary antibody was Fluorescein (FITC)-AffiniPure F(ab')2 Fragment Goat Anti-Mouse IgG+IgM (Jackson ImmunoResearch Cat. #115-096-068). Expression of both GFP and M-protein was observed in virtually all infected cells.

Figure 7:
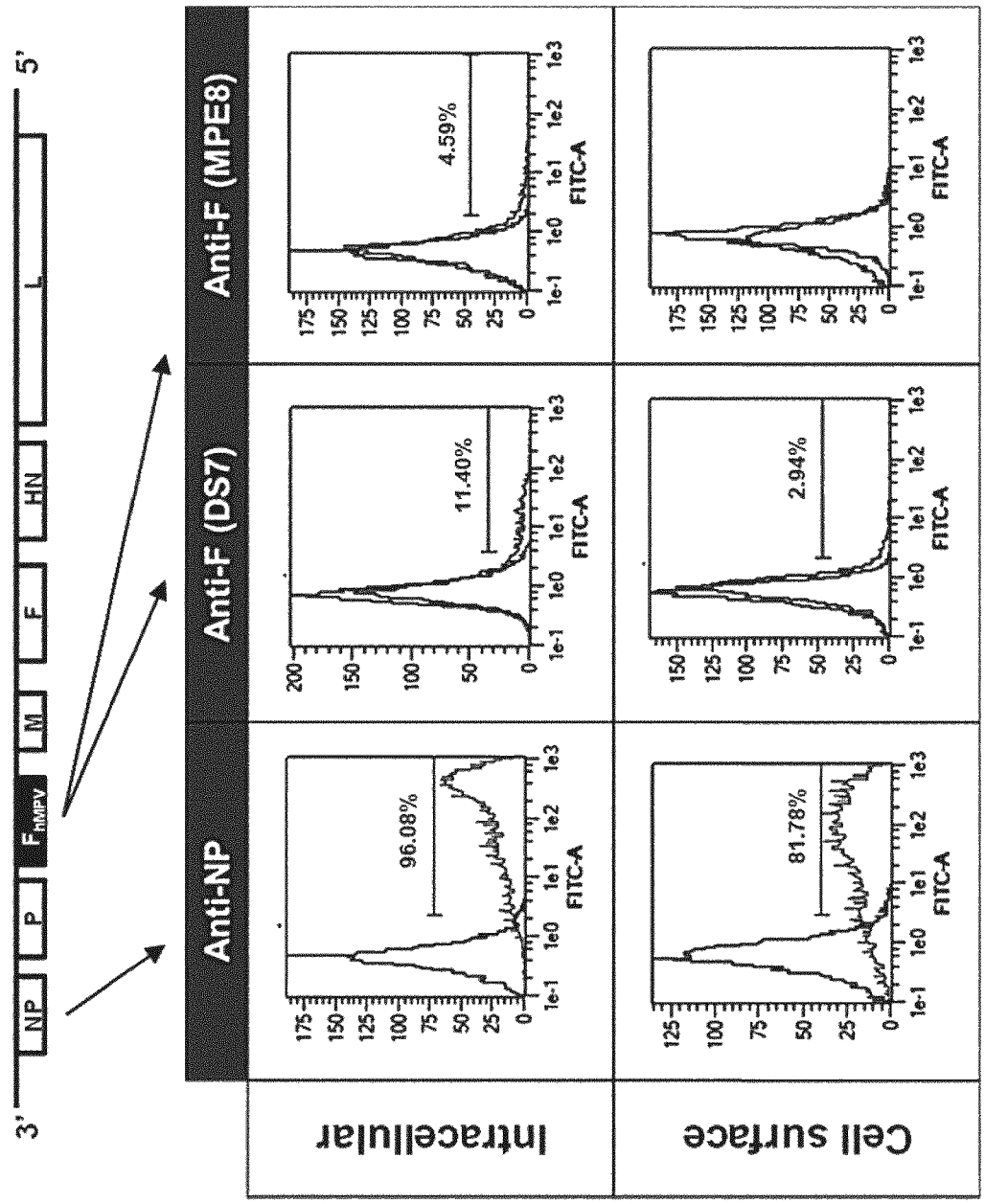
FIG. 7 Low expression of hMPV F-protein following insertion of the native coding sequence into rNDV. Insertion of the full-length wild-type F-protein coding sequence of A1 hMPV between P and M of rNDV LaSota (rNDV-FA1) resulted in high NDV titers following rescue and propagation in EB66 cells (~$10^{8-8.5}$ TCID$_{50}$/mL; data not shown), but low expression of hMPV F-protein overall (10-15%) and essentially no presentation on the surface of the infected cells (~3%) as measured by flow cytometry on permeabilized ("intracellular") and non-permeabilized cells ("cell surface"). The full-length hMPV F-protein coding sequence (FA1Native) is provided by SEQ ID NO: 27. F-protein antibodies used were DS7, which binds to both pre- and post-fusion forms of hMPV F-protein and MPEG, which is specific for the pre-fusion form (antibodies produced in-house).

As shown in FIG. 7, a coding sequence for full-length hMPV F-protein (FhMPV; SEQ ID NO: 37) was inserted between NDV P and M protein coding sequences by use of the FseI restriction site. Resulting recombinant viral particles were rescued and used to infect EB66 cell as described above. Two days post-infection, cells were fixed and stained with anti-NP (NDV) antibodies or Anti-F (hMPV antibodies DS7 or MPEG, to assess the expression of total hMPV F-protein and the presence of post-fusion forms of hMPV F-protein, respectively, by flow cytometry. As shown in FIG. 7, most of the infected cells expressed NDV NP protein, which was observed intracellularly and on the surface. Expression of FhMPV, however, was very low both intracellularly and on the surface. This observation suggested less than optimal conditions for expression of the FhMPV protein, in contrast with GFP and hMPV-M as shown in FIG. 6.

Figure 8:
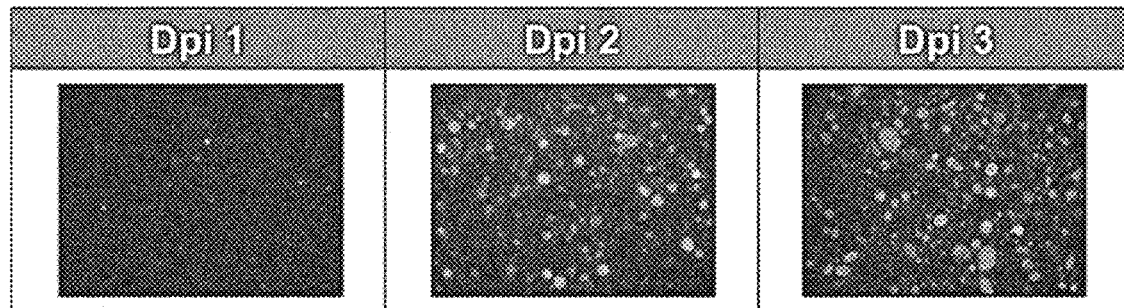
FIG. 8 Propagation of NDV in EB66 cells following viral rescue in BSR-T7/5 cells (A) rNDV-GFP propagation in EB66 ® cells: Transfection was done in 6-well plates using helper plasmids and the rNDV-GFP plasmid (GFP insert between P and M NDV protein coding sequences). 0.5 mL of supernatant from the co-culture step (EB66 ® cells added on BSR-T7/5 transfected cells) was used to infect 15×$10^6$ EB66 cells/well in 6-well plates. The infection kinetics were monitored post-infection (d1, d2 and d3 post-infection) by visualizing GFP expression under a UV microscopy. (B) Kinetics of viral production of rNDV-FL (rNDV without heterologous insert); rNDV-GFP (P/M) and rNDV-FA1 (hMPV F-protein native nt sequence) in EB66 ® cells. A LaSota NDV positive control was also used. Two multiplicities of infection (MOIs) were compared for each experimental construct: $10^{-2}$ and $10^{-4}$, calculated based on a theoretical titer of 1×$10^6$ log 10 TCID$_{50}$/mL. The TCID$_{50}$ assay was determined on HeLa cells according to standard protocols. Immunostaining of the HN protein was done for the conditions rNDV-FL and rNDV-FA1. Titers were calculated according the Reed-Muench method (Reed, L.J.; Muench, H. (1938) American Journal of Hygiene 27:493-497) and are expressed as Log TCID$_{50}$/mL. (C) Visualization of NDV NP protein and hMPV F-protein expression by immunostaining: EB66 cells infected with either the rNDV-FL or the rNDV-FA1 were stained with antibodies against NP protein of NDV (Abcam; Ab138719) or F M protein of hMPV (Abcam; Ab94800) in order to assess the expression of both proteins.
Figure 8:
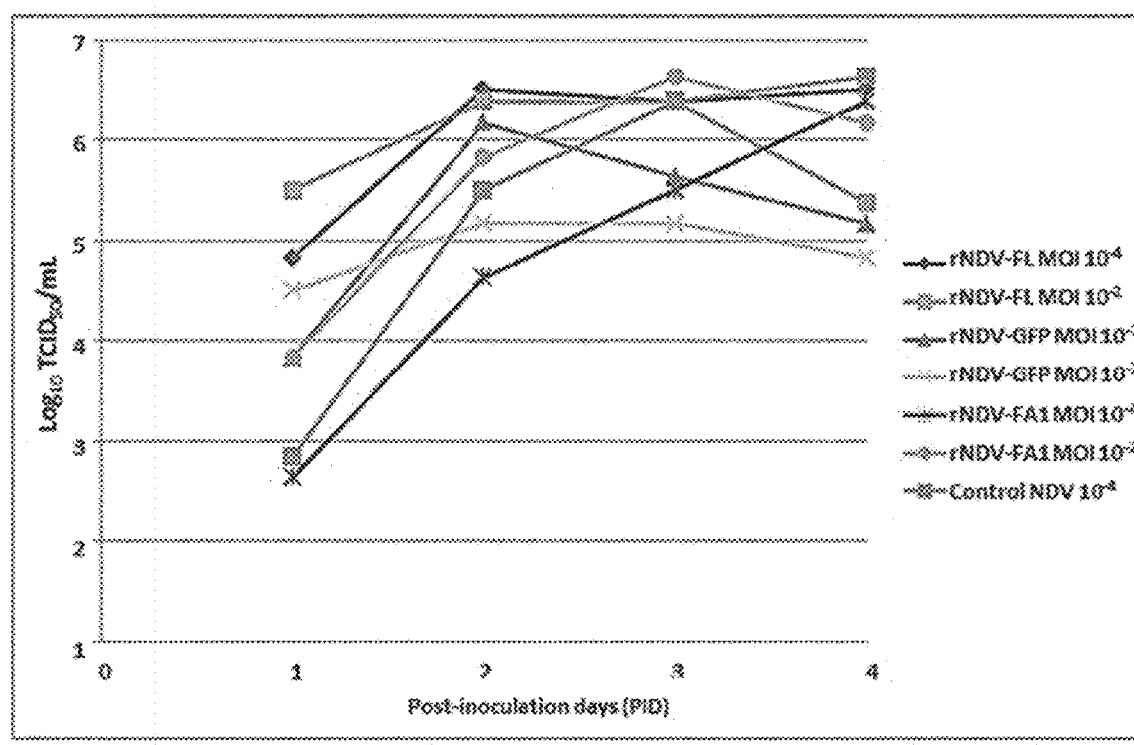
Figure 8:
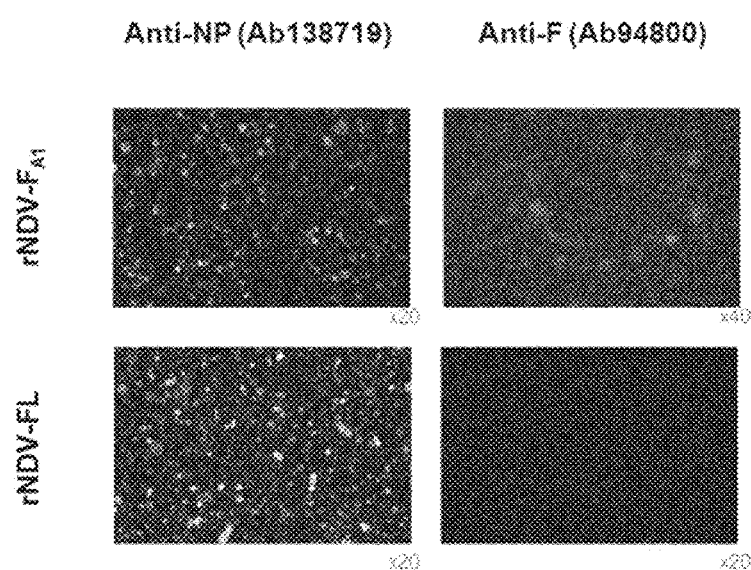

Production of rNDV with Heterologous Coding Sequence Inserts rNDV constructs with GFP and hMPV F-protein inserts were assessed for kinetics of heterologous protein production following EB66 cell infection. Transfection was done in 6-well plates using helper plasmids and the rNDV-GFP plasmid (GFP insert between P and M NDV protein coding sequences). 0.5 mL of supernatant from the co-culture step (EB66 ® cells added on BSR-T7/5 transfected cells) was used to infect 15×10$^6$ EB66 cells/well in 6-well plates. The infection kinetics were monitored post-infection (d1, d2 and d3 post-infection) by visualizing GFP expression under a UV microscopy. As shown in FIG. 8A, GFP production was already visible by day 1 after infection as visualized by fluorescence microscopy. Kinetics of viral production of rNDV-FL; rNDV-GFP (P/M) and rNDV-FA1 (P/M) and a LaSota NDV positive control were examined using two multiplicities of infection (MOIs): $10^{-2}$ and $10^{-4}$, calculated based on a theoretical titer of 1×10$^6$ log 10 TCID$_{50}$/mL. The TCID$_{50}$ assay was done on HeLa cells according to standard protocols. As shown in FIG. 8B, the presence of a heterologous protein did not seriously hinder the production of a high titer. Immunostaining of the HN protein was done for the conditions rNDV-FL and rNDV-FA1. Titers were calculated according the Reed-Muench method and are expressed as Log TCID$_{50}$/mL. Furthermore, production of hMPV F protein was verified by fluorescence microscopy using antibodies against the NP protein of NDV (Abcam; Ab138719) or the F_protein of hMPV (Abcam; Ab94800).

Example 4 Improvement of Heterologous Protein Expression

Codon Optimization of the FL hMPV A1 F-Protein

Poor protein expression in host cells can sometimes be attributed to use of sub-optimal codons; therefore, following the observation that FhMPV did not express well in the rNDV system, the sequence was optimized for expression in human cells by two commercial providers; GeneArt (GA; FOpt1) and GenScript (GS; FOpt2). The GA optimized sequence was further altered as follows: 1) to have a higher CpG dinucleotid content (33%; FOpt3), 2) to contain the signal sequence from the NDV F-protein instead of the hMPV F-protein (FOpt4) and 3) to have a lower CpG dinucleotide content (0%; FOpt5) (see Table 3 below).

TABLE 3

Codon-optimized hMPV A1 F-protein coding sequences.

| Nucleic acid construct | Optimization | SEQ ID NO: |
| --- | --- | --- |
| FNative (wild-type) | N/A | 27 |
| FOpt1 | GeneArt (GA) | 28 |
| FOpt2 | GenScript (GS) | 29 |
| FOpt3 | GA + high CpG content | 30 |
| FOpt4 | GA + signal peptide from NDV F-protein | 31 |
| FOpt5 | GA + low CpG content | 32 |

Figure 9:
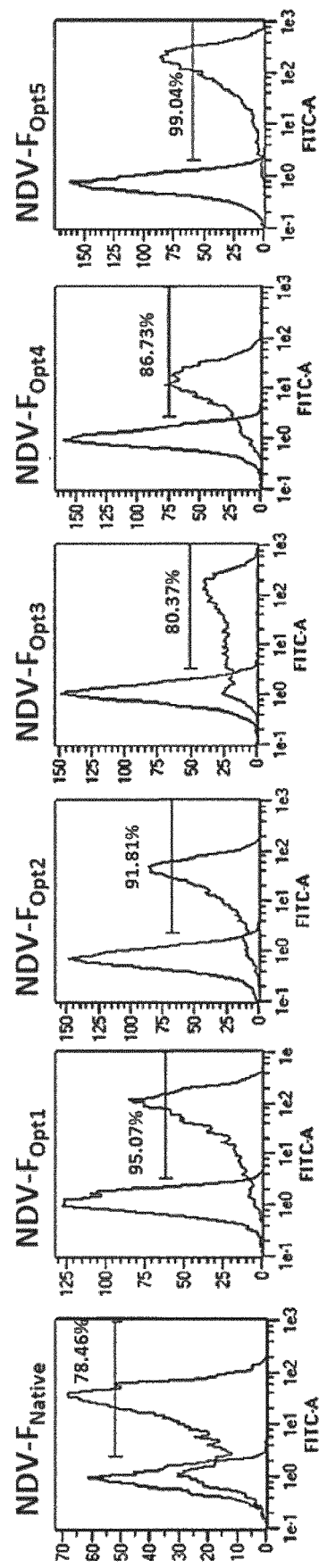
FIG. 9 Optimization of hMPV F-protein nucleotide sequence inserted into rNDV between the P and M protein coding sequences promotes expression in EB66 cells. (A) Comparison of total expression of hMPV F-protein with different coding sequences ($F_{Native}$ and $F_{Opt1-5}$) following virus rescue in permeabilized EB66 cells. (B) Comparison of intracellular and surface expression of hMPV F-protein on d3 of passage 1 following infection of EB66 cells with NDV comprising $F_{Native}$ and $F_{Opt1-5}$. (C) Comparison of total and surface expression of hMPV F-protein on d3 of passage 3. The native hMPV F-protein coding sequence ($F_{Native}$) is provided by SEQ ID NO: 27 and the optimized F-protein sequences ($F_{Opt1-Opt5}$) are provided by SEQ ID NOs: 28-32, respectively.
Figure 9:
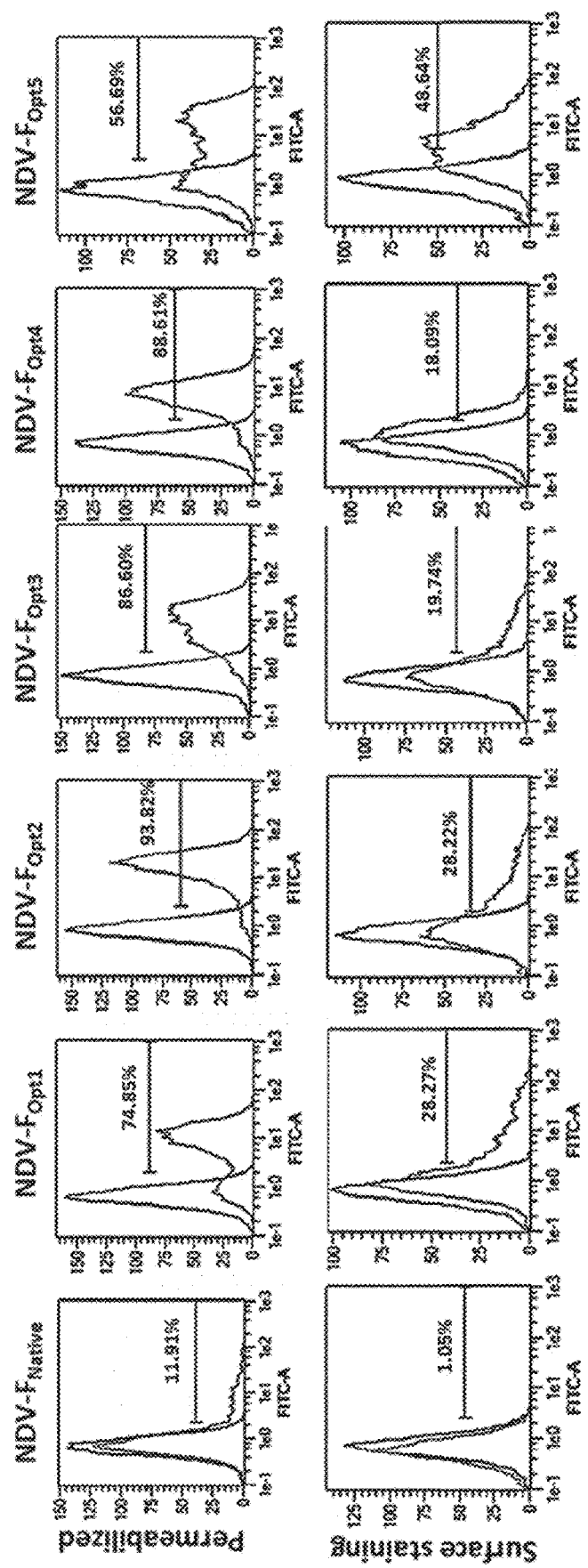
Figure 9:
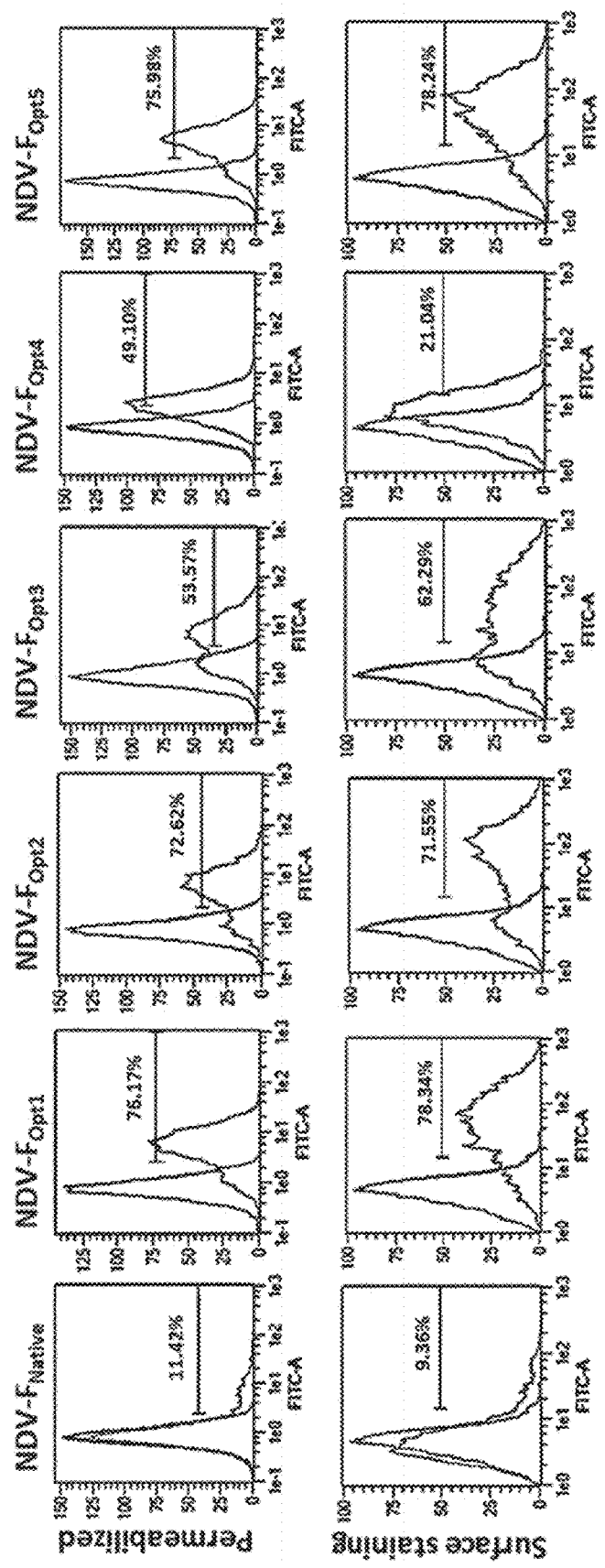

Comparative Expression of Optimized hMPV F-Protein Coding Sequences in rNDV Following Rescue and Up to Three Passages The codon-optimized sequences were cloned into the rNDV vector by use of RE FSEI. EB66 cells were transfected with the rNDV vectors and helper plasmids and allowed to rest 4 days after electroporation. Following that, 500 µL of the transfected cells were transferred into fresh EB66 cells and allowed to incubate for 3 days. As shown in FIG. 9A, total cellular expression of hMPV F-protein (permeabilized cells) was substantial with all F-protein sequences. After purification of the rescued virus, fresh EB66 cells were infected (p1) and allowed to incubate for 3 days before assessing total and cell-surface hMPV F-protein expression. As shown in FIG. 9B, the wild-type hMPV F-protein nucleic acid sequence resulted in the lowest expression at passage one. Finally, EB66 cells were infected with passage 3 (p3) rNDV particles with the respective hMPV F-protein coding sequences. As shown in FIG. 9C, the native hMPV F-protein coding sequence again resulted in very low levels of expression. The optimized sequences, however (with the exception of FOpt4) expressed high levels of the protein both internally and on the cell surface. It should be noted that day 1 antibody staining was done at 37° C. and day 3 staining at 4° C. to optimize surface staining, which may account for some increased surface staining observed in FIG. 9C. At higher temperatures, the antibody/F-protein complexes may be internalized (Leemans, et al., 2017, J Virol 91(14):e00184-17).

Example 5 Modification of the NDV F-Protein in rNDV-GFP

Many of the more virulent NDV strains, i.e., mesogenic and velogenic strains, possess an F-protein comprising a furin cleavage site instead of trypsin site, which results in the viral particles being more readily processed in the host cell. Alteration of the trypsin site in the current rNDV vector, therefore, might be expected to improve purification yield and/or enhance replication and immunogenicity in the host. Another mutation in the NDV F-protein, a Y527A point mutation, has been shown to enhance fusogenicity of the virus particles and to enhance immunogenicity (Manoharan et al., 2016, supra). As such, either of these changes in the NDV F-protein may be expected to enhance production and/or immunogenicity of NDV.

The trypsin cleavage site was modified in the rNDV-GFP expression vector (GFP coding sequence inserted between NDV P and M proteins as shown in FIG. 6A) in four different ways as shown in Table 4 below and a Y527A mutation was also introduced. These modifications should facilitate the replication and assembly of NDV particles in the methods disclosed herein, providing several advantages in terms of production and also with regard to effectiveness of the final drug substance:

1. Improve kinetics and efficiency of virus release from cells, increasing virus yield during production;
2. Avoid the need for daily addition of trypsin and for subsequent trypsin removal during the DSP (in case of trypsin site mutations);
3. Facilitate $TCID_{50}$ reading due to a more pronounced CPE; and/or
4. Improve viral replication in the subject to be treated.

TABLE 4

Sequence modification of the F-protein of rNDV

| Change in F-protein | Sequence | Source of sequence | SEQ ID NO: |
|---|---|---|---|
| Trypsin (wild-type) | 112 G-R-Q-G-R↓L 117 | La Sota NDV strain | 1 |
| Furin site 2 | 112 R-R-R-R-R↓L 117 | Beaudette C NDV strain | 2 |
| Furin site 3 | 112 R-R-Q-R-R↓F 117 | avian metapneumovirus | 3 |
| Furin site 5 | 112 R-R-Q-R-R↓F 117 | virulent and mesogenic NDV strains | 4 |
| Furin site 6 | 112 K-K-R-K-R↓L 117 | RSV F-protein | 5 |
| Y527A | Y527A | NDV F-protein | |

As shown in FIG. 10, modification of the trypsin site of the F-protein of rNDV resulted in kinetics of viral rescue similar to or better than kinetics of rNDV with the wild-type (trypsin) cleavage site. The furin site 5 cleavage site, present in some virulent strains of NDV, rendered NDV rescue substantially more efficient, with high levels of GFP expression by day 3 after rescue (see FIG. 10A). The furin site 5 mutant yielded about one log higher titers compared with the wild-type (trypsin) NDV at day 3 and day 6 post-infection (FIG. 10B). Furthermore, the furin site 5 mutant allowed rapid production of high NDV-GFP titers in the absence of trypsin treatment (FIG. 10C).

The terms "identical" or "percent identity" in the context of two or more nucleic acids or amino acid sequences refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, or 99% identity) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides (or about 10 amino acids) in length, or more preferably over a region that is 100 to 500 or 1000 or more nucleotides (or 20, 50, 200 or more amino acids) in length. In some embodiments, the identity exists over the length of a protein, such as an F protein.

For sequence comparison, typically one sequence acts as a reference sequence, to which test sequences are compared. Methods of alignment of sequences for comparison are well known in the art. See, e.g., by the local homology algorithm of Smith and Waterman (1981; Adv. Appl. Math. 2:482-489), by the homology alignment algorithm of Needleman and Wunsch (1970; J. Mol. Biol. 48:443), by the search for similarity method of Pearson and Lipman (1998; Proc. Natl. Acad. Sci. USA 85:2444-2448), by computerized implementations of various algorithms (GAP, BESTFIT, FASTA, Jalview and TFASTA in the Wisconsin Genetics Software Package, Genetics Computer Group. 575 Science Dr., Madison, WI), by multi-sequence alignment implementation using, e.g. CLUSTALW (Larkin et al., 2007, Bioinformatics, 23:2947-2948) or MAFFT (Katoh and Toh, 2008, Briefings in Bioinformatics 9:286-298), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul, et al., 1997, Nuc. Acids Res. 25(17): 3389-3402 and Altschul et al., 1990, J. Mol. Biol. 215:403-410, respectively.

The entire contents of all of the references (including literature references, issued patents, published patent applications, and co-pending patent applications) cited throughout this application are hereby expressly incorporated by reference.

The invention claimed is:

1. A method of producing infectious paramyxovirus particles comprising the steps of
   a) transfecting a duck cell line with
      (i) a vector comprising a paramyxovirus nucleic acid sequence under T7 control, wherein said vector comprising a paramyxovirus nucleic acid sequence under T7 control additionally comprises a T7 promotor sequence as defined by SEQ ID NO: 6 and a T7 terminator sequence as defined by SEQ ID NO: 7;
      (ii) a T7 RNA polymerase expression vector; and
      (iii) three further expression vectors comprising, respectively, paramyxovirus phosphoprotein (P), nucleoprotein (N), and polymerase (L) coding sequences; and
   b) culturing said transfected duck cell line under conditions for production of infectious paramyxovirus particles.

2. The method of claim 1, wherein said T7 RNA polymerase expression vector and three further expression vectors are under control of a constitutive promoter.

3. The method of claim 1, wherein the infectious paramyxovirus is a wild-type paramyxovirus, a chimeric paramyxovirus, or a recombinant paramyxovirus.

4. The method of claim 1, wherein the paramyxovirus nucleic acid sequence is modified to contain one or more restriction enzyme sites for insertion of a heterologous coding sequence located between the paramyxovirus protein coding sequences.

5. The method of claim 1, wherein the paramyxovirus nucleic acid sequence contains coding sequences for one or more foreign antigens.

6. The method of claim 1, wherein said paramyxovirus nucleic acid sequence contains coding sequences for one or more foreign antigens selected from the group consisting of antigens from viral pathogens, oncolytic proteins, and immunomodulating proteins.

7. The method of claim 1, wherein said paramyxovirus nucleic acid sequence contains coding sequences for one or more human metapneumovirus (hMPV) antigen and/or respiratory syncytial virus (RSV) antigen.

8. The method of claim 1, wherein said paramyxovirus nucleic acid sequence contains coding sequences for fusion (F) protein and/or matrix (M) protein from human metapneumovirus (hMPV) and/or respiratory syncytial virus (RSV).

9. The method of claim 8, wherein said F and M proteins assemble to produce hMPV or RSV virus-like particles.

10. The method according to claim 8, wherein said F protein from hMPV or RSV is a wild-type F protein, a modified F protein, an F protein in pre-fusion conformation, or an F protein in a post-fusion conformation.

11. The method according to claim 8, wherein said hMPV F protein is selected from the group consisting of SEQ ID NOs: 17-20 and immunogenic variants having at least 95% sequence identity to any one of SEQ. ID NOs: 17-20.

12. The method of claim 1, wherein the paramyxovirus nucleic acid is a Newcastle Disease Virus (NDV) nucleic acid, an NDV LaSota strain nucleic acid, an NDV Hitchner 131 strain nucleic acid, or an NDV AE2240 strain nucleic acid.

13. The method of claim 1, wherein the paramyxovirus nucleic acid encodes a wild-type Newcastle Disease Virus (NDV) genome, a chimeric NDV genome, a recombinant NDV genome, or a virus-like particle comprising NDV elements.

14. The method of claim 13, wherein the recombinant NDV genome is defined by SEQ ID NO: 16.

15. The method of claim 2, wherein the constitutive promoter is a cytomegalovirus (CMV) promoter.

* * * * *